US010980591B2

(12) United States Patent
Canady et al.

(10) Patent No.: US 10,980,591 B2
(45) Date of Patent: Apr. 20, 2021

(54) MULTI-FUNCTIONAL ELECTROSURGICAL PLASMA ACCESSORY

(71) Applicant: U.S. Patent Innovations LLC, Takoma Park, MD (US)

(72) Inventors: Jerome Canady, Lakeland, FL (US); Taisen Zhuang, Vienna, VA (US); Dereck Chiu, Arlington, VA (US); Siddhant Chawla, Dublin, OH (US)

(73) Assignee: U.S. Patent Innovations LLC, Takoma Park, MD (US)

( * ) Notice: Subject to any disclaimer, the term of this patent is extended or adjusted under 35 U.S.C. 154(b) by 464 days.

(21) Appl. No.: 15/305,914

(22) PCT Filed: Apr. 23, 2015

(86) PCT No.: PCT/US2015/027402
§ 371 (c)(1),
(2) Date: Nov. 14, 2016

(87) PCT Pub. No.: WO2015/164676
PCT Pub. Date: Oct. 29, 2015

(65) Prior Publication Data
US 2017/0312003 A1 Nov. 2, 2017

Related U.S. Application Data

(60) Provisional application No. 61/983,448, filed on Apr. 23, 2014, provisional application No. 62/050,584, filed on Sep. 15, 2014.

(51) Int. Cl.
*A61B 18/04* (2006.01)
*A61B 18/14* (2006.01)
(Continued)

(52) U.S. Cl.
CPC .. *A61B 18/042* (2013.01); *A61B 2017/00473* (2013.01); *A61B 2018/0091* (2013.01);
(Continued)

(58) Field of Classification Search
CPC ........ A61B 18/042; A61B 2018/00101; A61B 2018/00172; A61B 2018/00196
See application file for complete search history.

(56) References Cited

U.S. PATENT DOCUMENTS 4,040,426 A 8/1977 Morrison
4,060,086 A * 11/1977 Storz .................... A61B 18/149
606/46
(Continued)

FOREIGN PATENT DOCUMENTS

WO 2012061535 A2 5/2012

*Primary Examiner* — Michael F Peffley
*Assistant Examiner* — Bo Ouyang
(74) *Attorney, Agent, or Firm* — 24IP Law Group USA, PLLC; Timothy DeWitt

(57) ABSTRACT

A multi-functional electrosurgical plasma accessory having a handpiece and an extendable probe assembly. The extendable probe assembly has a shaft member, a tube, an electrode, a spacer and a collet. The shaft member and tube each may be formed of a plurality of structures assembled together, each may be of a single unitary design, or both together may be of a single unitary design. The shaft member has an interior channel, a distal end and a proximal end comprised of a neck portion at the distal end of the shaft member, a grip. The elongated portion of the shaft is movable within the spacer between a first position in which a portion of a distal end of the electrode extends out of the tube and a second portion in which the distal end of the electrode does not extend out of the tube.

15 Claims, 61 Drawing Sheets

(51) Int. Cl.
  *A61B 18/00* (2006.01)
  *A61B 17/00* (2006.01)
  *A61B 90/00* (2016.01)
(52) U.S. Cl.
  CPC ............ *A61B 2018/00101* (2013.01); *A61B 2018/00172* (2013.01); *A61B 2018/00178* (2013.01); *A61B 2018/00196* (2013.01); *A61B 2018/00583* (2013.01); *A61B 2018/00589* (2013.01); *A61B 2018/1475* (2013.01); *A61B 2090/034* (2016.02)

(56) References Cited

U.S. PATENT DOCUMENTS

| | | |
|---|---|---|
| 4,429,694 A | 2/1984 | McGreevy |
| 4,781,175 A | 11/1988 | McGreevy |
| 5,088,997 A | 2/1992 | Delahuerga et al. |
| 5,098,430 A | 3/1992 | Fleenor |
| 5,207,675 A | 5/1993 | Canady |
| 5,217,457 A | 6/1993 | Delahuerga et al. |
| 5,688,269 A | 11/1997 | Newton |
| 5,836,944 A | 11/1998 | Cosmescu |
| 6,149,648 A | 11/2000 | Cosmescu |
| 6,391,027 B1* | 5/2002 | Farin .................. A61B 18/042 606/34 |
| 6,458,125 B1 | 10/2002 | Cosmescu |
| 6,514,248 B1* | 2/2003 | Eggers .............. A61B 18/1492 606/41 |
| 6,837,884 B2 | 1/2005 | Woloszko |
| 7,517,347 B2 | 4/2009 | Hug et al. |
| 2005/0113825 A1 | 5/2005 | Cosmescu |
| 2006/0052774 A1 | 3/2006 | Garrison |
| 2006/0122595 A1 | 6/2006 | Farin |
| 2006/0224223 A1* | 10/2006 | Podhajsky .......... A61B 18/148 607/117 |
| 2007/0225699 A1 | 9/2007 | Goble |
| 2008/0058801 A1 | 3/2008 | Taylor |
| 2009/0171147 A1* | 7/2009 | Lee .................. A61B 17/29 600/104 |
| 2011/0282150 A1 | 11/2011 | Yamakawa |
| 2001/0301412 | 12/2011 | Cho |
| 2013/0060278 A1* | 3/2013 | Bozung ................. A61B 34/25 606/205 |
| 2014/0155888 A1* | 6/2014 | Edwards ........... A61B 18/1482 606/42 |

* cited by examiner

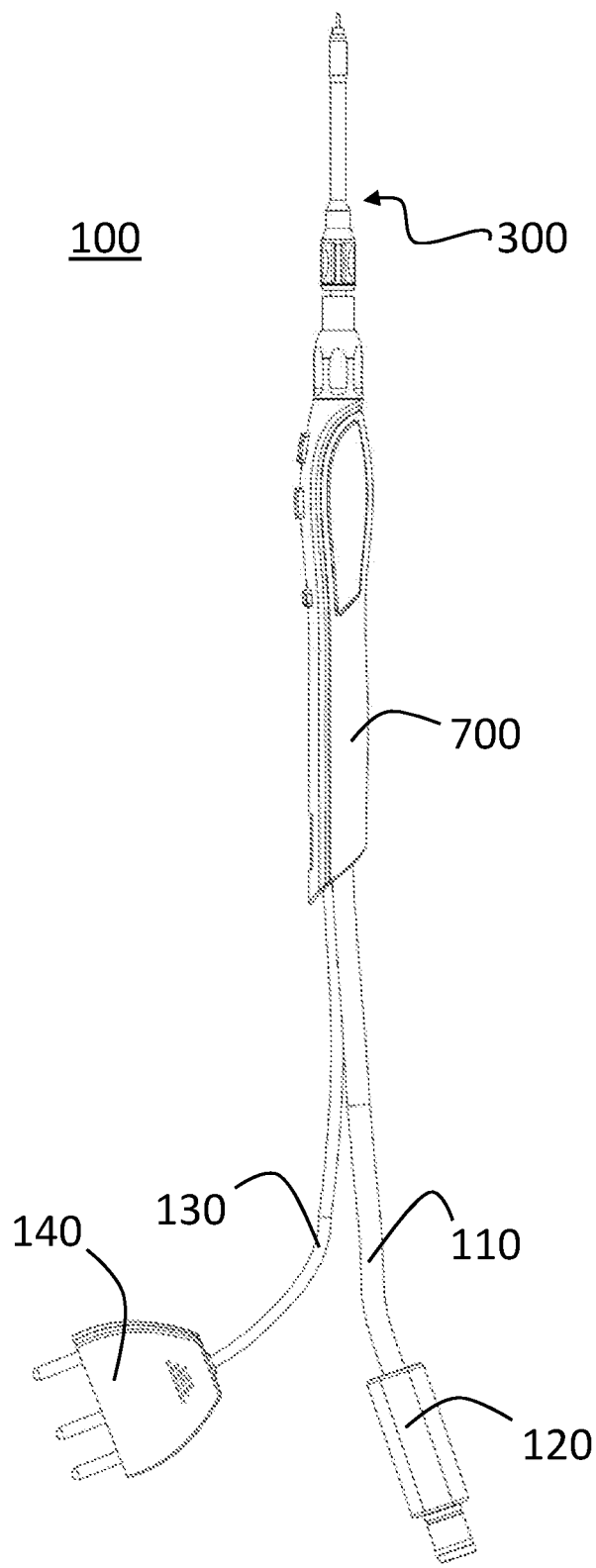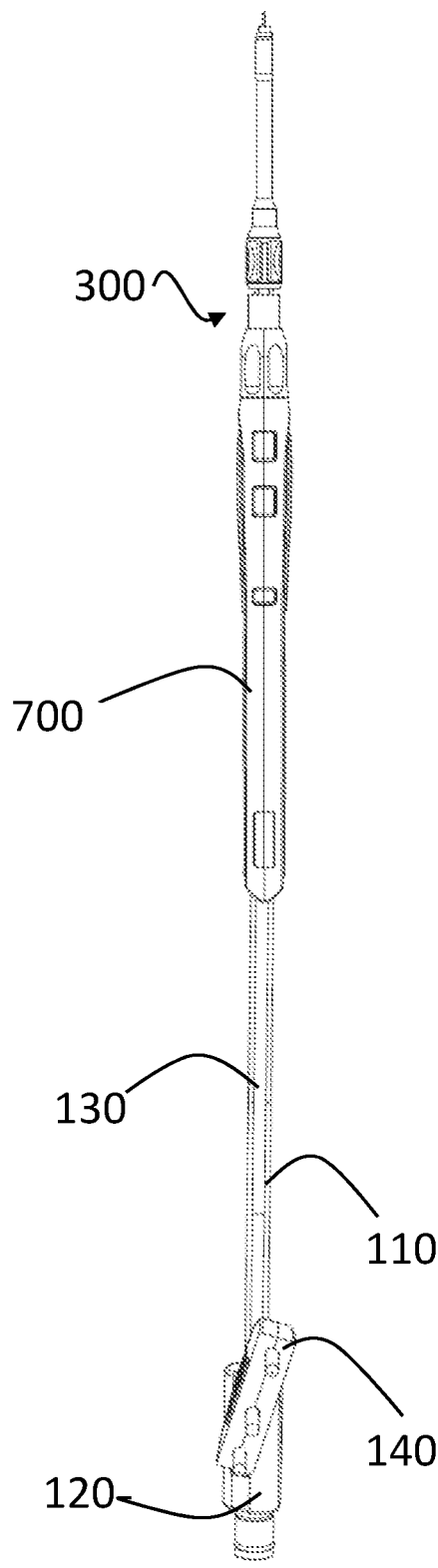
FIG. 1A
FIG. 1B

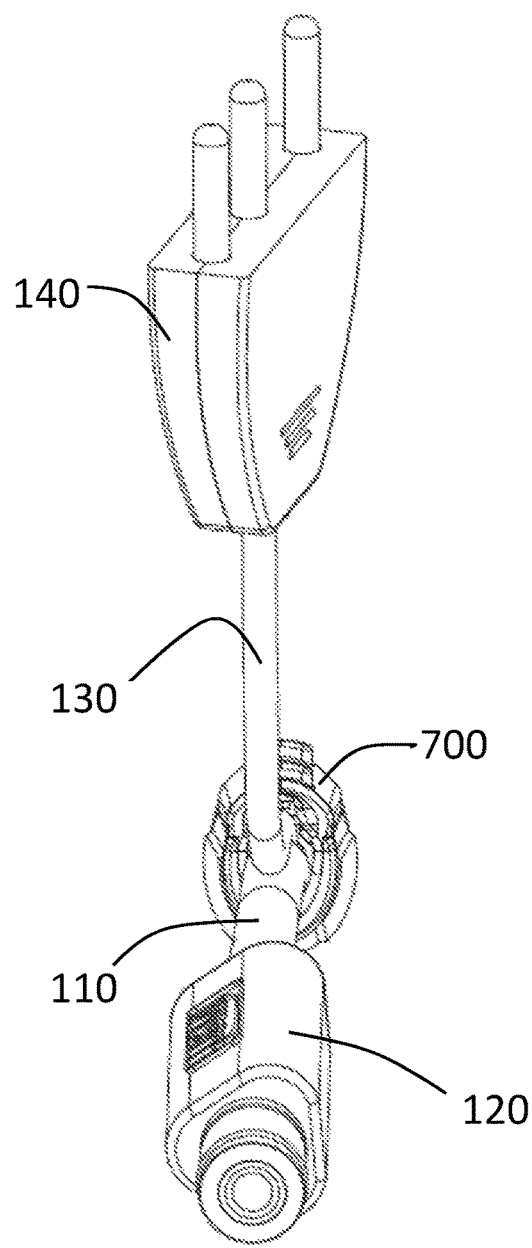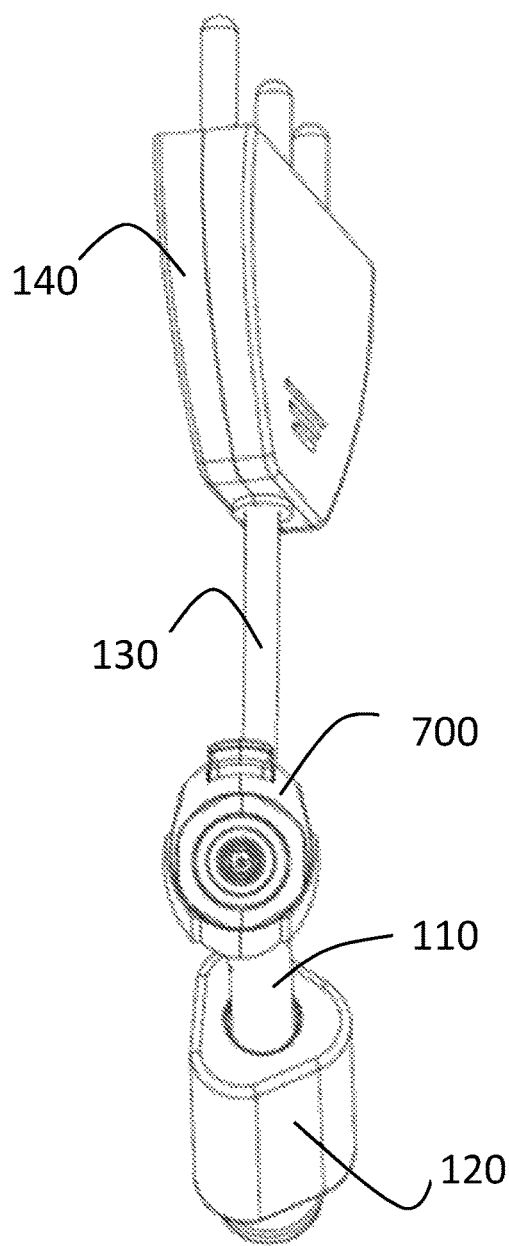
FIG. 1E
FIG. 1F

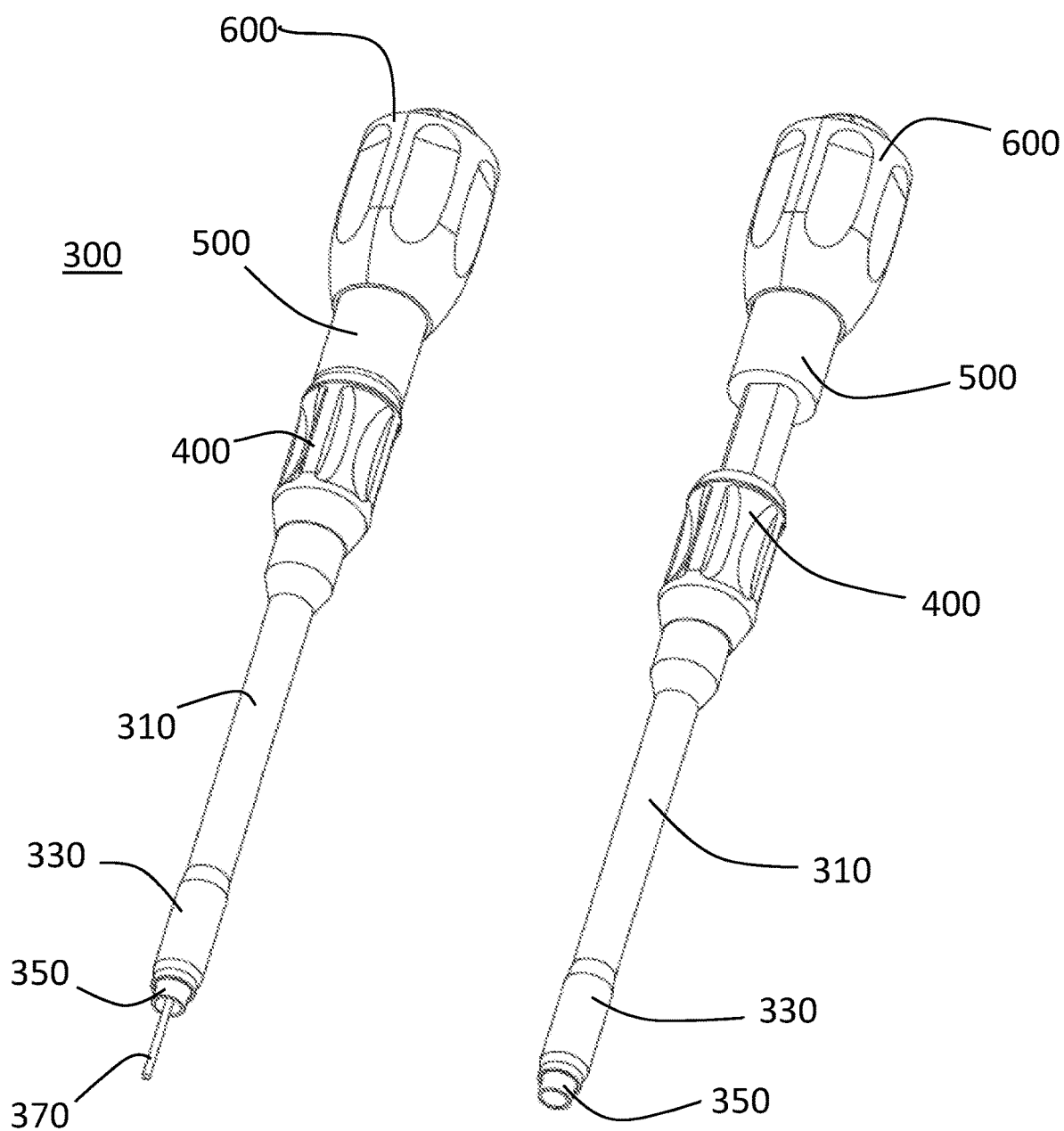

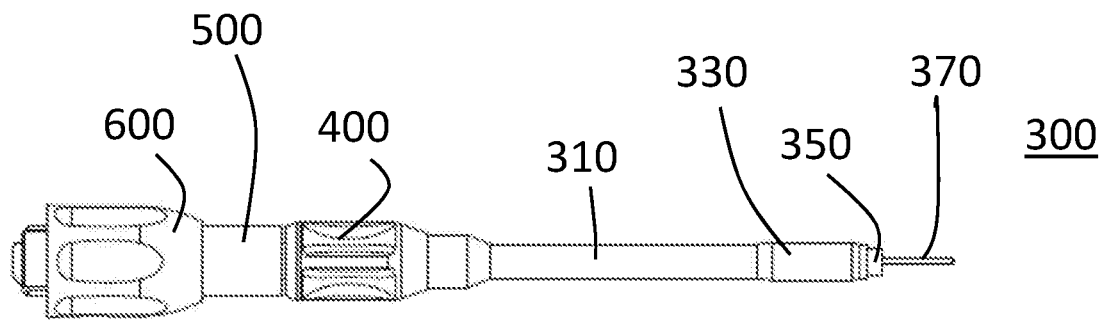
FIG. 2C
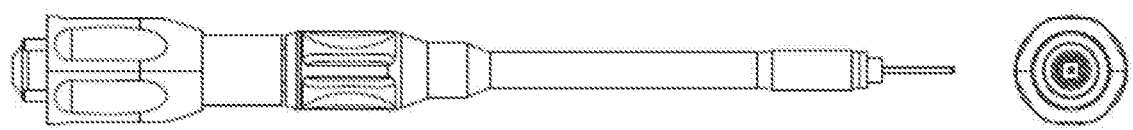 
FIG. 2D    FIG. 2E
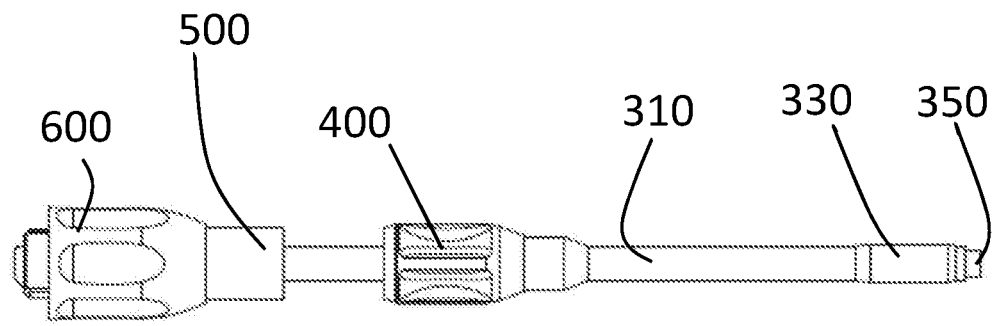
FIG. 2F
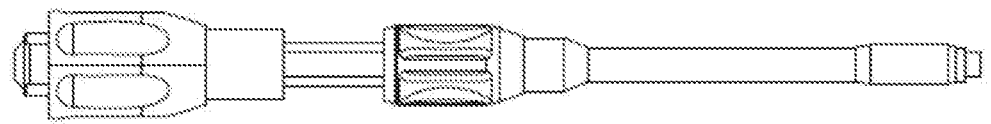
FIG. 2G

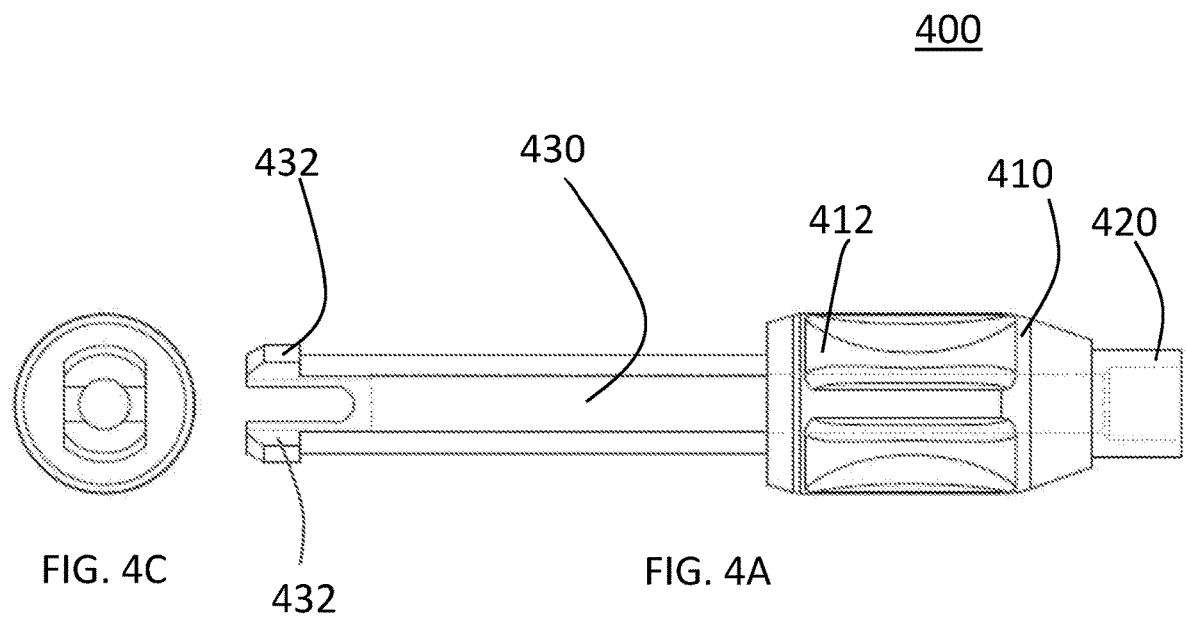
FIG. 4C
FIG. 4A
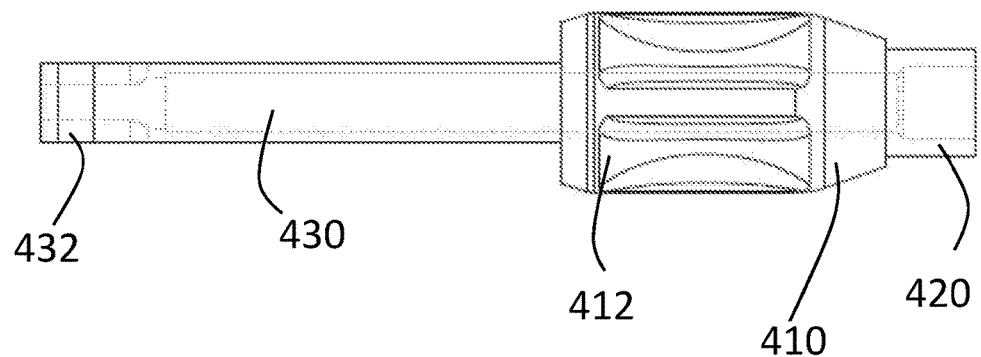
FIG. 4B

600

610
612

620

754

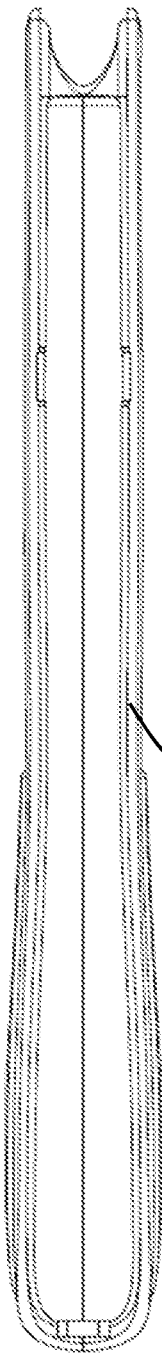
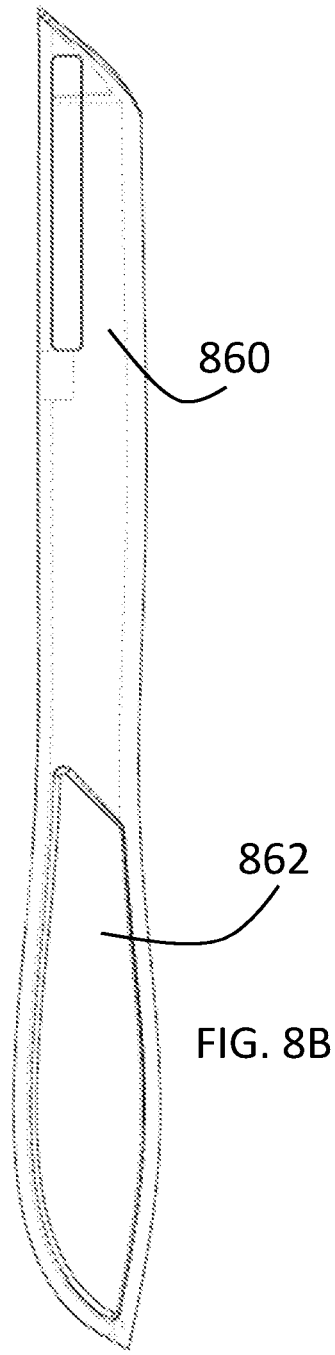
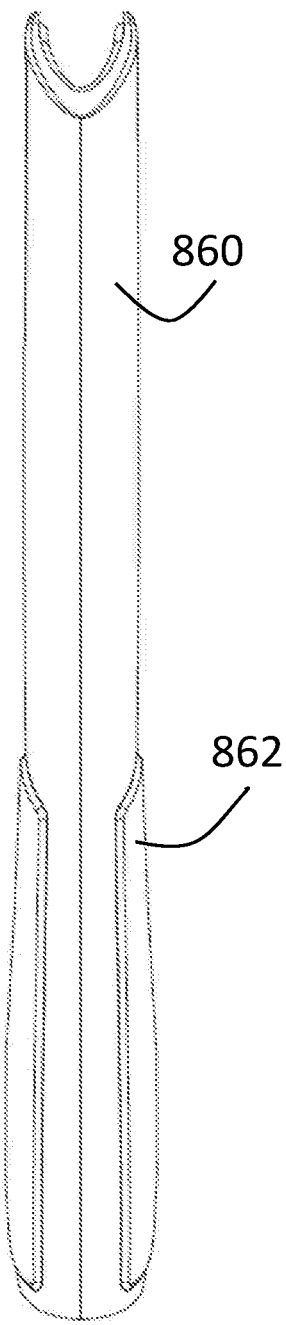
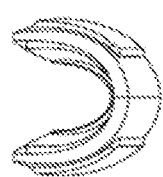
FIG. 8A
FIG. 8B
FIG. 8D
FIG. 8C

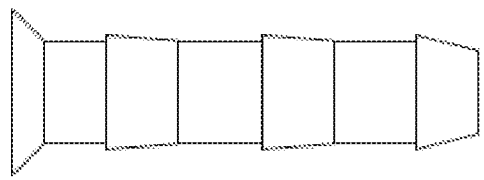
1000
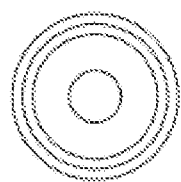
FIG. 10B
FIG. 10A
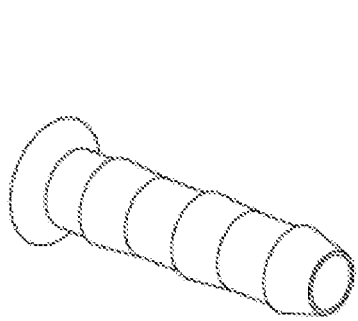
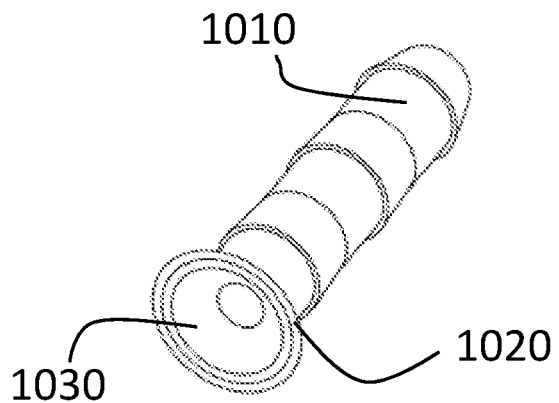
FIG. 10C
FIG. 10D

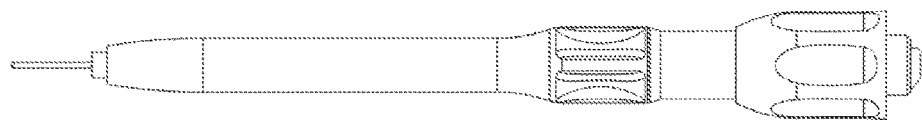
FIG. 12C
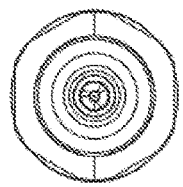 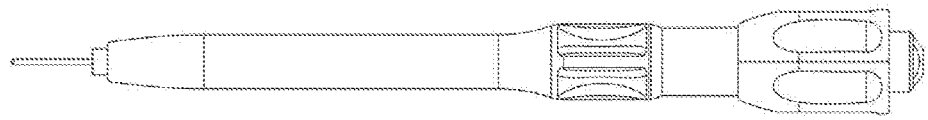
FIG. 12E  FIG. 12D
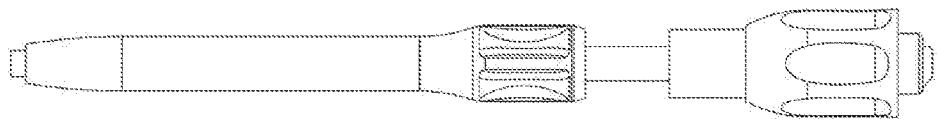
FIG. 12F
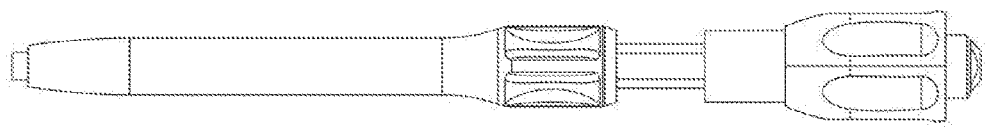
FIG. 12G

1654

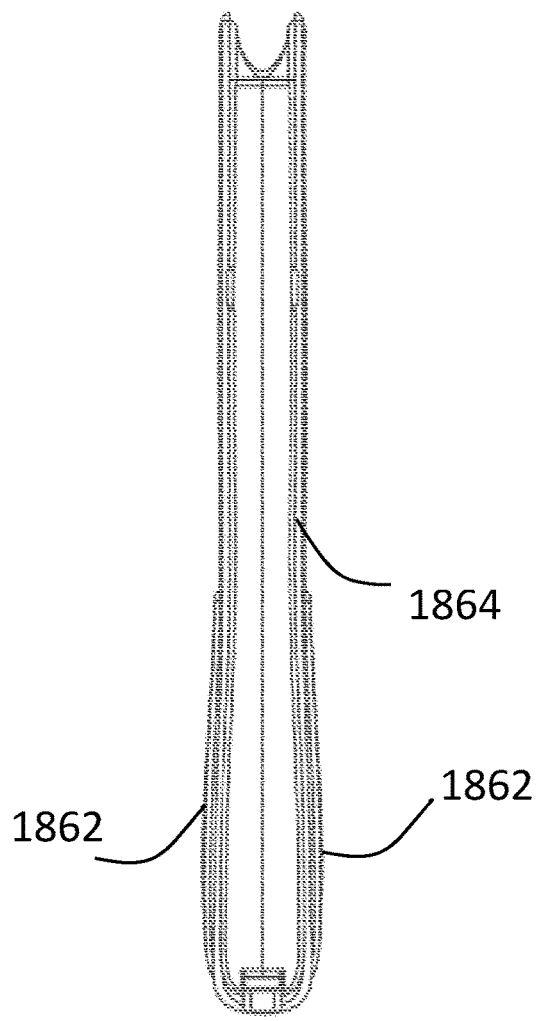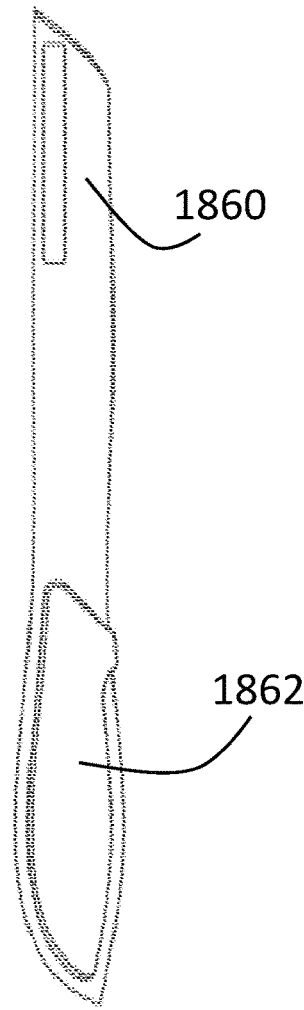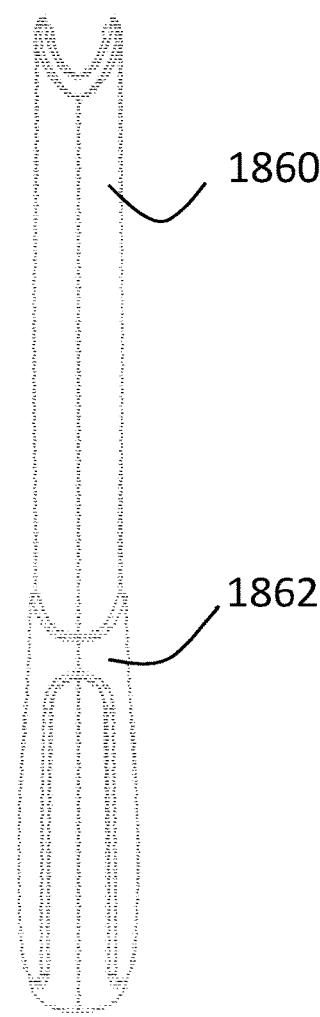
FIG. 17A        FIG. 17B        FIG. 17C
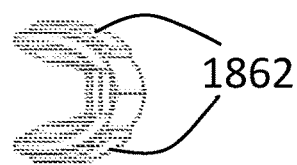
FIG. 17D

MULTI-FUNCTIONAL ELECTROSURGICAL PLASMA ACCESSORY

CROSS-REFERENCE TO RELATED APPLICATIONS

The present application claims the benefit of the filing date of U.S. Provisional Patent Application Ser. No. 61/983,448 filed by the present inventors on Apr. 23, 2014, and U.S. Provisional Patent Application Ser. No. 62/050,584 filed on Sep. 15, 2014.

The aforementioned provisional patent applications are hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to electrosurgical systems and methods, and more particularly, to a multi-functional electrosurgical plasma accessory.

Brief Description of the Related Art

The standard means for controlling traumatic and surgical blood loss are electrosurgical generators and lasers which respectively direct high-frequency electrical currents or light energy to localize heat in bleeding vessels so as to coagulate the overlying blood and vessel walls. Hemostasis and tissue destruction are of critical importance when removing abnormal tissue during surgery and therapeutic endoscopy. For monopolar electrosurgery electrical energy originates from an electrosurgical generator and is applied to target tissue via an active electrode that typically has a small cross-sectional surface-area to concentrate electrical energy at the surgical site. An inactive return electrode or patient plate that is large relative to the active electrode contacts the patient at a location remote from the surgical site to complete and electrical circuit through the tissue. For bipolar electrosurgery, a pair of active electrodes are used and electrical energy flows directly through the tissue between the two active electrodes.

U.S. Pat. No. 4,429,694 to McGreevy disclosed a variety of different electrosurgical effects that can be achieved depending primarily on the characteristics of the electrical energy delivered from the electrosurgical generator.

Another method of monopolar electrosurgery via argon plasma technology was described by Morrison U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. In U.S. Patent Application Publication No. 2013/0296848, Canady et al. described electrosurgical systems and methods using argon plasma during cutting modes of operation.

SUMMARY OF THE INVENTION

In a preferred embodiment, the present invention is a multi-functional electrosurgical plasma accessory. The accessory has a handpiece and an extendable probe assembly.

In a preferred embodiment, the present invention is an attachment for an electrosurgical system. The attachment comprises an extendable probe assembly that may be connected to an electrosurgical handpiece, housing, connector or other apparatus. The extendable probe assembly has a shaft member, a tube, an electrode, a spacer and a collet. The shaft member and tube each may be forms of a plurality of structures assembled together, each may be of a single unitary design, or both together may be of a single unitary design. The shaft member has an interior channel, a distal end and a proximal end comprised of a neck portion at the distal end of the shaft member, a grip portion and an elongated portion extending toward the proximal end of the shaft member. The elongated portion has a shaft stop member and an alignment feature. The tube has an interior channel and has a proximal end secured within the shaft and a distal end extending from the distal end of the shaft, an electrode within the interior channel of the tube, and spacer and a collet. The spacer is movably connected to the shaft member and is comprises of a body having an interior channel for slidably receiving the elongated portion of the shaft member, the interior channel having an interior alignment feature for aligning the interior channel of the spacer with the alignment feature of the elongated portion of the shaft, a spacer stop member and an outer alignment feature. The collet connects the probe assembly to an electrosurgical handpiece, connector or other apparatus. The collet has an interior ridge for engaging the spacer stop member and having interior threads for engaging with threads on the electrosurgical handpiece. The elongated portion of the shaft is movable within the spacer between a first position in which a portion of a distal end of the electrode extends out of the tube and a second portion in which the distal end of the electrode does not extend out of the tube. The probe assembly may further comprise a heat resistant tube abutting a distal end of the tube surrounding the electrode. Further, the probe assembly may have a stiffening member over the abutment between the heat resistant tube and the distal end of the elongated tube. The shaft stop member may comprise a plurality of tines extending from a proximal end of the elongated portion of the shaft. The alignment feature of the shaft comprises a flat surface on the elongated portion of the shaft and the interior alignment feature of the spacer comprised a flat surface on the interior of the spacer. The outer alignment feature of the spacer may comprise a pair of ridges of different widths spaced on the exterior circumference of the spacer.

The tube surrounding the electrode may be an assembly comprising insulating tubing, a heat-resistant tip adjacent to a distal end of the insulating tubing, a stiffening element over a joint between the insulating tubing and the heat-resistant tip and shrink wrap over a portion of the insulating tubing, the heat-resistant tip and the stiffening element. In an alternate embodiment, the tube The grip may comprise a collar having a plurality of depressions.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIG. 1A is a first side view of a multi-functional electrosurgical plasma accessory in accordance with a preferred embodiment of the present invention.

FIG. 1B is a top view of a multi-functional electrosurgical plasma accessory in accordance with a preferred embodiment of the present invention.

FIG. 1E is a rear view of a multi-functional electrosurgical plasma accessory in accordance with a preferred embodiment of the present invention.

FIG. 1F is a front view of a multi-functional electrosurgical plasma accessory in accordance with a preferred embodiment of the present invention.

FIG. 2A is a front perspective view of an extendable probe assembly of a multi-functional electrosurgical plasma accessory in accordance with a preferred embodiment of the present invention in a retracted position such that the electrode is exposed at the tip of the probe.

FIG. 2B is a front perspective view of an extendable probe assembly of a multi-functional electrosurgical plasma accessory in accordance with a preferred embodiment of the present invention in an extended position such that the electrode does not extend outside of the tip of the probe.

FIG. 2C is a first side view of an extendable probe assembly of a multi-functional electrosurgical plasma accessory in accordance with a preferred embodiment of the present invention in a retracted position.

FIG. 2D is a second side view of an extendable probe assembly of a multi-functional electrosurgical plasma accessory in accordance with a preferred embodiment of the present invention in a retracted position.

FIG. 2E is a front end view of an extendable probe assembly of a multi-functional electrosurgical plasma accessory in accordance with a preferred embodiment of the present invention.

FIG. 2F is a first side view of an extendable probe assembly of a multi-functional electrosurgical plasma accessory in accordance with a preferred embodiment of the present invention in an extended position.

FIG. 2G is a second side view of an extendable probe assembly of a multi-functional electrosurgical plasma accessory in accordance with a preferred embodiment of the present invention in an extended position.

FIG. 4A is a first side view of a shaft of an extendable probe assembly of a multi-functional electrosurgical plasma accessory in accordance with a preferred embodiment of the present invention.

FIG. 4B is a second side view of a shaft of an extendable probe assembly of a multi-functional electrosurgical plasma accessory in accordance with a preferred embodiment of the present invention.

FIG. 4C is an end view of a shaft of an extendable probe assembly of a multi-functional electrosurgical plasma accessory in accordance with a preferred embodiment of the present invention.

FIG. 8A is a top view of a bottom portion of a handpiece of an extendable probe assembly of a multi-functional electrosurgical plasma accessory in accordance with a preferred embodiment of the present invention.

FIG. 8B is a side view of a bottom portion of a handpiece of an extendable probe assembly of a multi-functional electrosurgical plasma accessory in accordance with a preferred embodiment of the present invention.

FIG. 8C is a bottom view of a bottom portion of a handpiece of an extendable probe assembly of a multi-functional electrosurgical plasma accessory in accordance with a preferred embodiment of the present invention.

FIG. 8D is a front view of a bottom portion of a handpiece of an extendable probe assembly of a multi-functional electrosurgical plasma accessory in accordance with a preferred embodiment of the present invention.

FIG. 9B is a perspective view of buttons and PCB board of a handpiece of an extendable probe assembly of a multi-functional electrosurgical plasma accessory in accordance with a preferred embodiment of the present invention.

FIG. 10A is a side view of a connector of a handpiece of an extendable probe assembly of a multi-functional electrosurgical plasma accessory in accordance with a preferred embodiment of the present invention.

FIG. 10B is a rear end view of a connector of a handpiece of an extendable probe assembly of a multi-functional electrosurgical plasma accessory in accordance with a preferred embodiment of the present invention.

FIG. 10C is a front perspective view of a connector of a handpiece of an extendable probe assembly of a multi-functional electrosurgical plasma accessory in accordance with a preferred embodiment of the present invention.

FIG. 10D is a rear perspective view of a connector of a handpiece of an extendable probe assembly of a multi-functional electrosurgical plasma accessory in accordance with a preferred embodiment of the present invention.

FIG. 12C is a first side view of an extendable probe assembly of a multi-functional electrosurgical plasma accessory in accordance with a second preferred embodiment of the present invention in a retracted position.

FIG. 12D is a second side view of an extendable probe assembly of a multi-functional electrosurgical plasma accessory in accordance with a second preferred embodiment of the present invention in a retracted position.

FIG. 12E is a front end view of an extendable probe assembly of a multi-functional electrosurgical plasma accessory in accordance with a second preferred embodiment of the present invention.

FIG. 12F is a first side view of an extendable probe assembly of a multi-functional electrosurgical plasma accessory in accordance with a second preferred embodiment of the present invention in an extended position.

FIG. 12G is a second side view of an extendable probe assembly of a multi-functional electrosurgical plasma accessory in accordance with a second preferred embodiment of the present invention in an extended position.

FIG. 16D is a top view of a top portion of a handpiece of an extendable probe assembly of a multi-functional electrosurgical plasma accessory in accordance with a second preferred embodiment of the present invention.

FIG. 16E is a first side view of a top portion of a handpiece of an extendable probe assembly of a multi-functional electrosurgical plasma accessory in accordance with a second preferred embodiment of the present invention.

FIG. 16F is a bottom view of a top portion of a handpiece of an extendable probe assembly of a multi-functional electrosurgical plasma accessory in accordance with a second preferred embodiment of the present invention.

FIG. 16G is a second side view of a top portion of a handpiece of an extendable probe assembly of a multi-functional electrosurgical plasma accessory in accordance with a second preferred embodiment of the present invention.

FIG. 16H is a rear view of a top portion of a handpiece of an extendable probe assembly of a multi-functional electrosurgical plasma accessory in accordance with a second preferred embodiment of the present invention.

FIG. 16I is a front view of a top portion of a handpiece of an extendable probe assembly of a multi-functional electrosurgical plasma accessory in accordance with a second preferred embodiment of the present invention.

FIG. 16J is a top front perspective view of a top portion of a handpiece of an extendable probe assembly of a multi-functional electrosurgical plasma accessory in accordance with a second preferred embodiment of the present invention.

FIG. 16K is a bottom rear perspective view of a top portion of a handpiece of an extendable probe assembly of a multi-functional electrosurgical plasma accessory in accordance with a second preferred embodiment of the present invention.

FIG. 16L is a bottom perspective view of a top portion of a handpiece of an extendable probe assembly of a multi-functional electrosurgical plasma accessory in accordance with a second preferred embodiment of the present invention.

FIG. 17A is a top view of a bottom portion of a handpiece of an extendable probe assembly of a multi-functional electrosurgical plasma accessory in accordance with a second preferred embodiment of the present invention.

FIG. 17B is a side view of a bottom portion of a handpiece of an extendable probe assembly of a multi-functional electrosurgical plasma accessory in accordance with a second preferred embodiment of the present invention.

FIG. 17C is a bottom view of a bottom portion of a handpiece of an extendable probe assembly of a multi-functional electrosurgical plasma accessory in accordance with a second preferred embodiment of the present invention.

FIG. 17D is a front view of a bottom portion of a handpiece of an extendable probe assembly of a multi-functional electrosurgical plasma accessory in accordance with a second preferred embodiment of the present invention.

DETAILED DESCRIPTION OF THE PREFERRED EMBODIMENTS

Figure 1C:
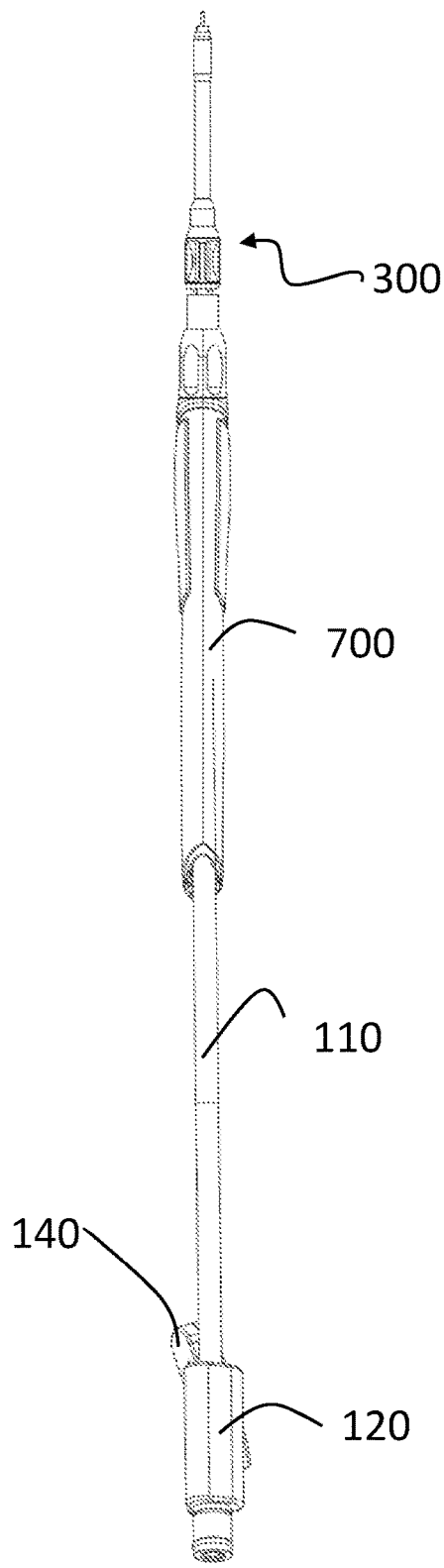
FIG. 1C is a bottom view of a multi-functional electrosurgical plasma accessory in accordance with a preferred embodiment of the present invention.
Figure 1D:
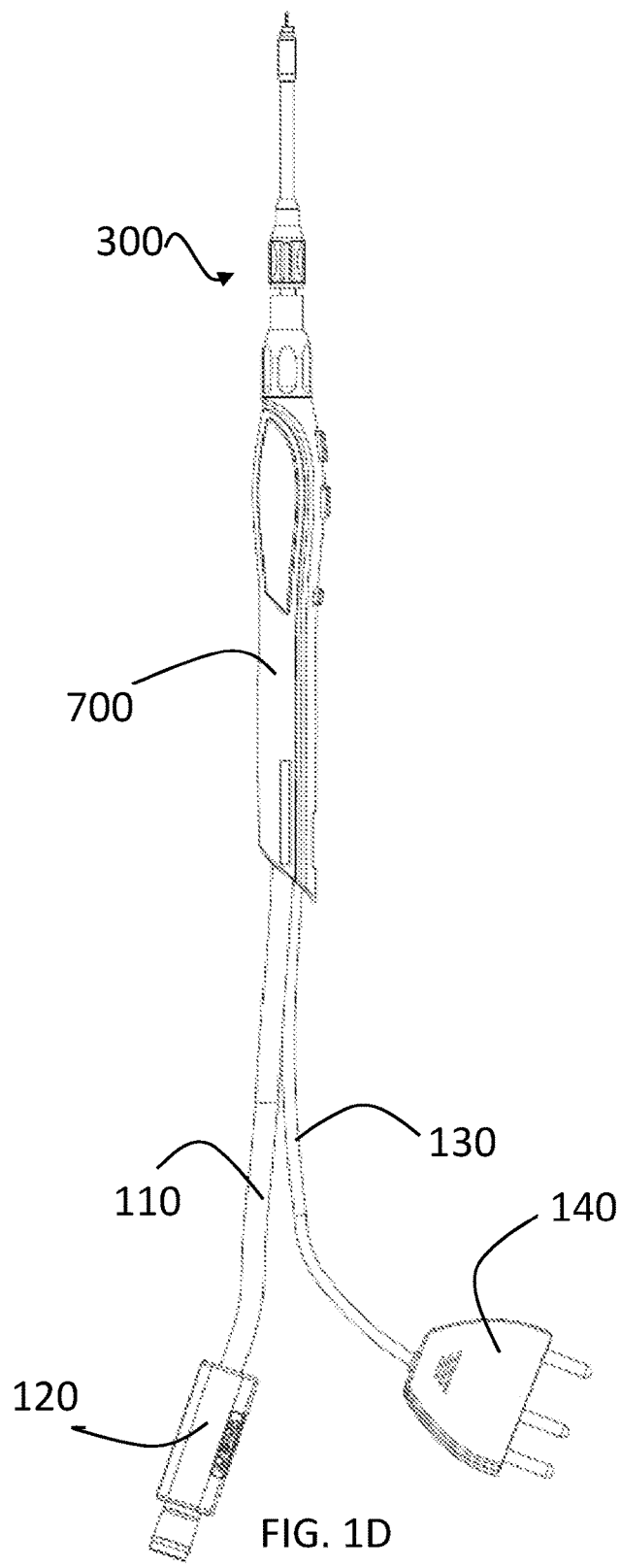
FIG. 1D is a second side view of a multi-functional electrosurgical plasma accessory in accordance with a preferred embodiment of the present invention.
Figure 1G:
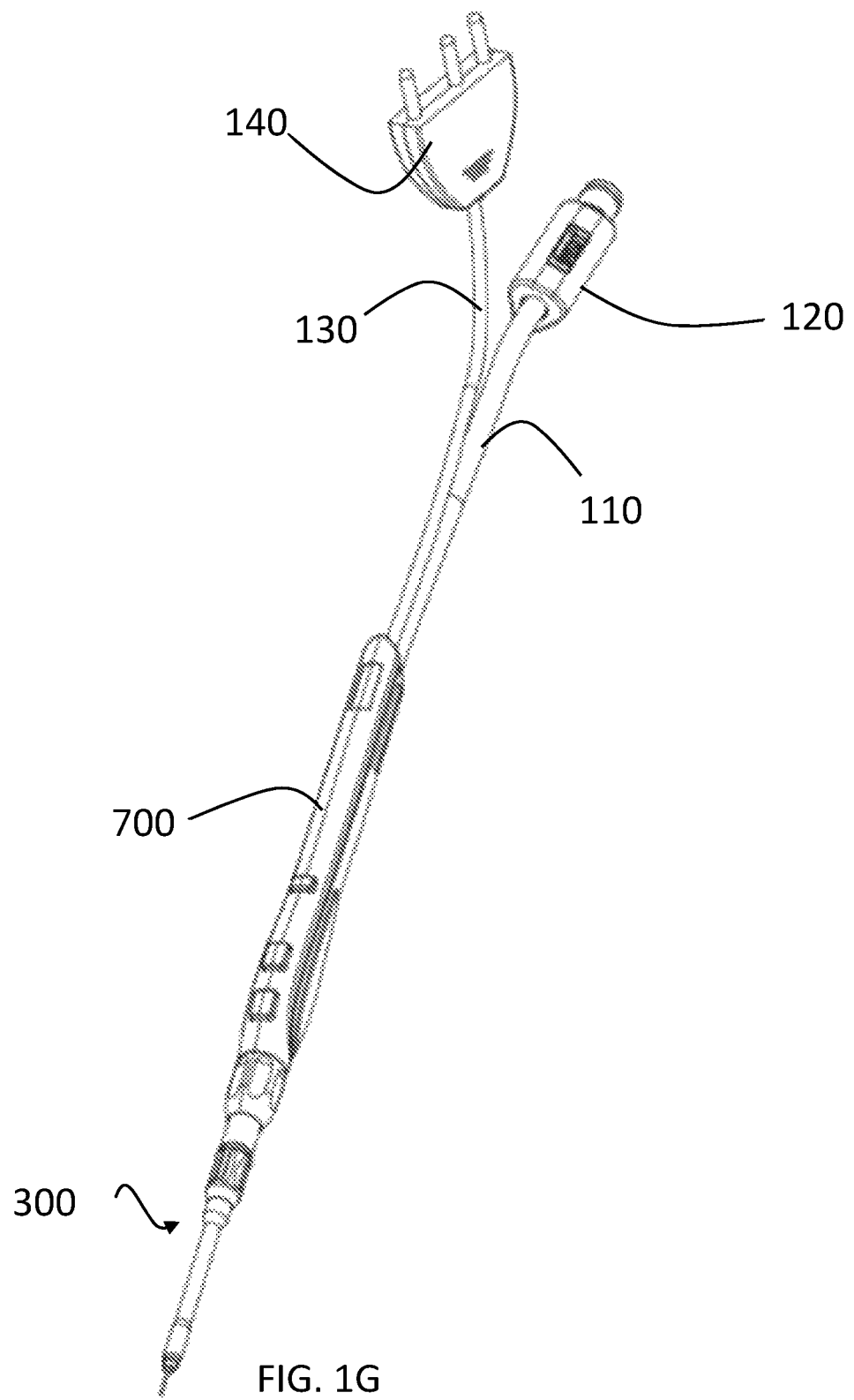
FIG. 1G is a perspective view of a multi-functional electrosurgical plasma accessory in accordance with a preferred embodiment of the present invention.

A multi-functional electrosurgical plasma accessory in accordance with a preferred embodiment of the present invention is described with reference the drawings. In FIGS. 1A-1G the electrosurgical attachment 100 has a handpiece 700, a gas supply tube 110 extending from the proximal end of the handpiece 700, a connector 120 for connecting the gas supply tube 110 to a source of gas (not shown), an electrical line 130 extending from the proximal end of the handpiece 700, a connector 140 for connecting the electrical line to an electrosurgical generators and an extendable probe 300 connected to the distal end of the handpiece 700.

Figures 2H, 2I:
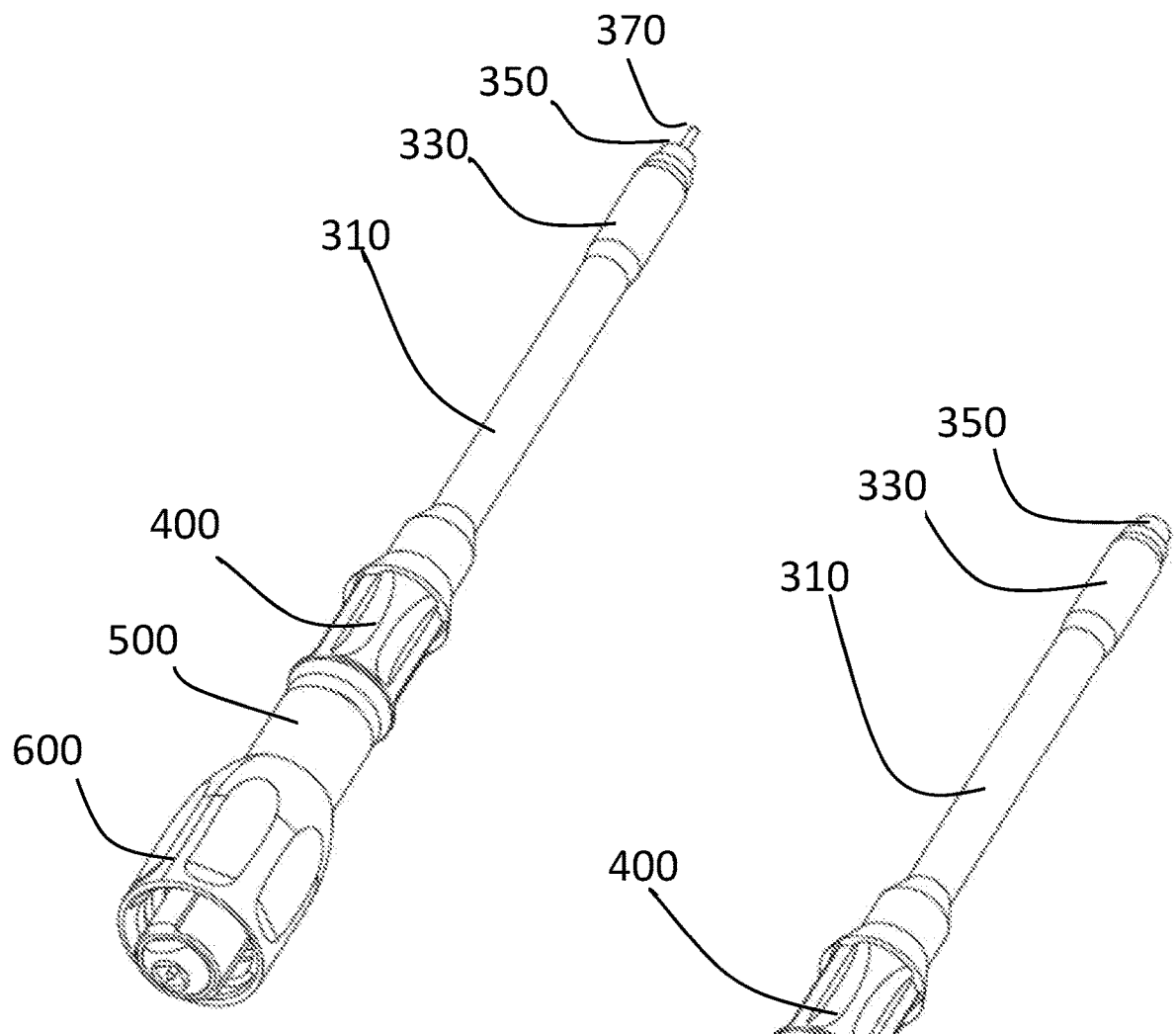
FIG. 2H is a rear perspective view of an extendable probe assembly of a multi-functional electrosurgical plasma accessory in accordance with a preferred embodiment of the present invention in a retracted position.
FIG. 2I is a rear perspective view of an extendable probe assembly of a multi-functional electrosurgical plasma accessory in accordance with a preferred embodiment of the present invention in an extended position.
Figure 2J:
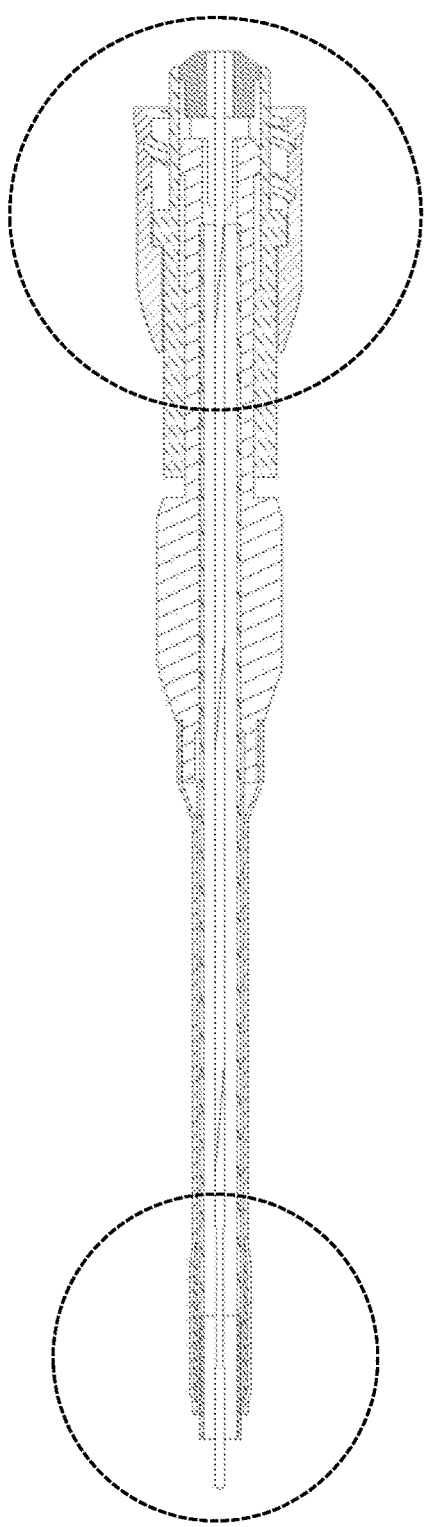
FIG. 2J is a first cross-sectional view of an extendable probe assembly of a multi-functional electrosurgical plasma accessory in accordance with a preferred embodiment of the present invention in a retracted position.
Figure 2K:
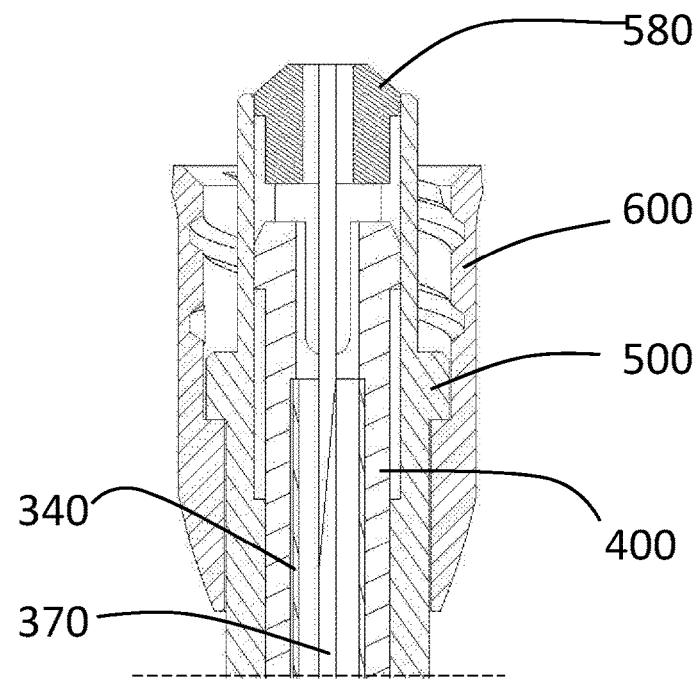
FIG. 2K is a close-up view of the proximal end of the first cross-sectional view shown in FIG. 2J.
Figure 2L:
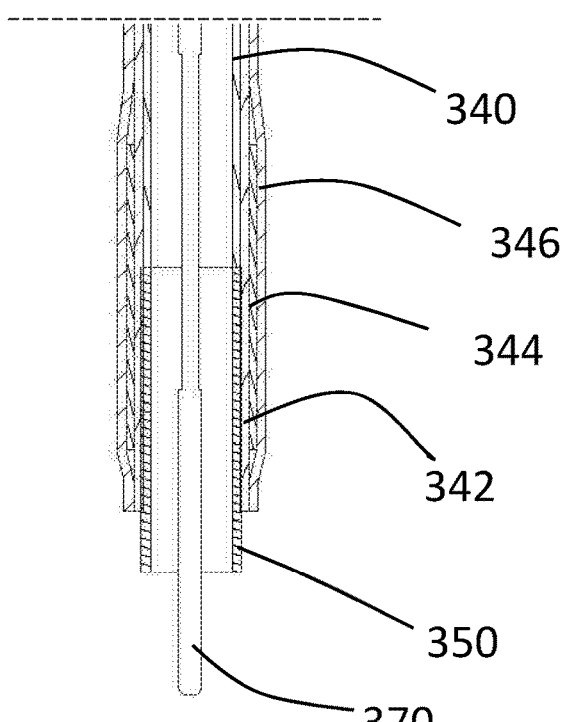
FIG. 2L is a close-up view of the distal end of the first cross-sectional view shown in FIG. 2J.
Figure 2M:
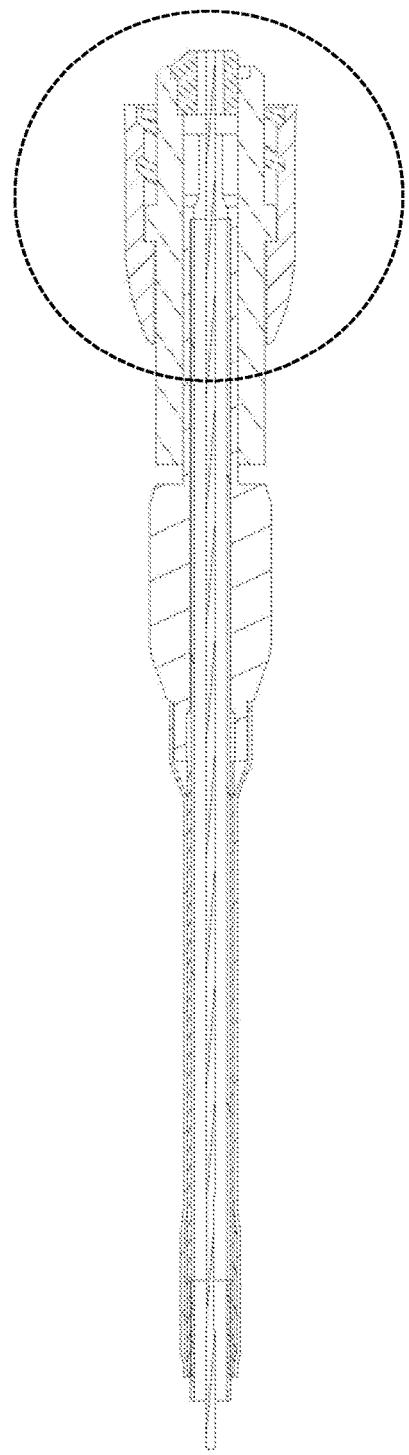
FIG. 2M is a second cross-sectional view of an extendable probe assembly of a multi-functional electrosurgical plasma accessory in accordance with a preferred embodiment of the present invention in a retracted position.
Figure 2N:
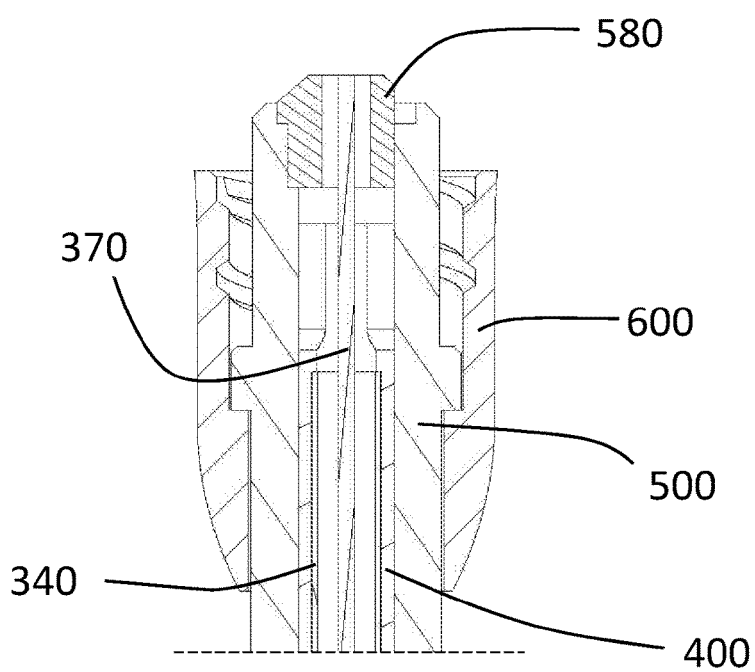
FIG. 2N is a close-up view of the proximal end of the second cross-sectional view shown in FIG. 2M.
Figure 3A:
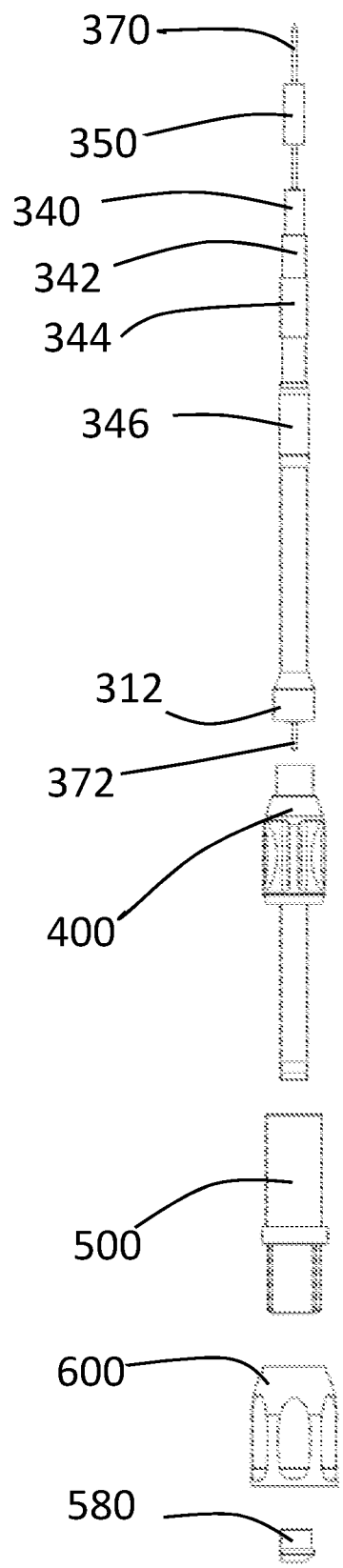
FIG. 3A is a first side view assembly drawing of an extendable probe assembly of a multi-functional electrosurgical plasma accessory in accordance with a preferred embodiment of the present invention.
Figure 3B:
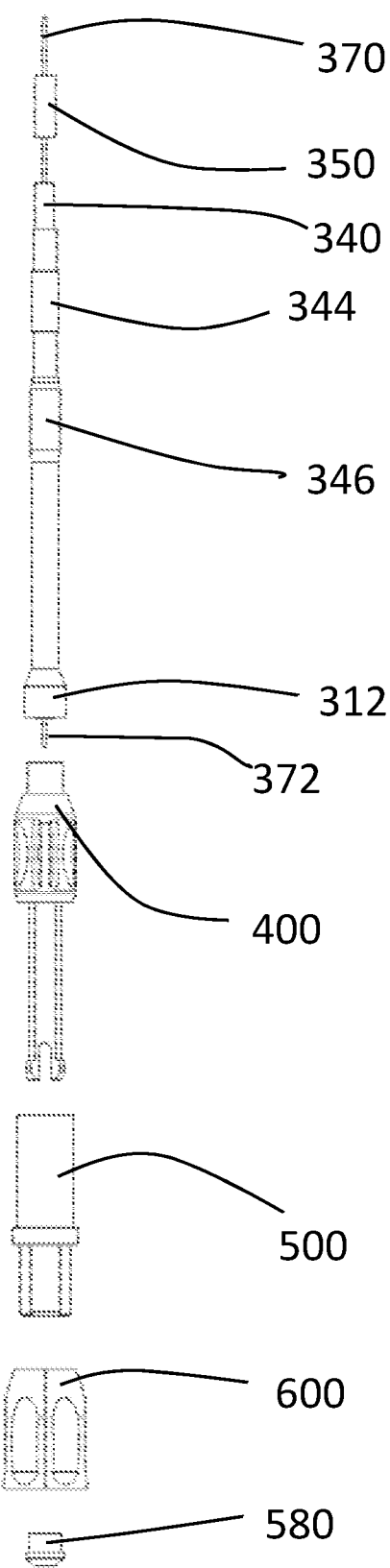
FIG. 3B is a second side view assembly drawing of an extendable probe assembly of a multi-functional electrosurgical plasma accessory in accordance with a preferred embodiment of the present invention.
Figure 3C:
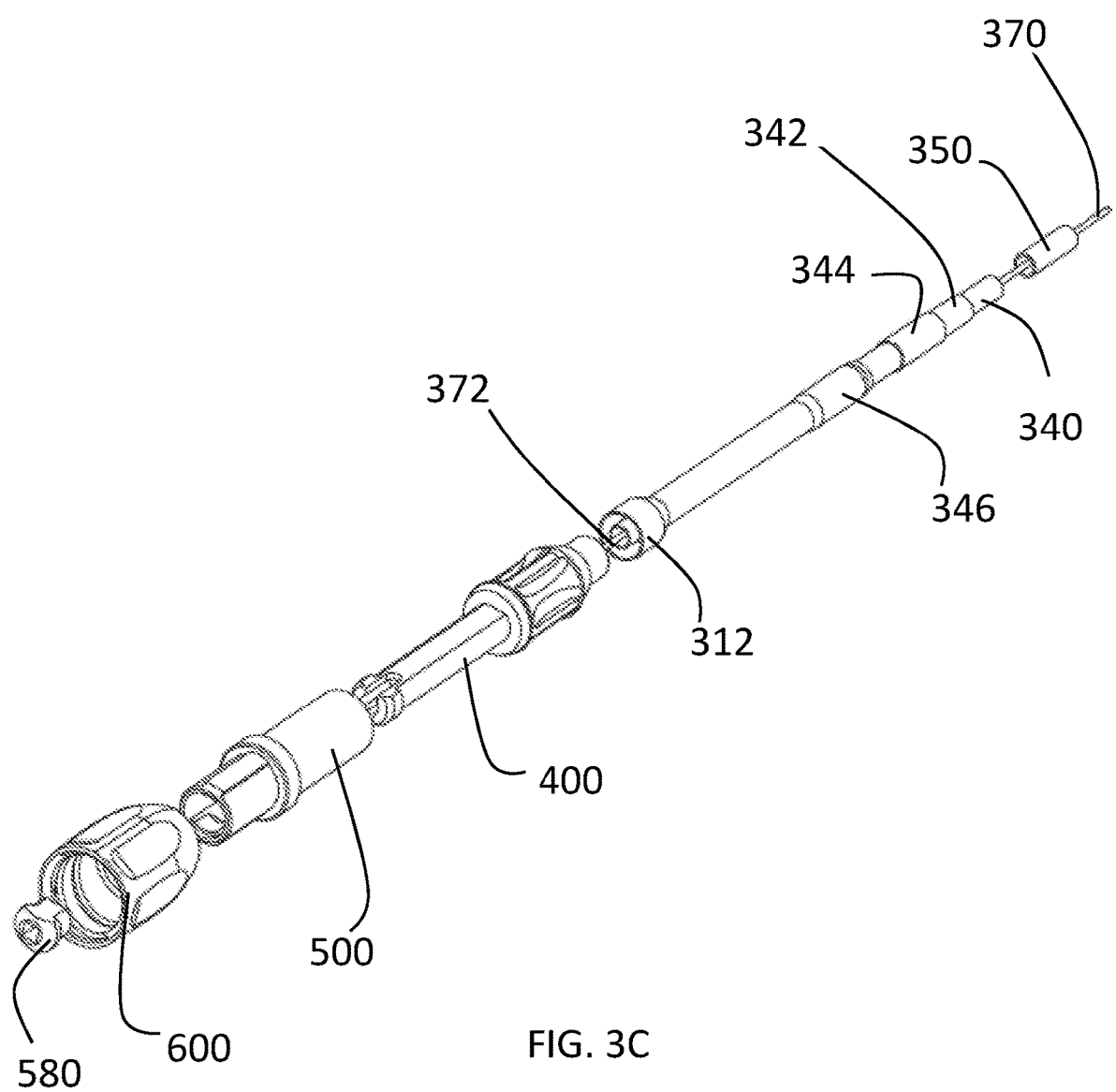
FIG. 3C is a rear perspective view assembly drawing of an extendable probe assembly of a multi-functional electrosurgical plasma accessory in accordance with a preferred embodiment of the present invention.
Figure 3D:
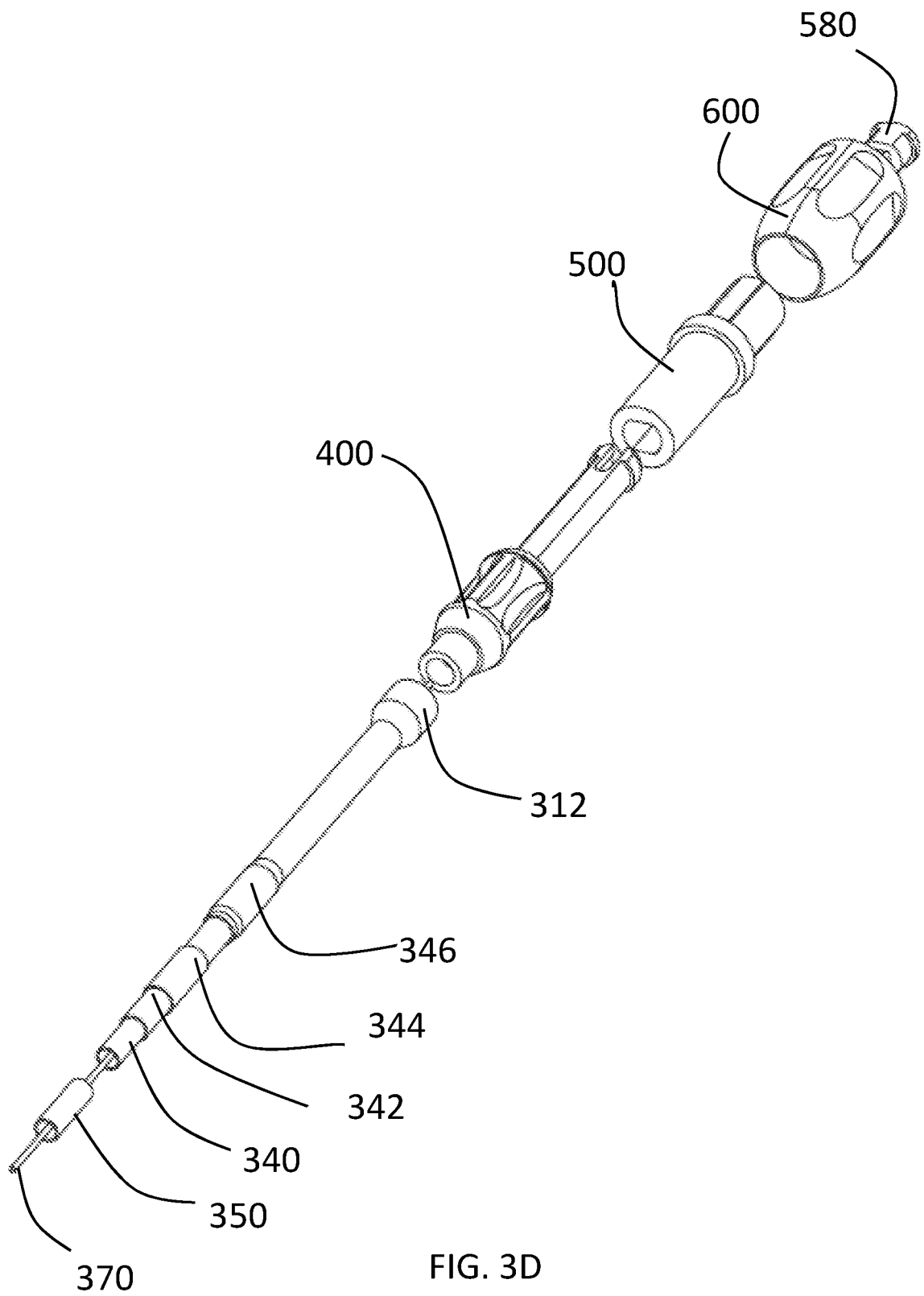
FIG. 3D is a front perspective view assembly drawing of an extendable probe assembly of a multi-functional electrosurgical plasma accessory in accordance with a preferred embodiment of the present invention.
Figure 4D:
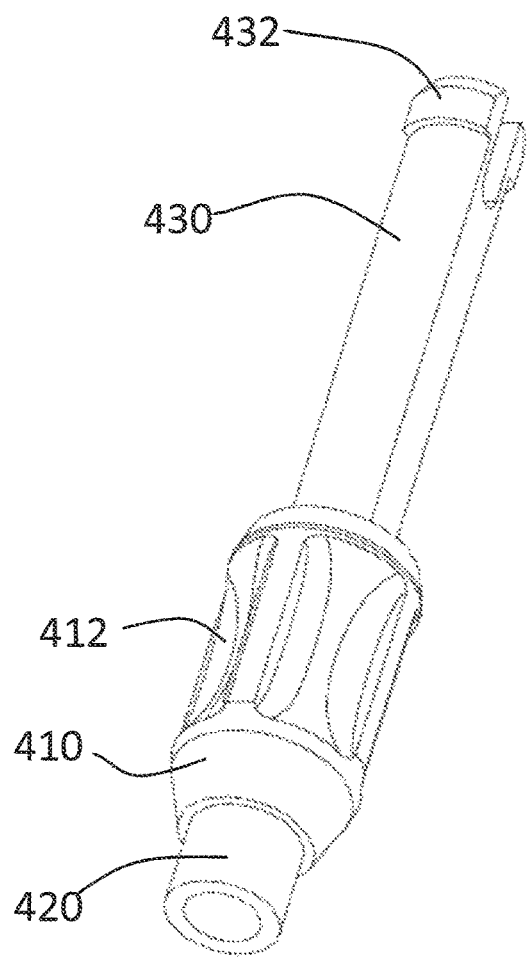
FIG. 4D is a front perspective view of a shaft of an extendable probe assembly of a multi-functional electrosurgical plasma accessory in accordance with a preferred embodiment of the present invention.
Figure 4E:
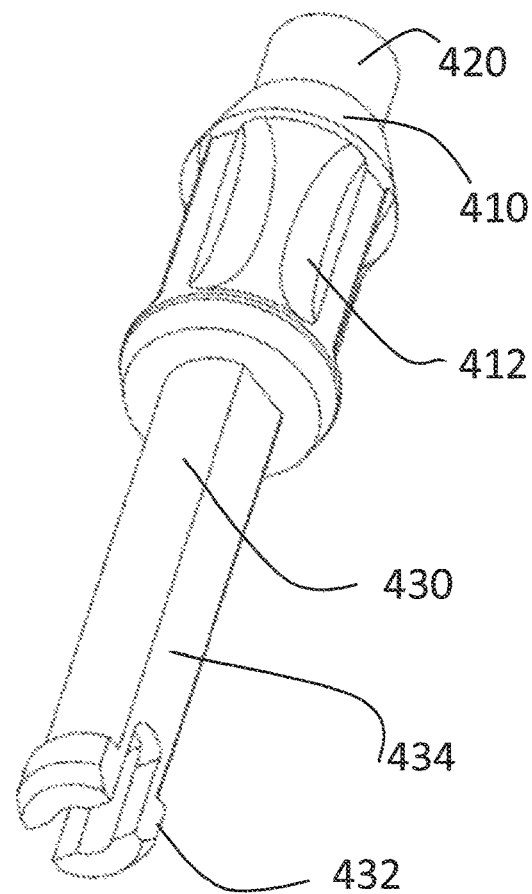
FIG. 4E is a rear perspective view of a shaft of an extendable probe assembly of a multi-functional electrosurgical plasma accessory in accordance with a preferred embodiment of the present invention.
Figure 4F:
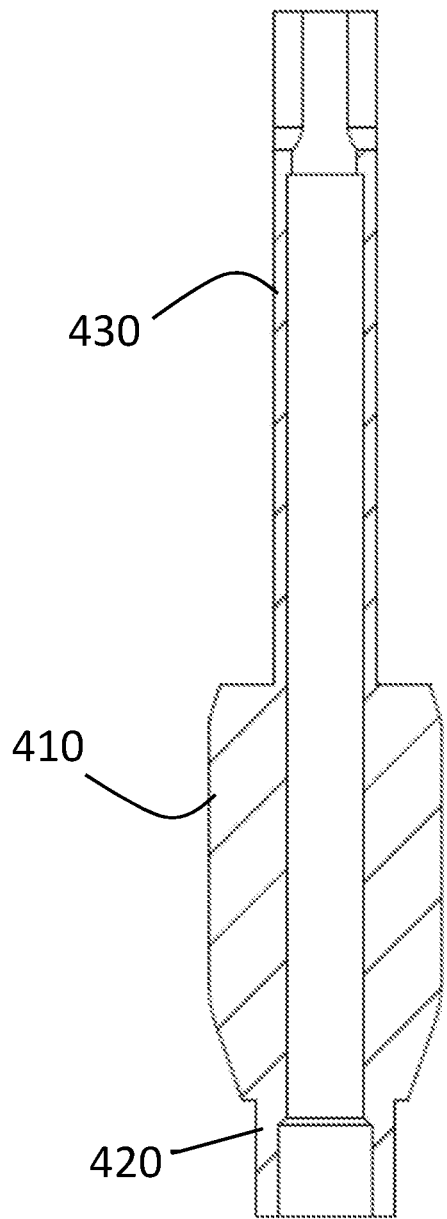
FIG. 4F is a first cross-section view of a shaft of an extendable probe assembly of a multi-functional electrosurgical plasma accessory in accordance with a preferred embodiment of the present invention.
Figure 4G:
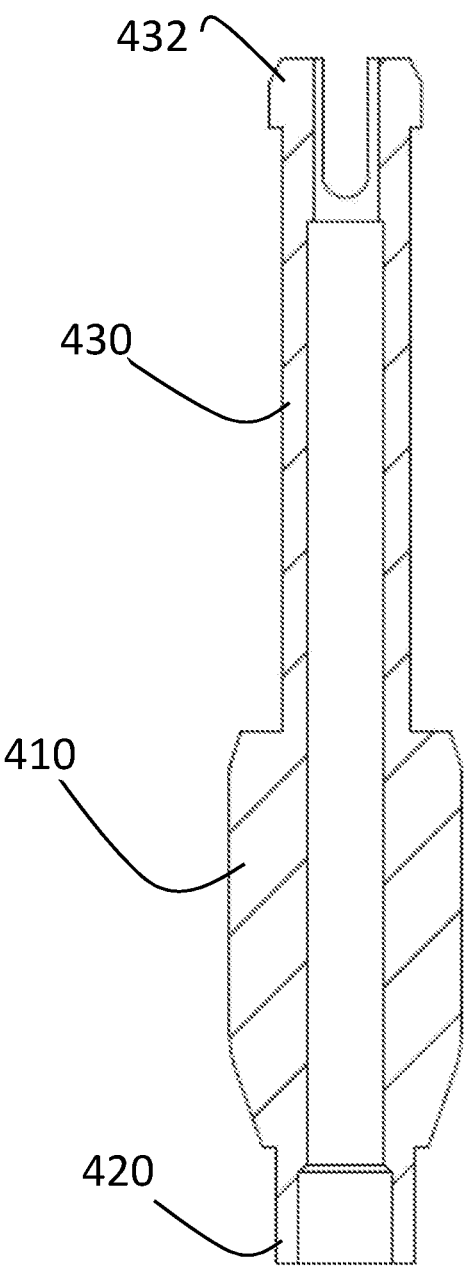
FIG. 4G is a second cross-section view of a shaft of an extendable probe assembly of a multi-functional electrosurgical plasma accessory in accordance with a preferred embodiment of the present invention.
Figures 5A, 5B, 5C:
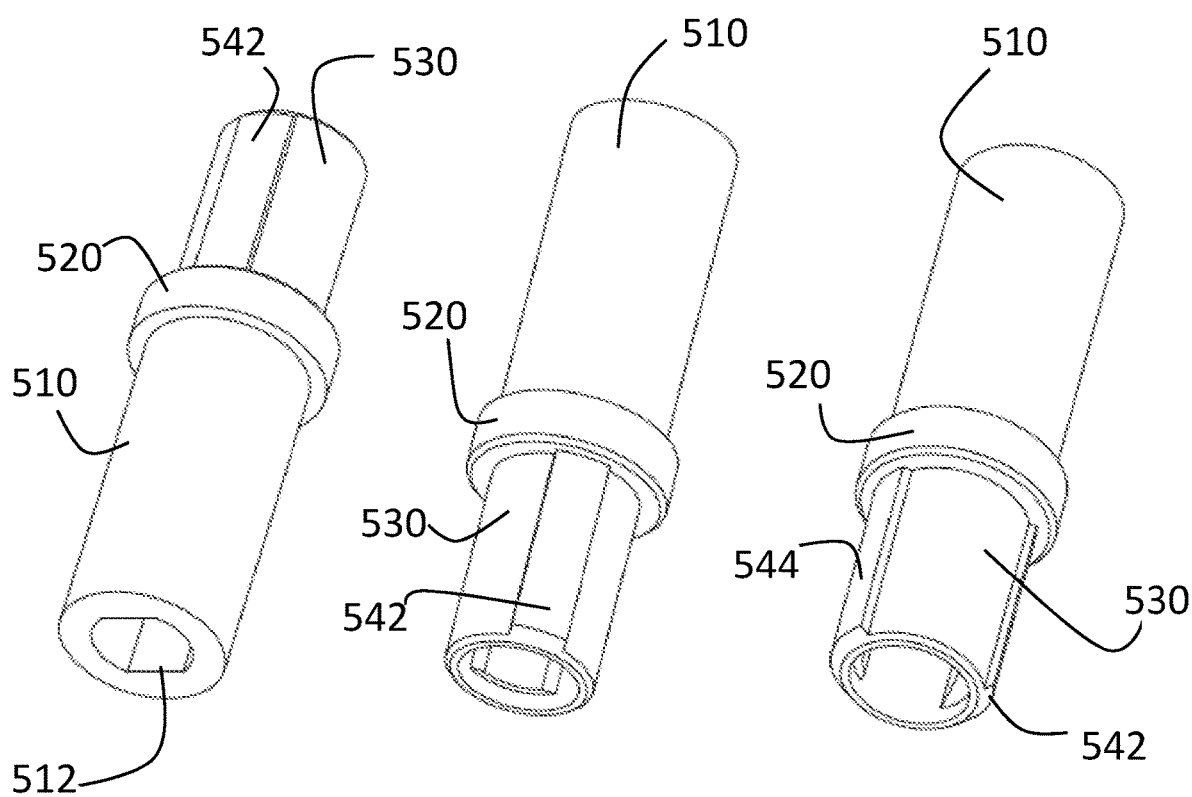
FIG. 5A is a first perspective view of a shaft of a keyed cylinder of an extendable probe assembly of a multi-functional electrosurgical plasma accessory in accordance with a preferred embodiment of the present invention.
FIG. 5B is a second perspective view of a shaft of a keyed cylinder of an extendable probe assembly of a multi-functional electrosurgical plasma accessory in accordance with a preferred embodiment of the present invention.
FIG. 5C is a third perspective view of a shaft of a keyed cylinder of an extendable probe assembly of a multi-functional electrosurgical plasma accessory in accordance with a preferred embodiment of the present invention.
Figure 5F:
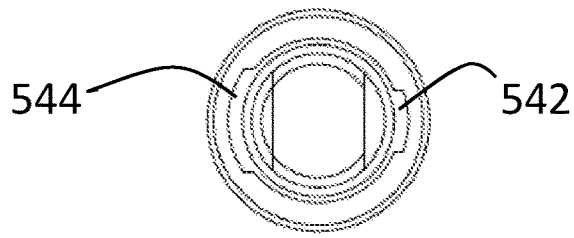
FIG. 5F is a first end view of a shaft of a keyed cylinder of an extendable probe assembly of a multi-functional electrosurgical plasma accessory in accordance with a preferred embodiment of the present invention.
Figure 5D:
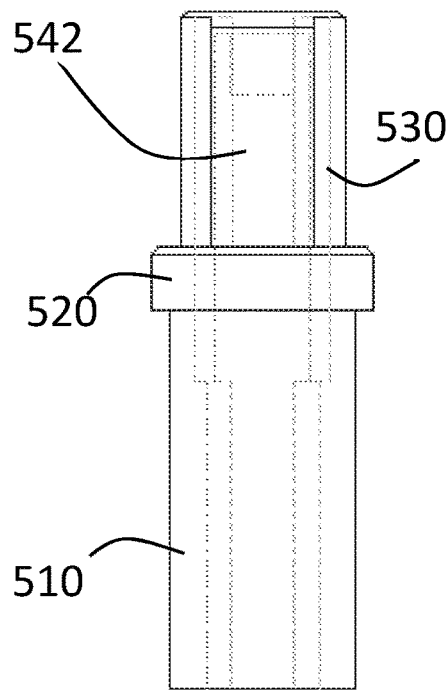
FIG. 5D is a first side view of a shaft of a keyed cylinder of an extendable probe assembly of a multi-functional electrosurgical plasma accessory in accordance with a preferred embodiment of the present invention.
Figure 5E:
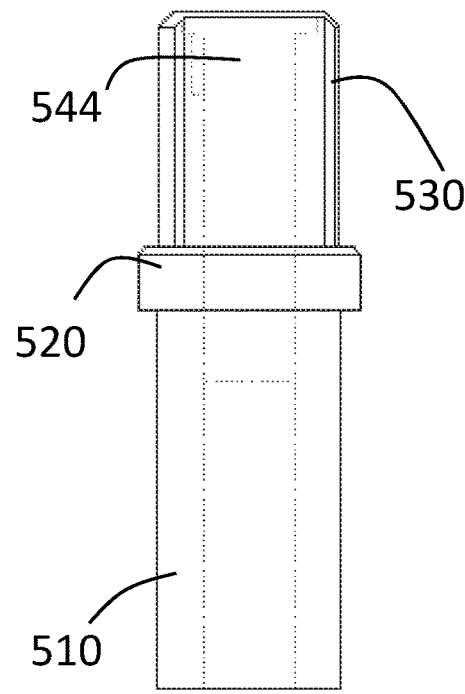
FIG. 5E is a second side view of a shaft of a keyed cylinder of an extendable probe assembly of a multi-functional electrosurgical plasma accessory in accordance with a preferred embodiment of the present invention.
Figure 5G:
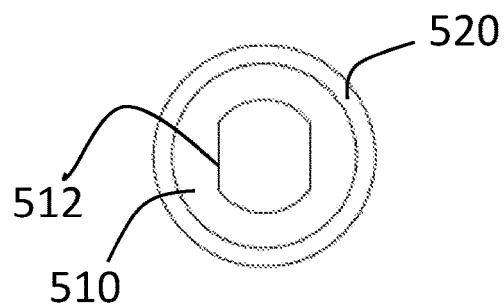
FIG. 5G is a second end view of a shaft of a keyed cylinder of an extendable probe assembly of a multi-functional electrosurgical plasma accessory in accordance with a preferred embodiment of the present invention.
Figure 5H:
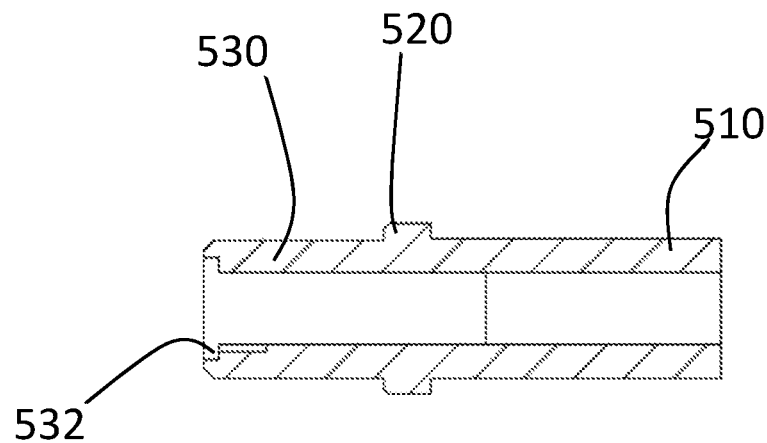
FIG. 5H is a first cross-sectional view of a shaft of a cylinder of an extendable probe assembly of a multi-functional electrosurgical plasma accessory in accordance with a preferred embodiment of the present invention.
Figure 5I:
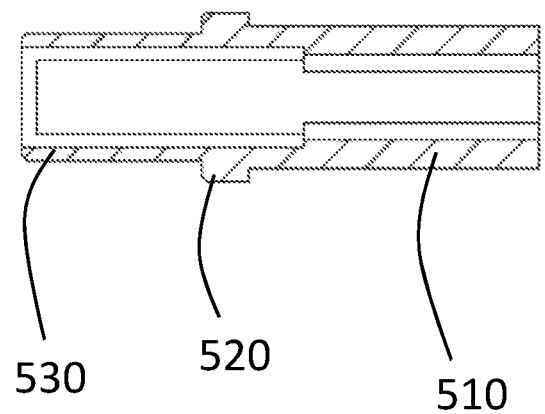
FIG. 5I is a second cross-sectional view of a shaft of a cylinder of an extendable probe assembly of a multi-functional electrosurgical plasma accessory in accordance with a preferred embodiment of the present invention.
Figure 6A:
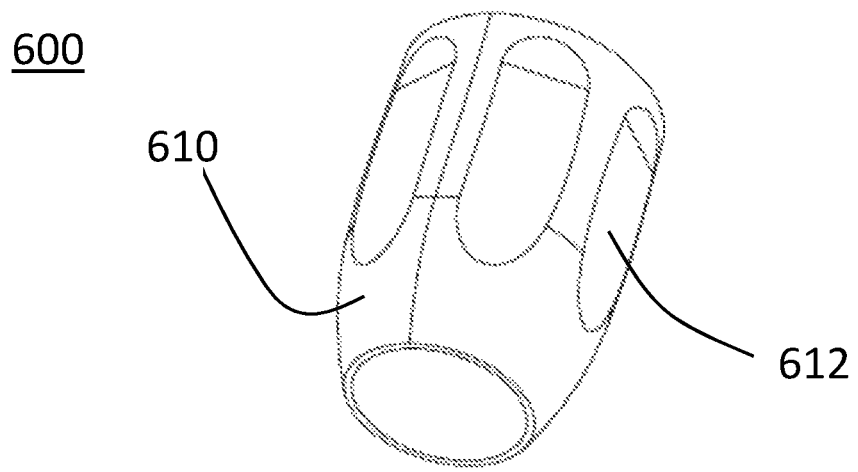
FIG. 6A is a front perspective view of a collet of an extendable probe assembly of a multi-functional electrosurgical plasma accessory in accordance with a preferred embodiment of the present invention.
Figure 6B:
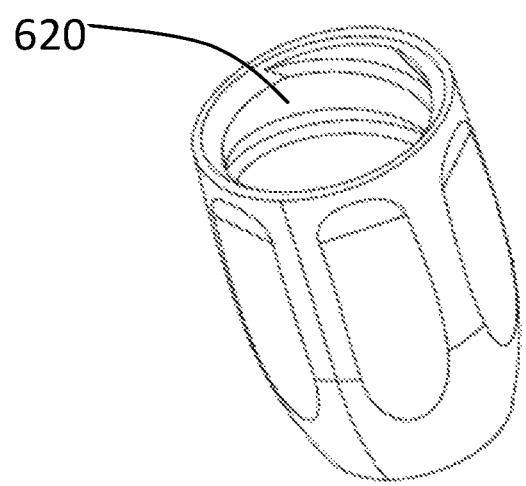
FIG. 6B is a rear perspective view of a collet of an extendable probe assembly of a multi-functional electrosurgical plasma accessory in accordance with a preferred embodiment of the present invention.
Figure 6D:
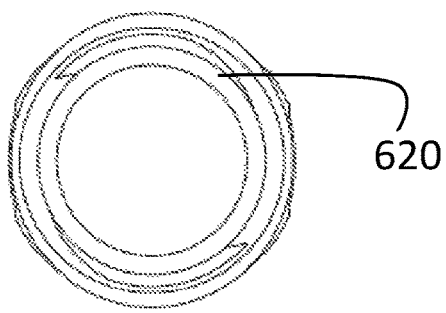
FIG. 6D is a rear end view of a collet of an extendable probe assembly of a multi-functional electrosurgical plasma accessory in accordance with a preferred embodiment of the present invention.
Figure 6C:
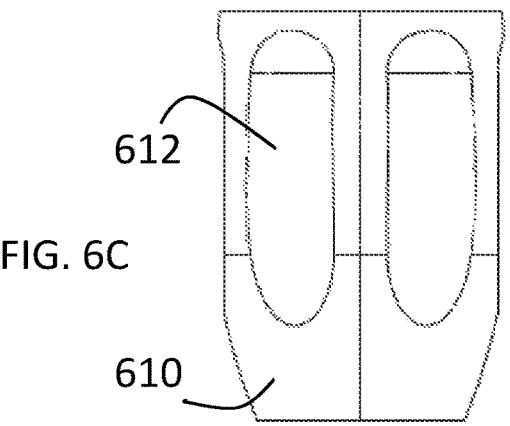
FIG. 6C is a first side view of a collet of an extendable probe assembly of a multi-functional electrosurgical plasma accessory in accordance with a preferred embodiment of the present invention.
Figure 6F:
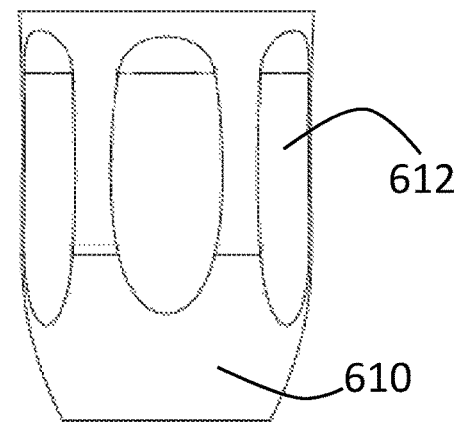
FIG. 6F is a second side view of a collet of an extendable probe assembly of a multi-functional electrosurgical plasma accessory in accordance with a preferred embodiment of the present invention.
Figure 6E:
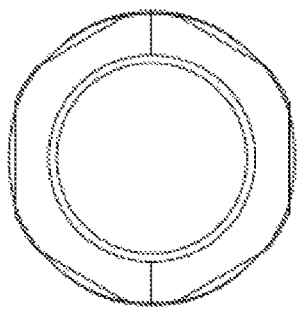
FIG. 6E is a front end view of a collet of an extendable probe assembly of a multi-functional electrosurgical plasma accessory in accordance with a preferred embodiment of the present invention.
Figure 6G:
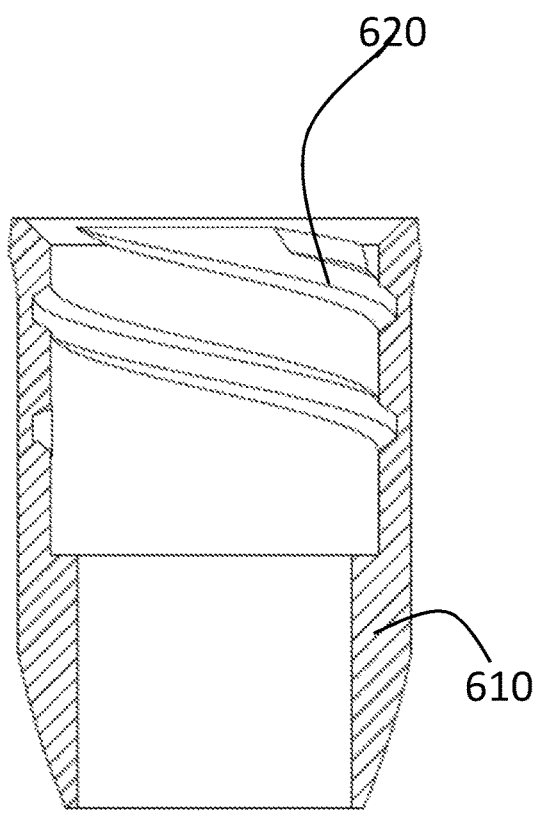
FIG. 6G is a first cross-sectional view of a collet of an extendable probe assembly of a multi-functional electrosurgical plasma accessory in accordance with a preferred embodiment of the present invention.
Figure 6H:
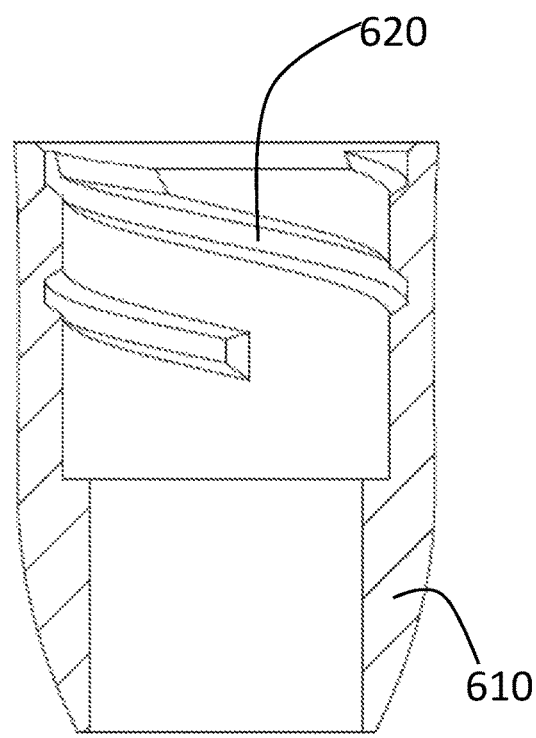
FIG. 6H is a second cross-sectional view of a collet of an extendable probe assembly of a multi-functional electrosurgical plasma accessory in accordance with a preferred embodiment of the present invention.

In accordance with a preferred embodiment, the extendable probe 300, shown in FIGS. 2A-6H, has a tip assembly connected to a shaft 400, a spacer 500 and a collet 600. The tip assembly has an electrode 370 extending through a tube 340 (see FIG. 2L), a heat resistant tip 350, a layer 342, such as an adhesion tube or insulating layer, over the heat-resistant tip 350 and the tube 340, a stiffening element 344 over the joint between the heat-resistant tip 350 and tube 340, and a shrink tube 346 over the rest of the tip assembly. The stiffening element 344 strengthens the joint between the heat-resistant tip 350 and tube 340 to prevent the tip assembly from bending at that joint.

The shaft 400, shown in FIGS. 4A-4G, has a collar or grip member 410 with a plurality of depressions or grooves 412 for gripping the shaft, a cylindrical neck 420, and an elongated portion 430 having a plurality of engagement tines 432. The elongated portion is predominantly cylindrical but has opposing flat sides 434 used for alignment with the spacer 500.

The spacer 500, shown in FIGS. 5A-5I, has a first cylindrical portion 510, an annular ridge 520 and a second cylindrical portion 530 having a pair of different-sized ridges 542, 544. The interior of the spacer 500 has a channel for receiving the elongated portion 430 of the shaft 400. At the end of the second cylindrical portion 530, the interior of the spacer 500 has a shoulder 532 for receiving metal contact 580. The channel has two flat sides 512 for aligning with the flat sides 434 in the elongated portion 430 of the shaft 400. While a shape of two rounded sides and two flat sides is shown here for alignment of the shaft 400 with the spacer 500, other alignments designs are well-known and may be used with the invention.

The collet 600, show in in FIGS. 6A-6H, has a body 610 having a plurality of depressions or dimples 612 on its exterior for gripping the collet. The interior of the collet 600 has threads 620 for engaging with threads on the handpiece 700.

Figure 7A:
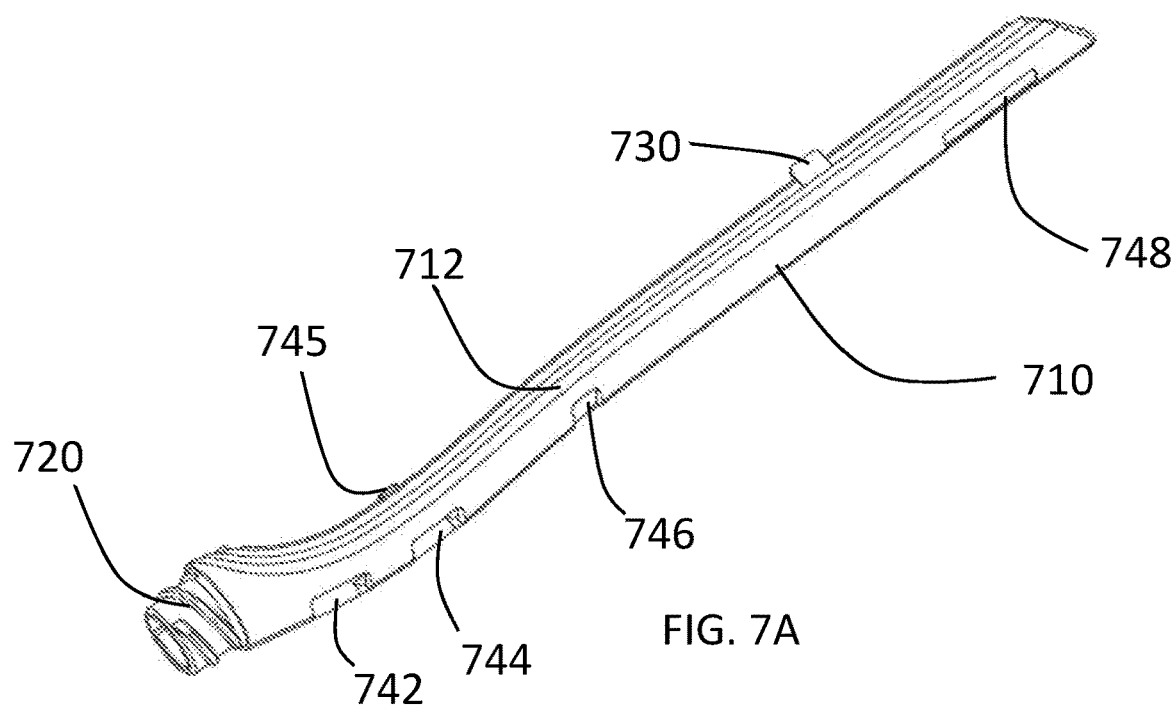
FIGS. 7A, 7B and 7C are perspective views of a top portion of a handpiece of an extendable probe assembly of a multi-functional electrosurgical plasma accessory in accordance with a preferred embodiment of the present invention.
Figure 7B:
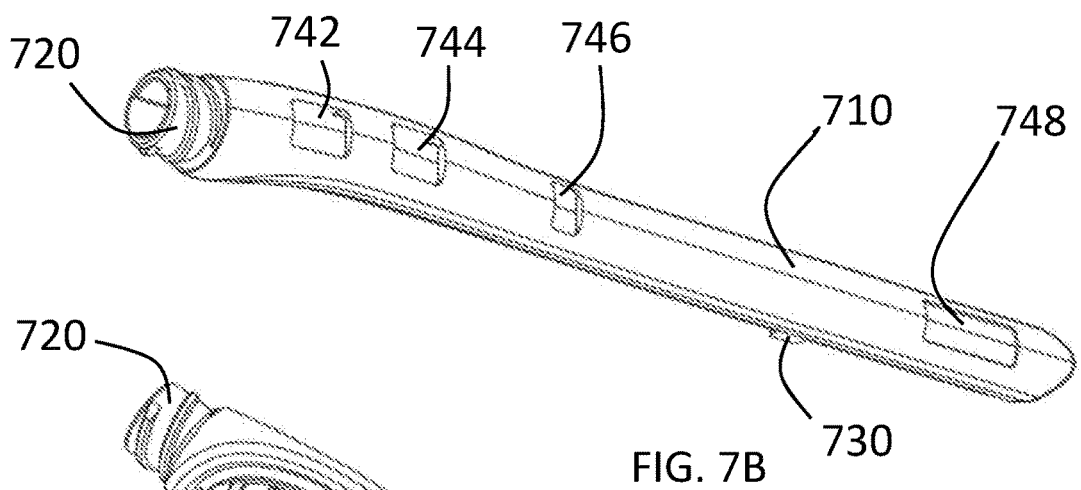
Figure 7C:
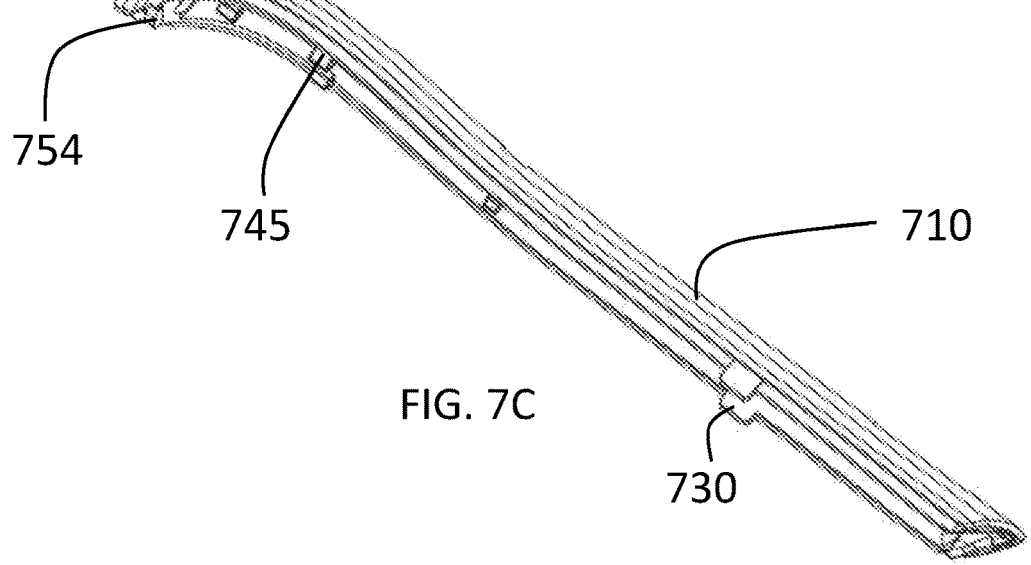
Figure 7D:
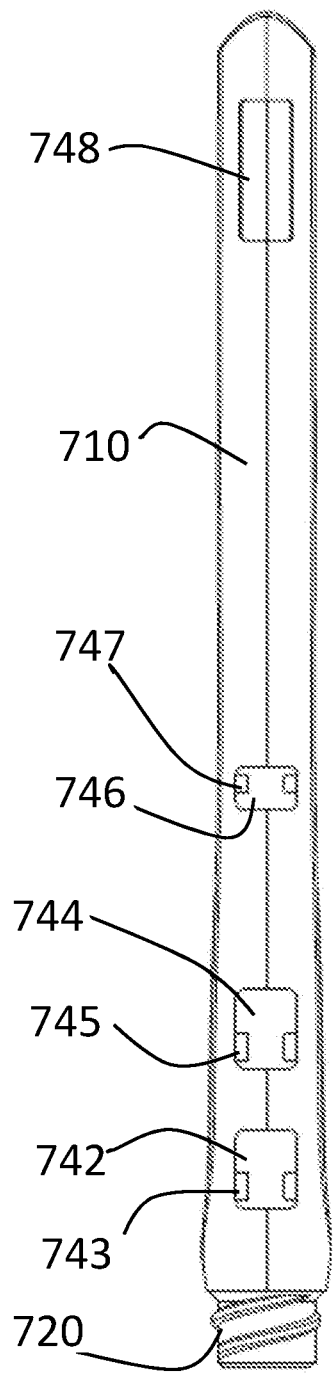
FIG. 7D is a top view of a top portion of a handpiece of an extendable probe assembly of a multi-functional electrosurgical plasma accessory in accordance with a preferred embodiment of the present invention.
Figure 7E:
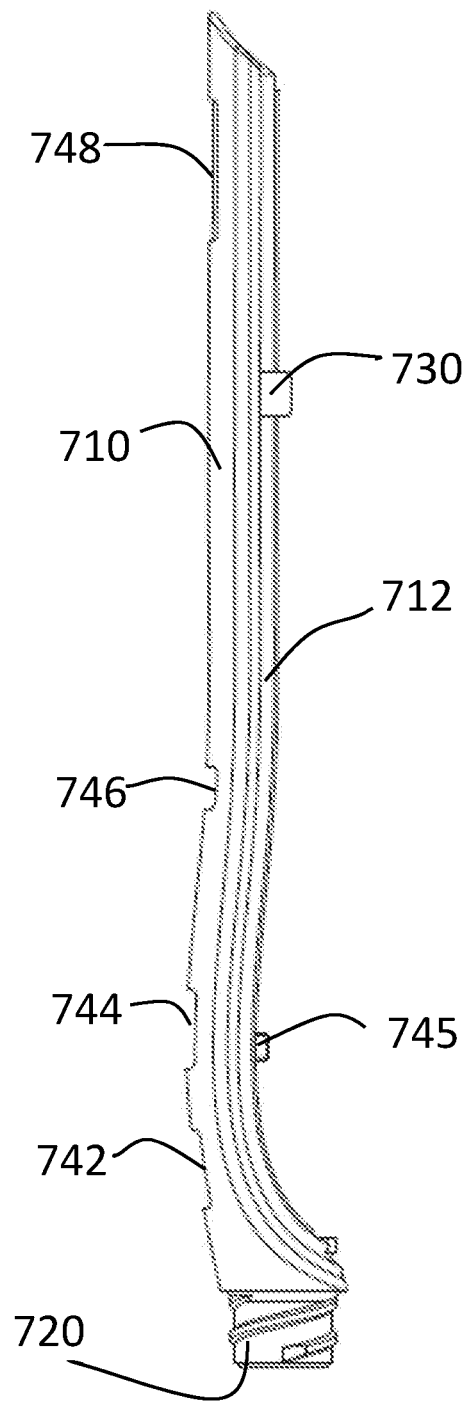
FIG. 7E is a first side view of a top portion of a handpiece of an extendable probe assembly of a multi-functional electrosurgical plasma accessory in accordance with a preferred embodiment of the present invention.
Figures 7F, 7G:
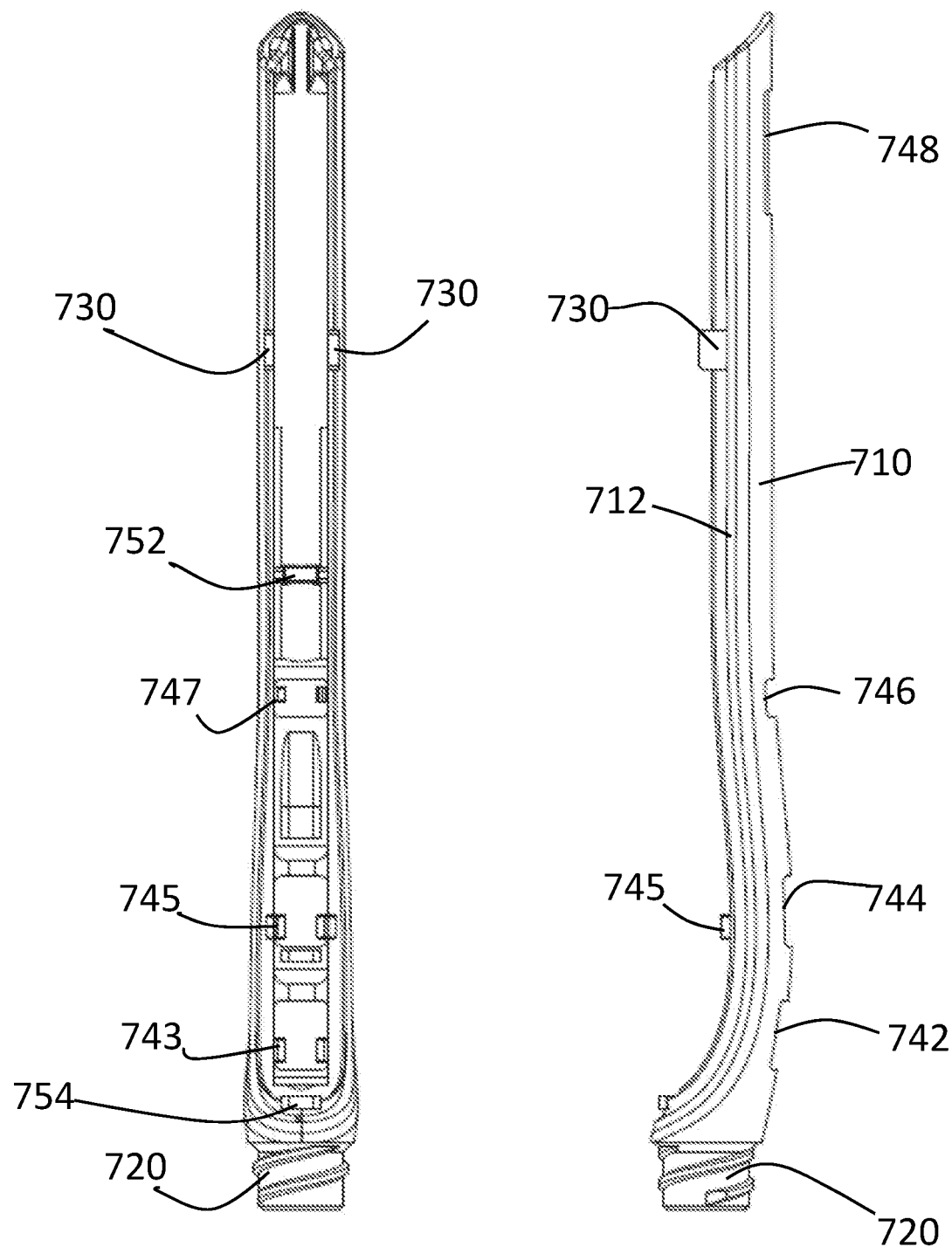
FIG. 7F is a bottom view of a top portion of a handpiece of an extendable probe assembly of a multi-functional electrosurgical plasma accessory in accordance with a preferred embodiment of the present invention.
FIG. 7G is a second side view of a top portion of a handpiece of an extendable probe assembly of a multi-functional electrosurgical plasma accessory in accordance with a preferred embodiment of the present invention.
Figure 7H:
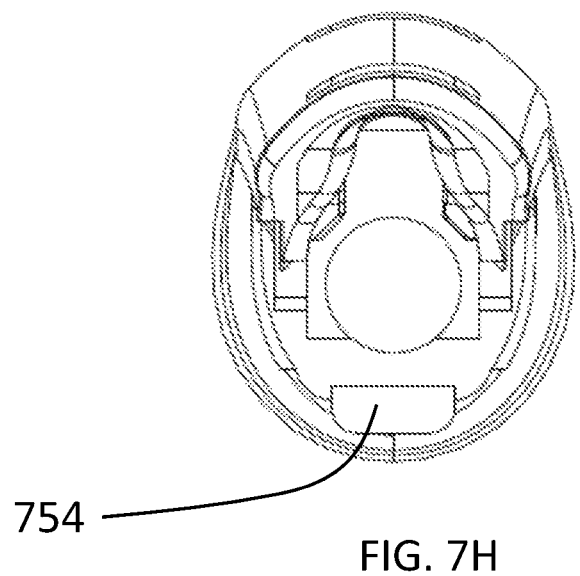
FIG. 7H is a rear view of a top portion of a handpiece of an extendable probe assembly of a multi-functional electrosurgical plasma accessory in accordance with a preferred embodiment of the present invention.
Figure 7I:
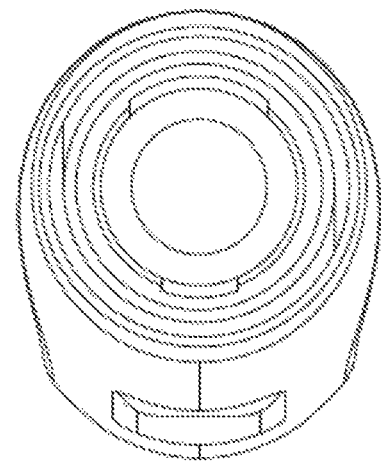
FIG. 7I is a front view of a top portion of a handpiece of an extendable probe assembly of a multi-functional electrosurgical plasma accessory in accordance with a preferred embodiment of the present invention.
Figures 7J, 7K:
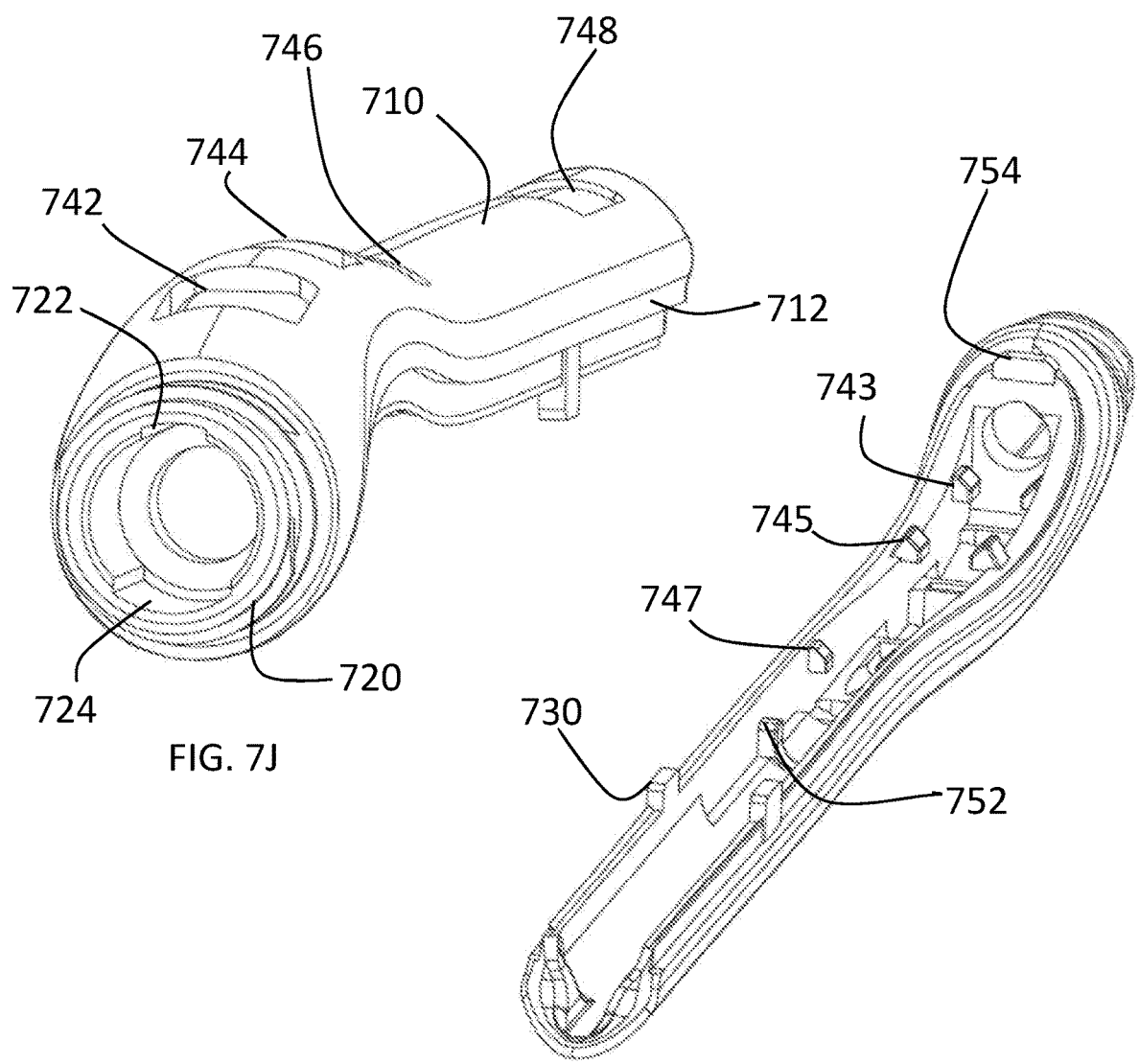
FIG. 7J is a top front perspective view of a top portion of a handpiece of an extendable probe assembly of a multi-functional electrosurgical plasma accessory in accordance with a preferred embodiment of the present invention.
FIG. 7K is a bottom rear perspective view of a top portion of a handpiece of an extendable probe assembly of a multi-functional electrosurgical plasma accessory in accordance with a preferred embodiment of the present invention.
Figure 7L:
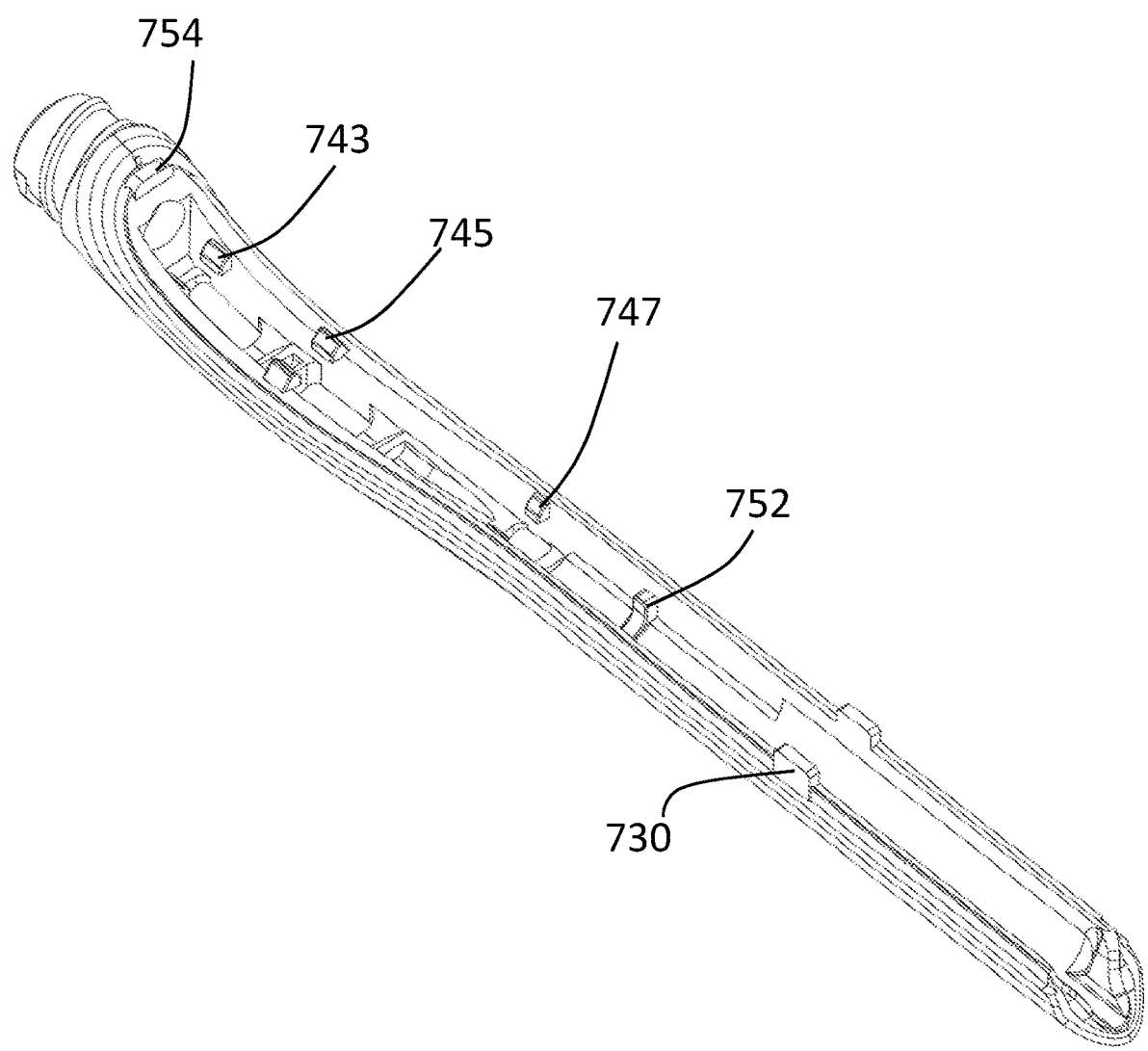
FIG. 7L is a bottom perspective view of a top portion of a handpiece of an extendable probe assembly of a multi-functional electrosurgical plasma accessory in accordance with a preferred embodiment of the present invention.
Figure 8E:
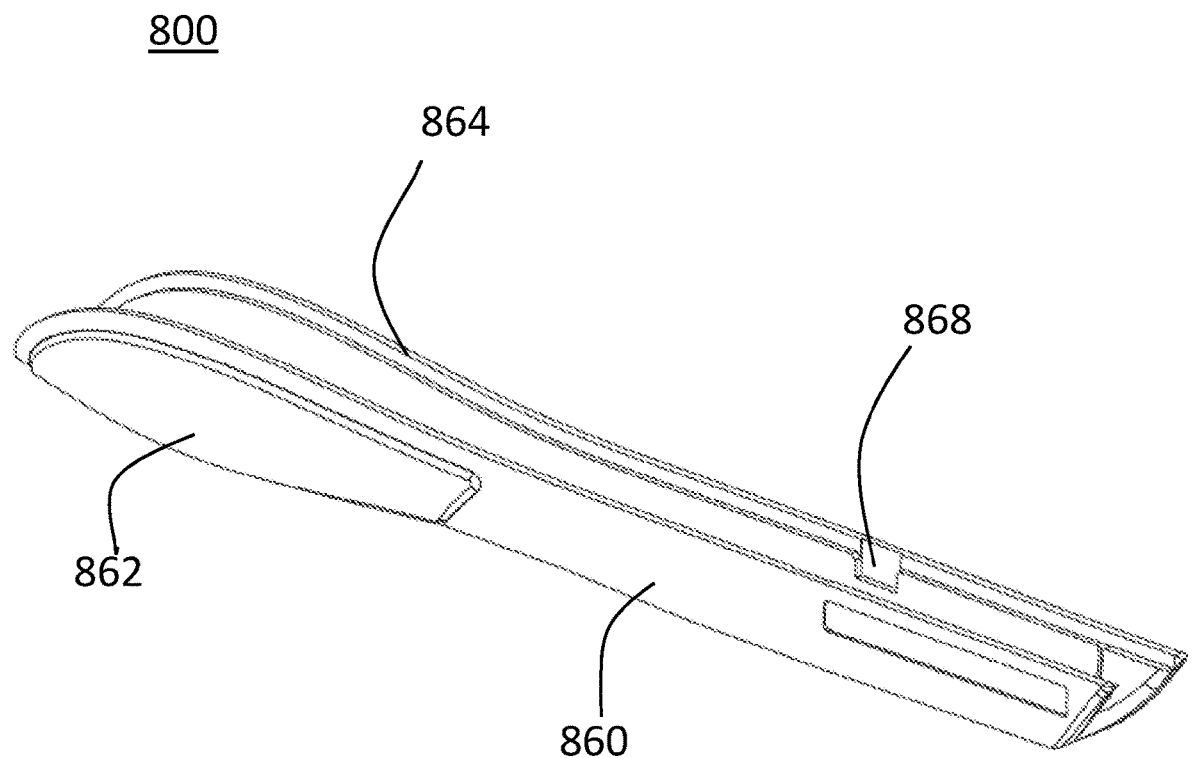
FIG. 8E is a front perspective view of a bottom portion of a handpiece of an extendable probe assembly of a multi-functional electrosurgical plasma accessory in accordance with a preferred embodiment of the present invention.
Figure 8F:
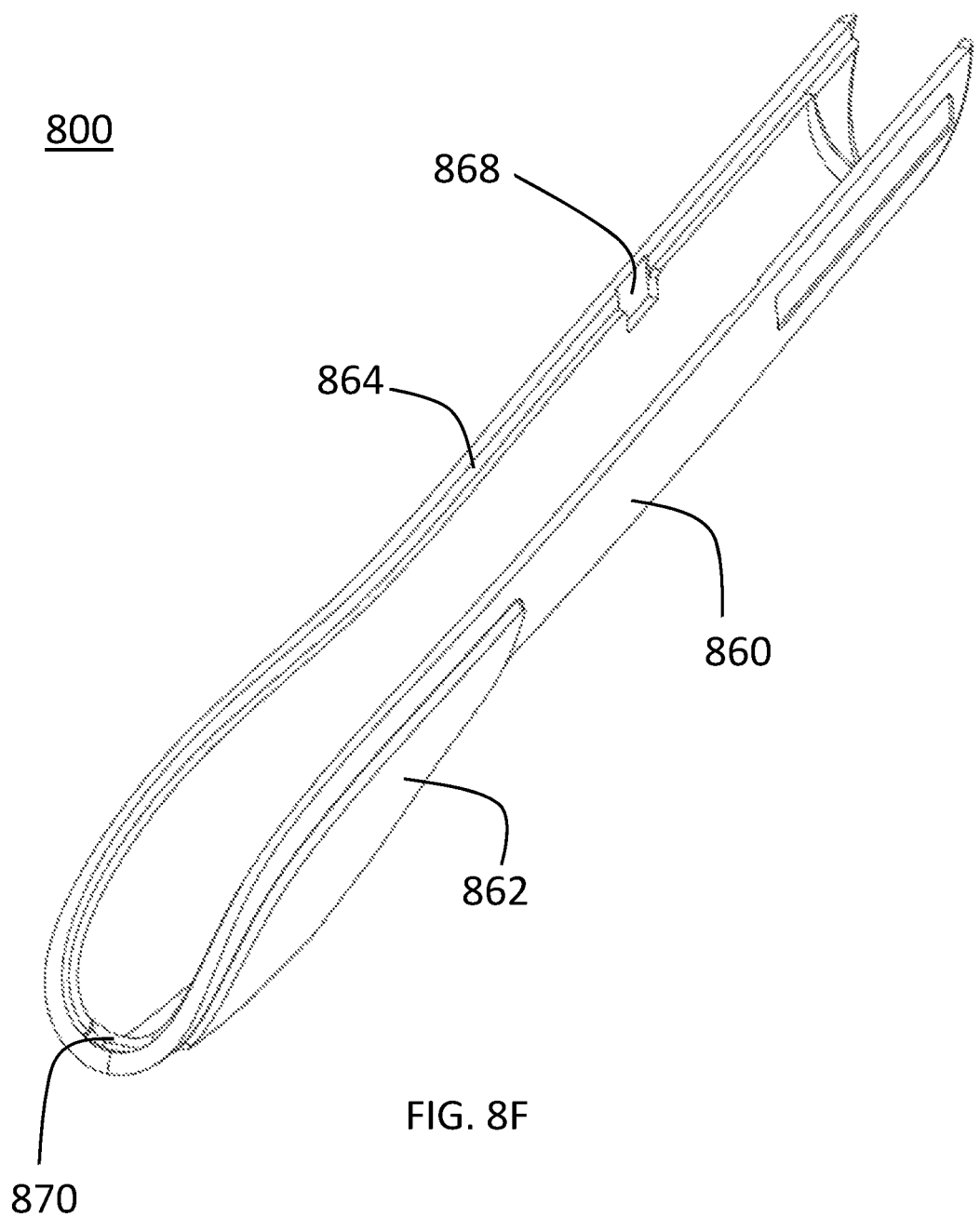
FIG. 8F is a rear perspective view of a bottom portion of a handpiece of an extendable probe assembly of a multi-functional electrosurgical plasma accessory in accordance with a preferred embodiment of the present invention.

The handpiece 700 has a housing having an upper portion shown in FIGS. 7A-7L and a lower portion shown in FIGS. 8A-8F. The upper portion has a body 710 having a plurality of openings 742, 744 and 746 therein for receiving control buttons. The body 710 may have a recessed area 748 for receiving, for example, a product label. The upper portion has a ridge structure 712 along its sides and tabs 730 and 754 for mating with the bottom portion. The upper portion has a threaded neck 720 for mating with the threads on the collet 600. The interior of the threaded neck 720 has a pair of different grooves 722, 724 for engaging with the ridges 542, 544 on the spacer 500. On the interior of the upper portion adjacent each hole 742, 744 and 746 there is a part of support elements 743, 745 and 747 for supporting a PCB board and buttons for controlling the gas flow and the flow of electricity. The interior of the upper portion additionally has a support 752 for supporting the PCB board. The bottom or lower portion 800 of the handpiece 700 has a body 660 a pair of grip portions 862, grooves 868 for engaging with tabs 730 in the upper portion, and a ridge structure 864 for engaging with the ridge structure 712 in the upper portion of the handpiece.

Figure 9A:
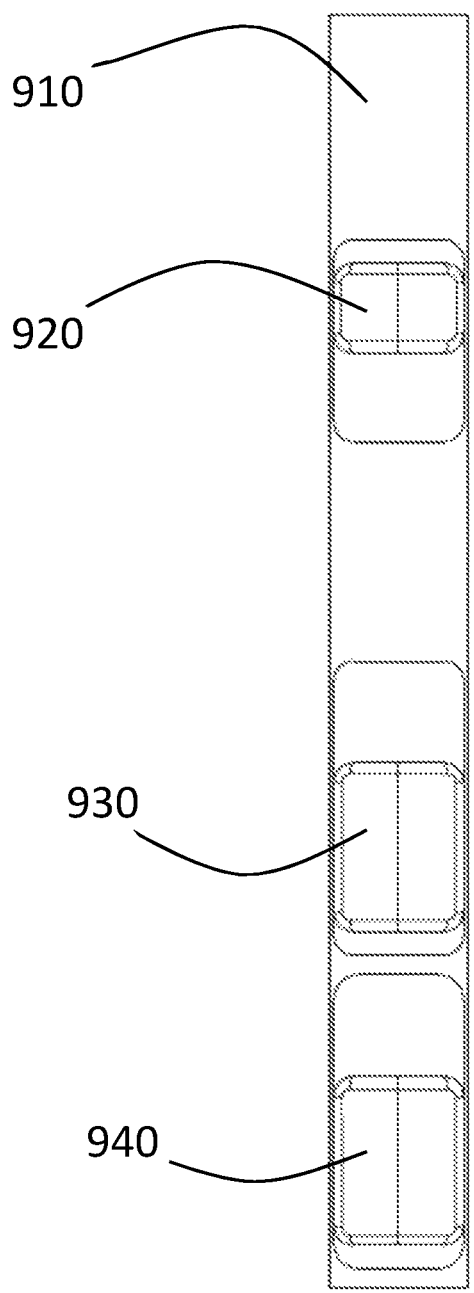
FIG. 9A is a top view of buttons and PCB board of a handpiece of an extendable probe assembly of a multi-functional electrosurgical plasma accessory in accordance with a preferred embodiment of the present invention.
Figure 9B:
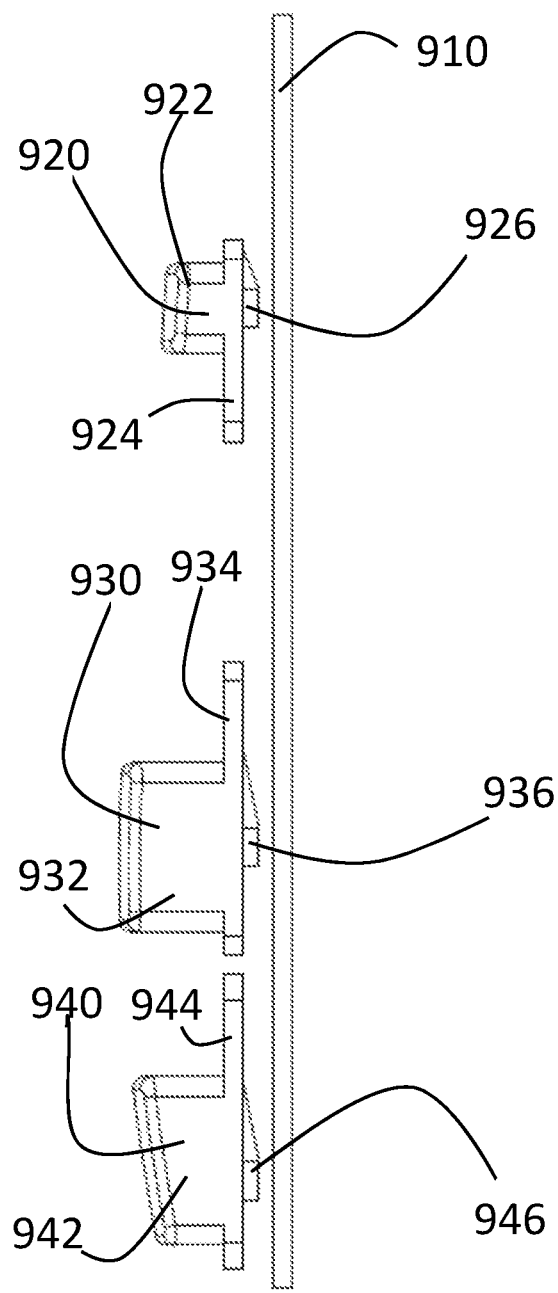
FIG. 9B is a side view of buttons and PCB board of a handpiece of an extendable probe assembly of a multi-functional electrosurgical plasma accessory in accordance with a preferred embodiment of the present invention.
Figure 9C:
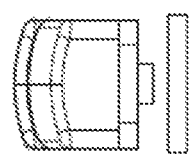
FIG. 9C is a front view of buttons and PCB board of a handpiece of an extendable probe assembly of a multi-functional electrosurgical plasma accessory in accordance with a preferred embodiment of the present invention.
Figure 9D:
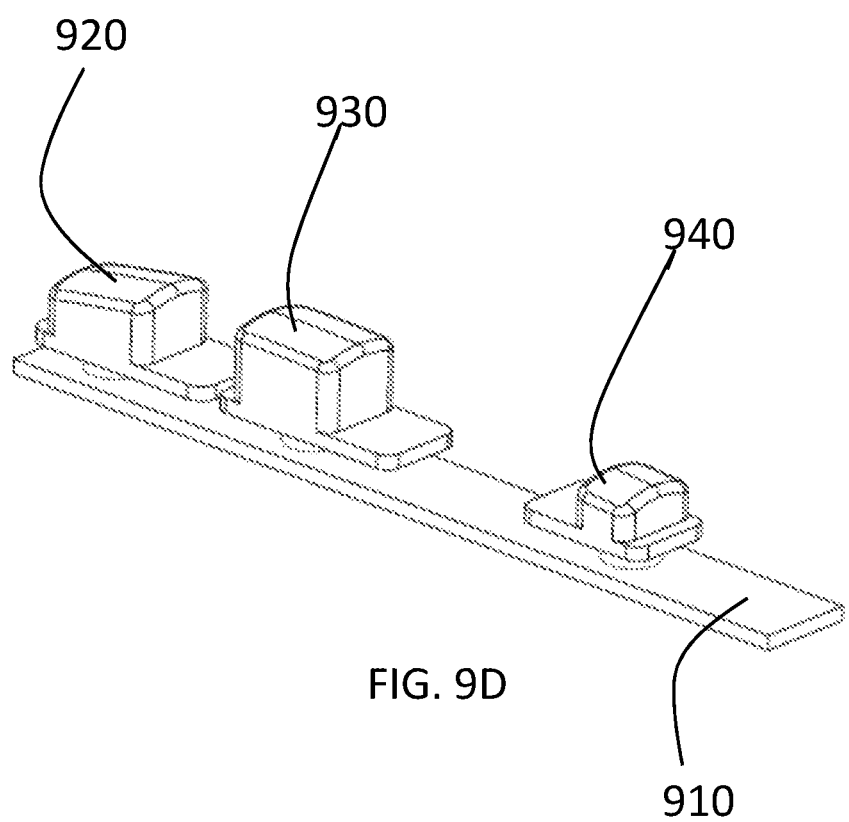
Figure 10E:
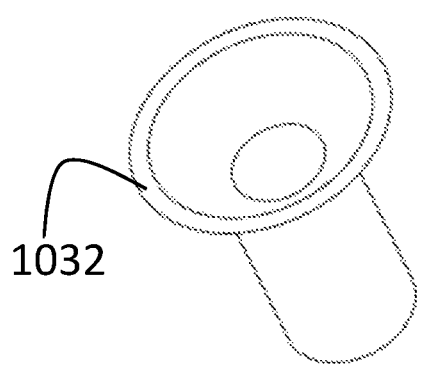
FIG. 10E is a rear perspective view of a metal insert of a connector of a handpiece of an extendable probe assembly of a multi-functional electrosurgical plasma accessory in accordance with a preferred embodiment of the present invention.
Figure 10F:
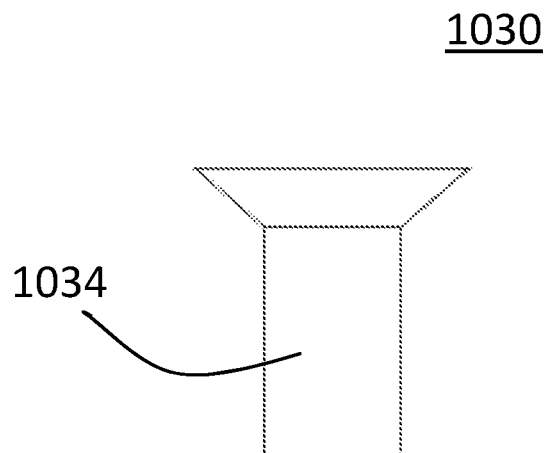
FIG. 10F is a side perspective view of a metal insert of a connector of a handpiece of an extendable probe assembly of a multi-functional electrosurgical plasma accessory in accordance with a preferred embodiment of the present invention.
Figure 10G:
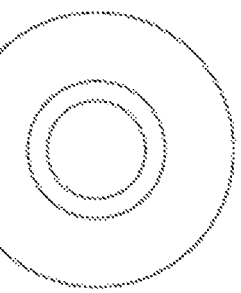
FIG. 10G is a rear end view of a metal insert of a connector of a handpiece of an extendable probe assembly of a multi-functional electrosurgical plasma accessory in accordance with a preferred embodiment of the present invention.

The PCB board/button assembly is shown in FIGS. 9A-9D. The PCB board 910 is supported in the hand piece by the support elements 743, 745, 747 and 752 in the handpiece 700. Each button has an upper portion 922, 932, 942 that extends through a corresponding hole 742, 744, 746 in the upper body portion 710, a flat retention element 924, 934, 944, and a biasing element 926, 936, 946.

In another preferred embodiment, the present invention is system and method for connecting a probe assembly to a handpiece of a multi-functional electrosurgical plasma accessory. The distal end of the handpiece has a connector portion having external threads for mating with a collet on a probe assembly. The neck of the connector portion of the handpiece has an alignment slot with sides angling in from the open end of the slot. The sides of the slot are substantial straight and parallel to the length of the slot near the closed end of the slot. The angled sides serve to rotationally self-align a guide member on a spacer of the probe assembly to ensure that the probe assembly is properly aligned with the handpiece. The connector in the handpiece has an interior channel with a plurality of beveled shoulders to axially align the spacer with the handpiece. The spacer has a first end for inserting into the connector portion of the handpiece. The first end is beveled to provide initial axial self-alignment. The spacer has a beveled shoulder partially along is length to provide further axial self-alignment of the spacer with the connector portion of the handpiece. The spacer further has a stop member, which will be adjacent the distal end of the connector portion of the handpiece when the probe assembly is fully inserted into the handpiece. The spacer still further has a ridge parallel with its axis for radial alignment of the spacer with the handpiece. The distal end of the ridge is angled to provide tactile radial self-alignment of the probe assembly with the handpiece.

Figures 11A, 11B:
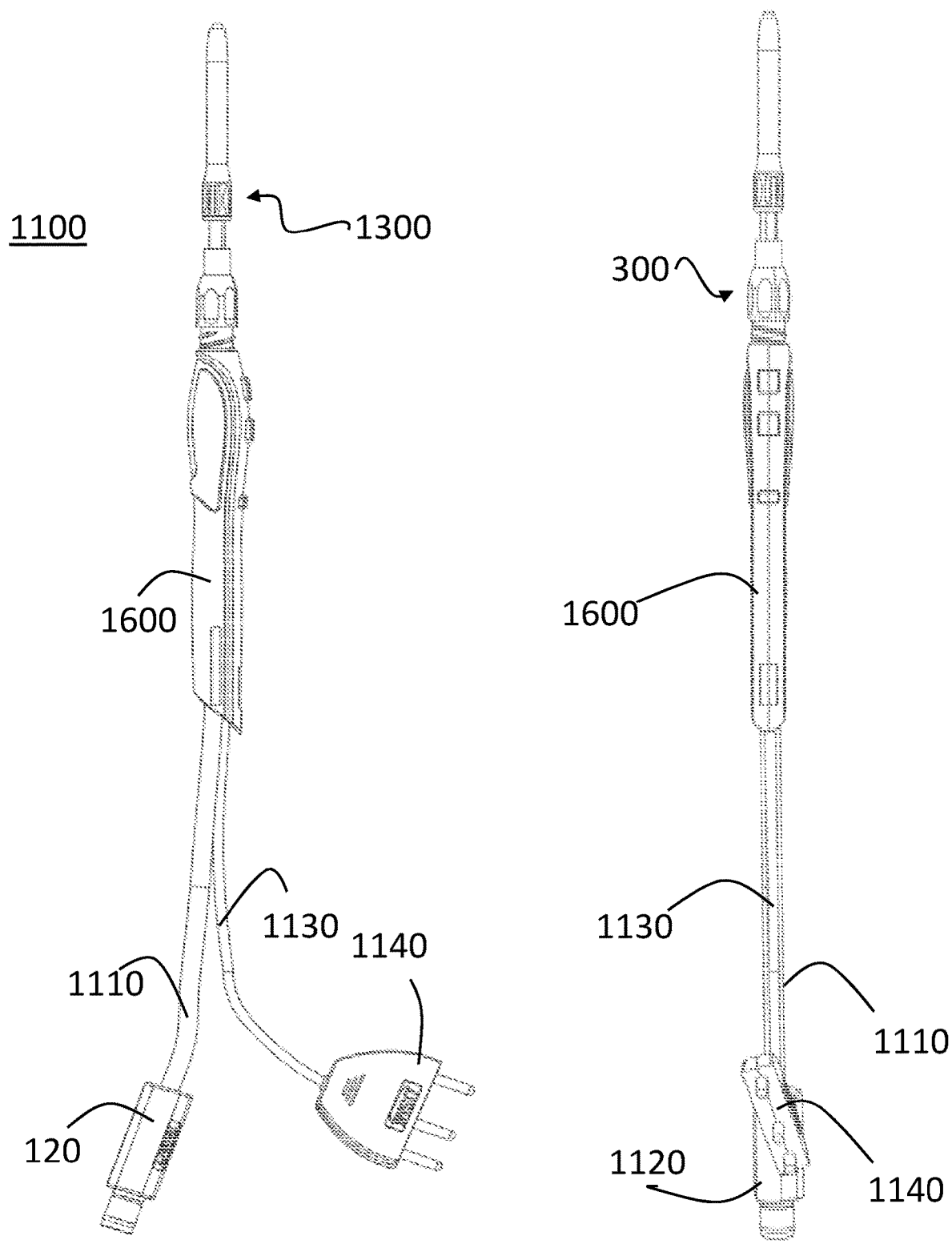
FIG. 11A is a first side view of a multi-functional electrosurgical plasma accessory in accordance with a second preferred embodiment of the present invention.
FIG. 11B is a top view of a multi-functional electrosurgical plasma accessory in accordance with a second preferred embodiment of the present invention.
Figures 11C, 11D:
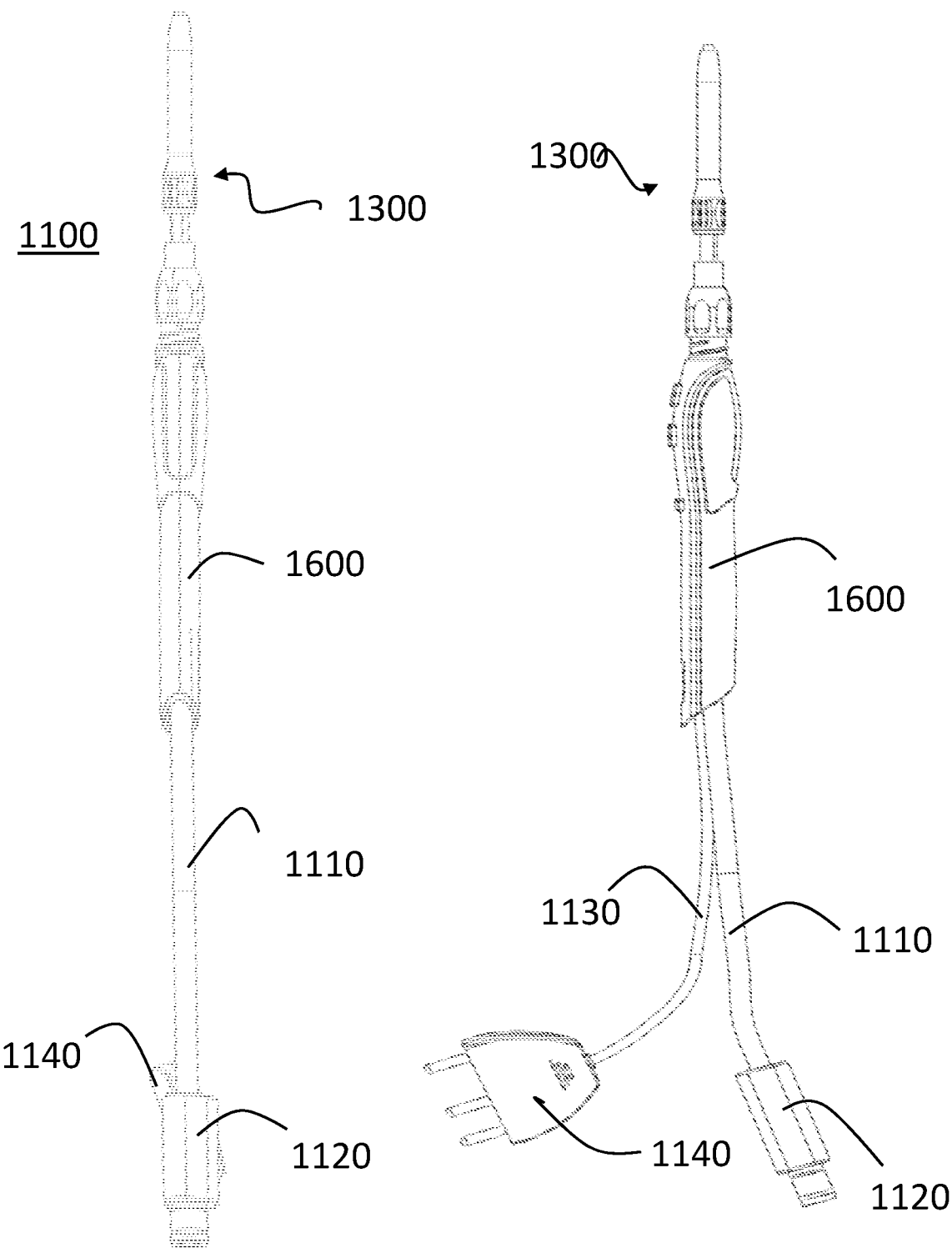
FIG. 11C is a bottom view of a multi-functional electrosurgical plasma accessory in accordance with a second preferred embodiment of the present invention.
FIG. 11D is a second side view of a multi-functional electrosurgical plasma accessory in accordance with a second preferred embodiment of the present invention.
Figure 11E:
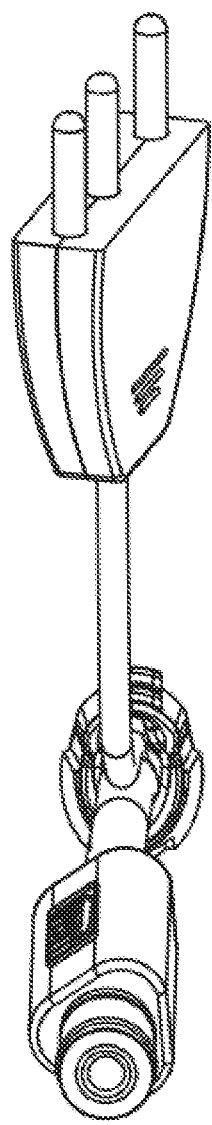
FIG. 11E is a rear view of a multi-functional electrosurgical plasma accessory in accordance with a second preferred embodiment of the present invention.
Figure 11F:
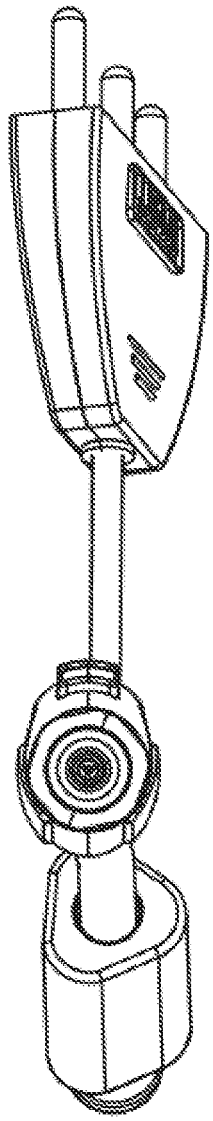
FIG. 11F is a front view of a multi-functional electrosurgical plasma accessory in accordance with a second preferred embodiment of the present invention.
Figure 11G:
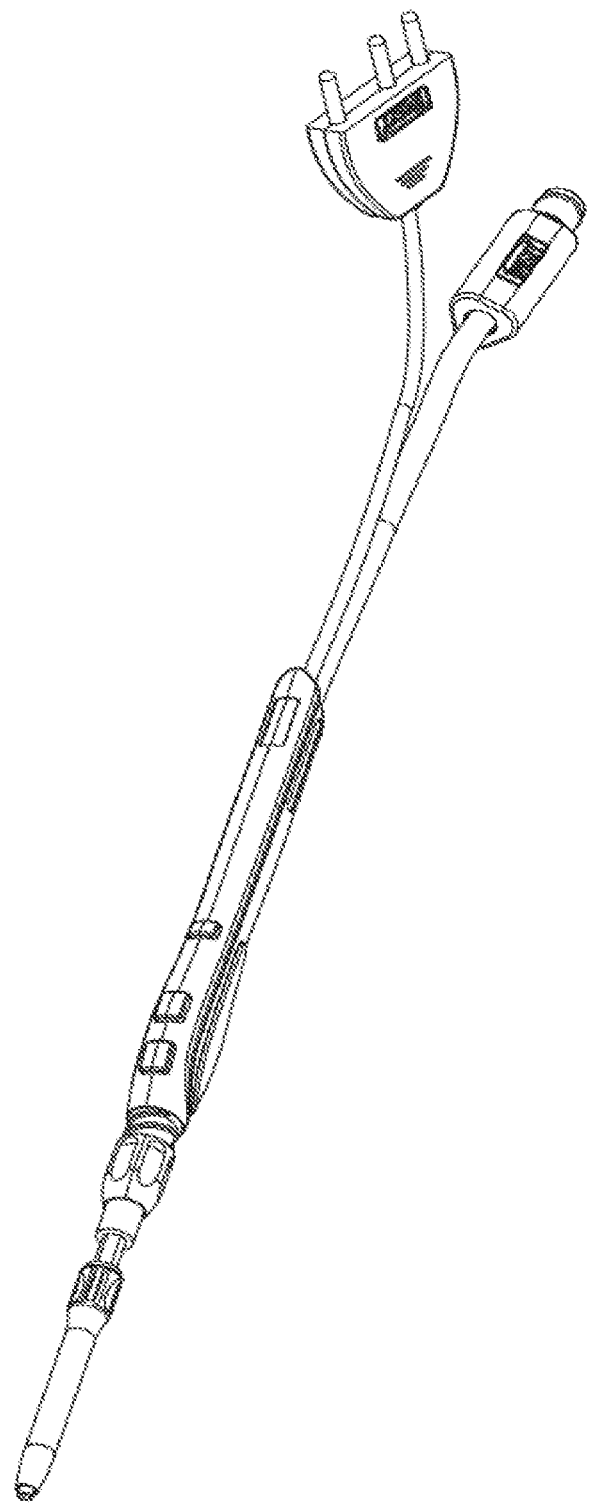
FIG. 11G is a perspective view of a multi-functional electrosurgical plasma accessory in accordance with a second preferred embodiment of the present invention.
Figure 12A:
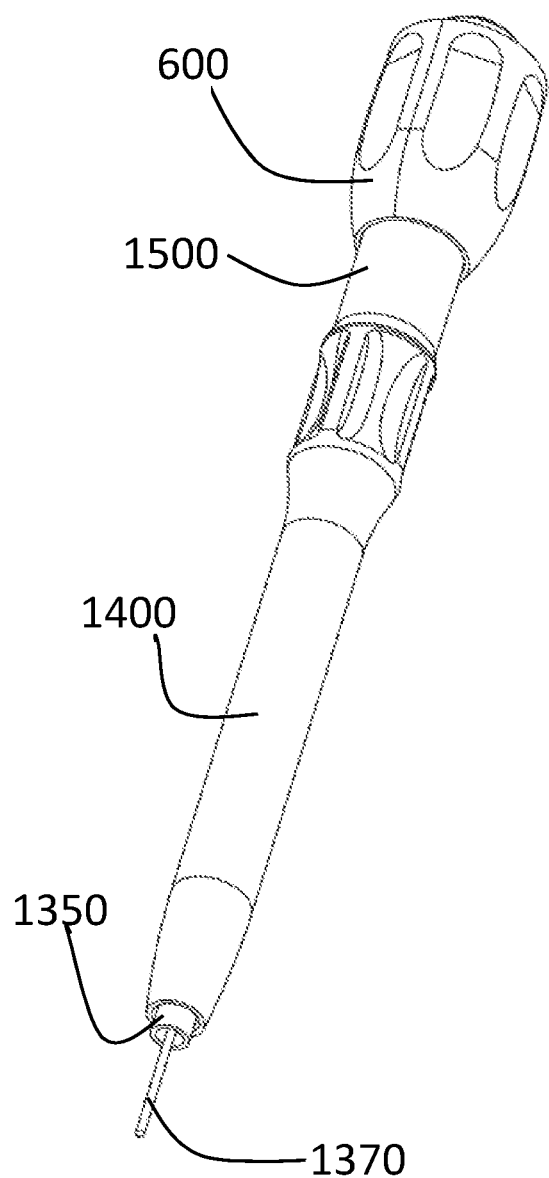
FIG. 12A is a front perspective view of an extendable probe assembly of a multi-functional electrosurgical plasma accessory in accordance with a second preferred embodiment of the present invention in a retracted position such that the electrode is exposed at the tip of the probe.
Figure 12B:
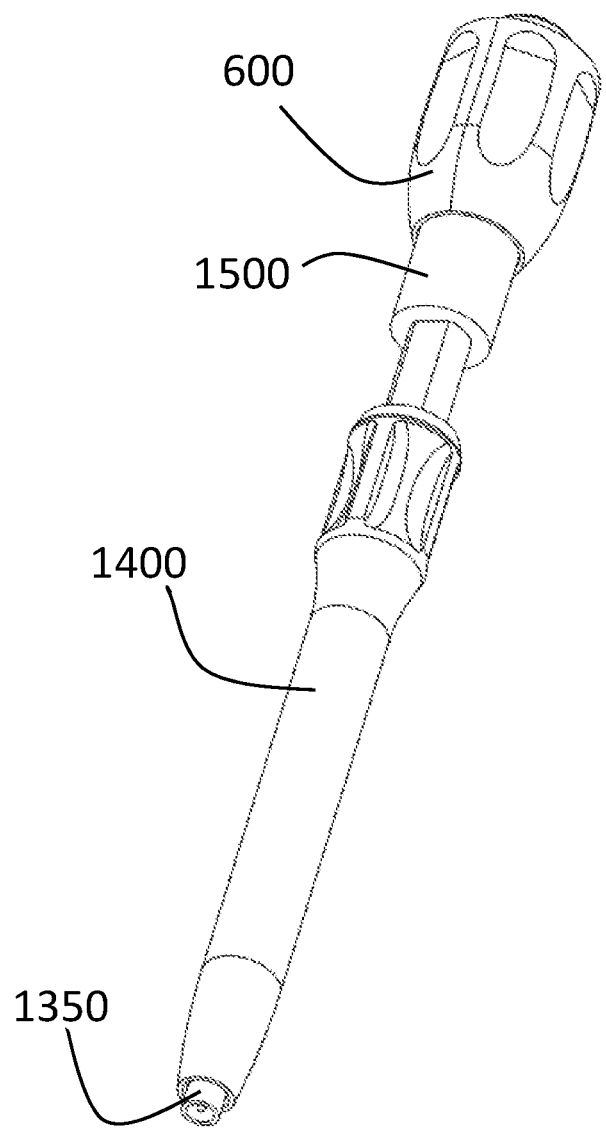
FIG. 12B is a front perspective view of an extendable probe assembly of a multi-functional electrosurgical plasma accessory in accordance with a second preferred embodiment of the present invention in an extended position such that the electrode does not extend outside of the tip of the probe.
Figures 12H, 12I:
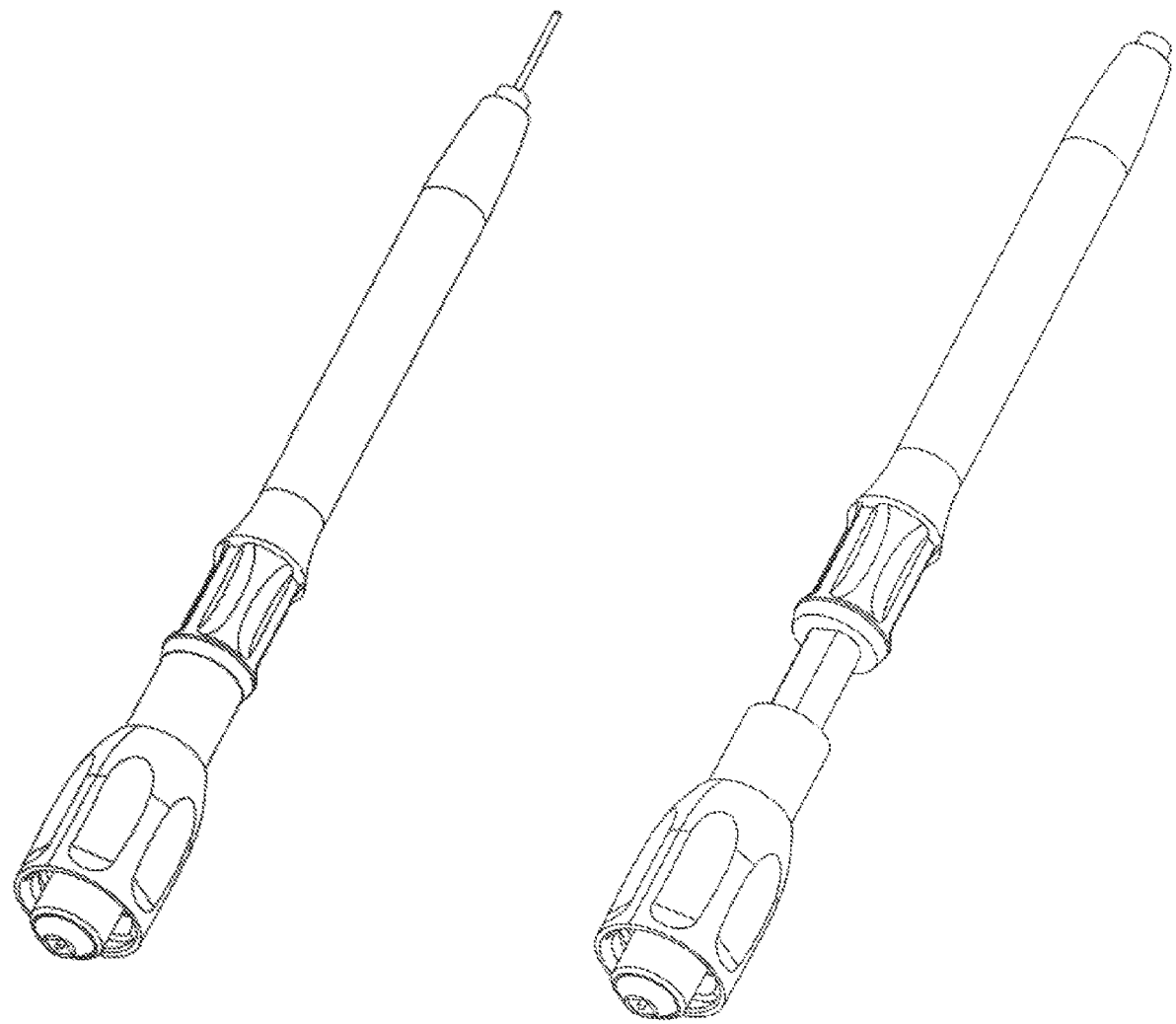
FIG. 12H is a rear perspective view of an extendable probe assembly of a multi-functional electrosurgical plasma accessory in accordance with a second preferred embodiment of the present invention in a retracted position.
FIG. 12I is a rear perspective view of an extendable probe assembly of a multi-functional electrosurgical plasma accessory in accordance with a second preferred embodiment of the present invention in an extended position.
Figure 12J:
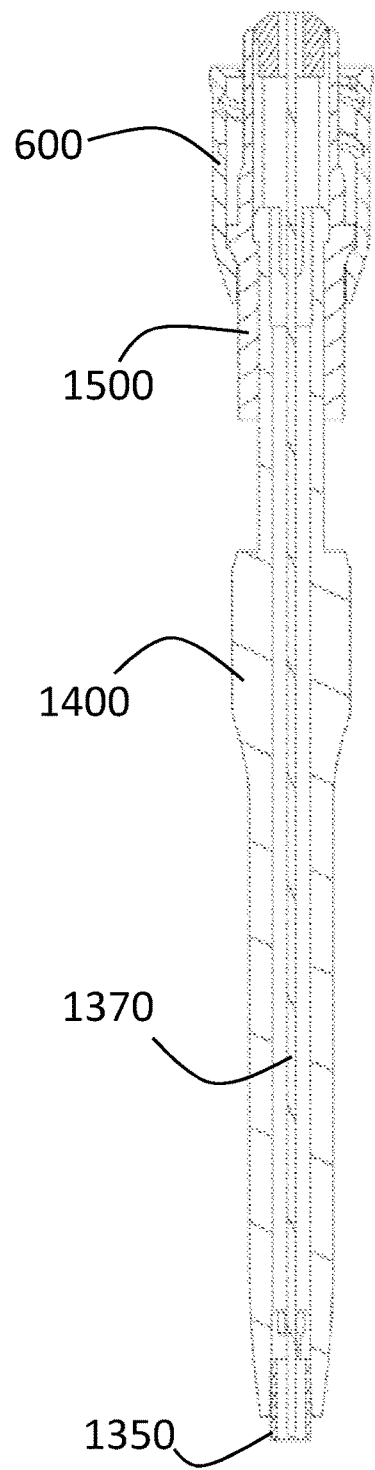
FIG. 12J is a first cross-sectional view of an extendable probe assembly of a multi-functional electrosurgical plasma accessory in accordance with a second preferred embodiment of the present invention in a retracted position.
Figure 12K:
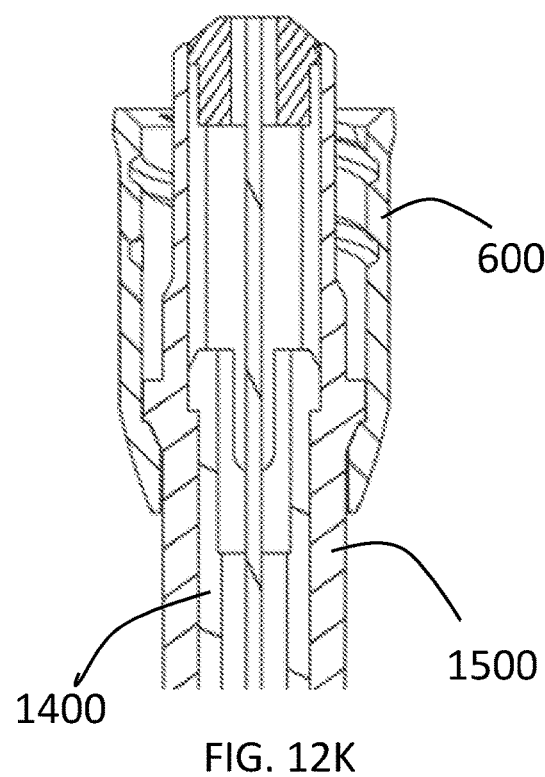
FIG. 12K is a close-up view of the proximal end of the first cross-sectional view shown in FIG. 12J.
Figure 12L:
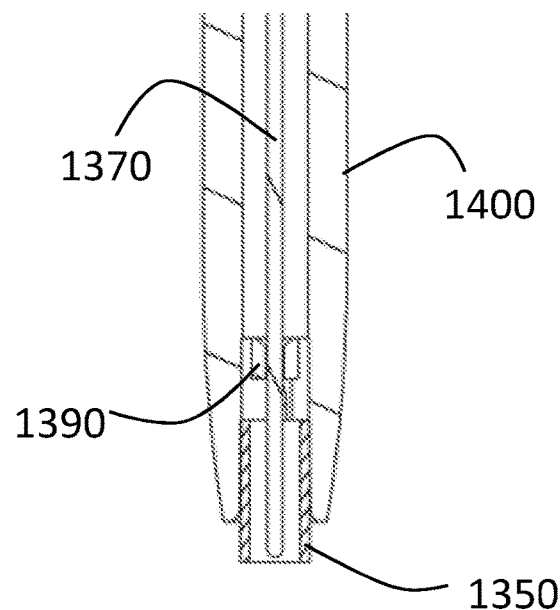
FIG. 12L is a close-up view of the distal end of the first cross-sectional view shown in FIG. 12J.
Figure 12M:
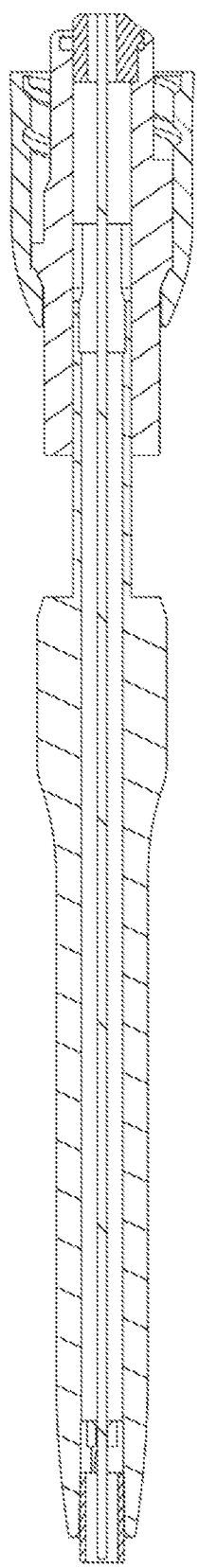
FIG. 12M is a second cross-sectional view of an extendable probe assembly of a multi-functional electrosurgical plasma accessory in accordance with a second preferred embodiment of the present invention in a retracted position.
Figure 12N:
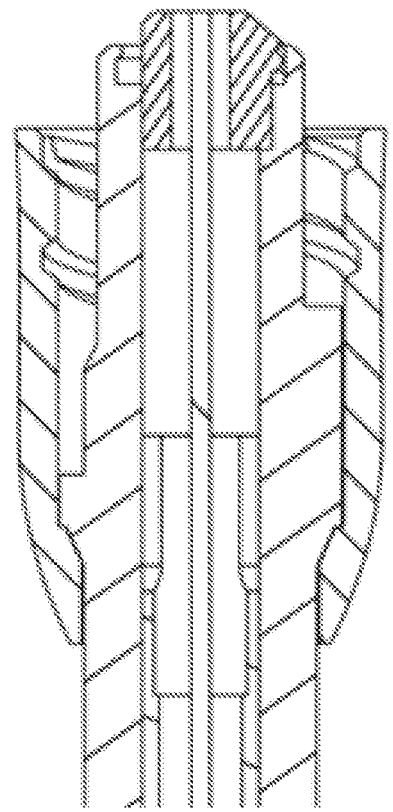
FIG. 12N is a close-up view of the proximal end of the second cross-sectional view shown in FIG. 12M.
Figure 13A:
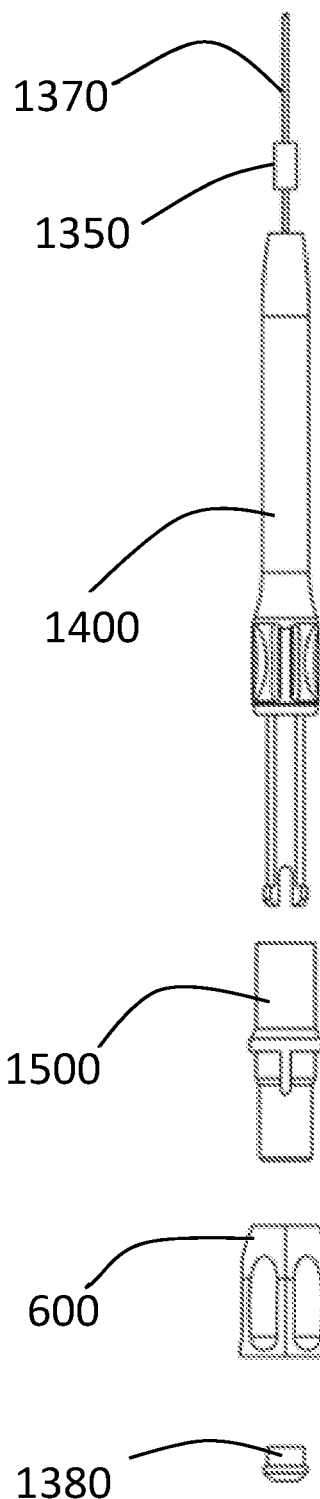
FIG. 13A is a first side view assembly drawing of an extendable probe assembly of a multi-functional electrosurgical plasma accessory in accordance with a second preferred embodiment of the present invention.
Figure 13B:
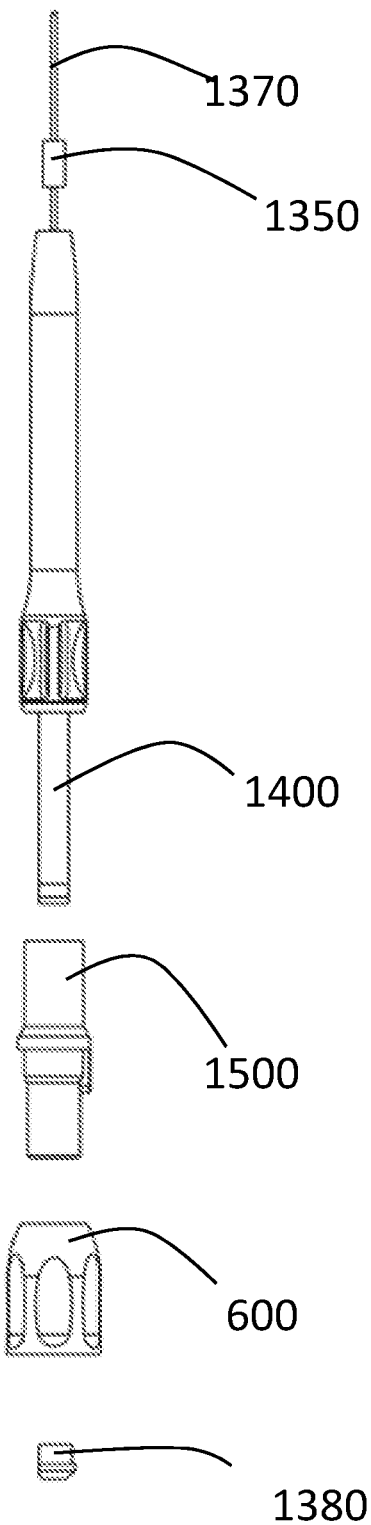
FIG. 13B is a second side view assembly drawing of an extendable probe assembly of a multi-functional electrosurgical plasma accessory in accordance with a second preferred embodiment of the present invention.
Figure 13C:
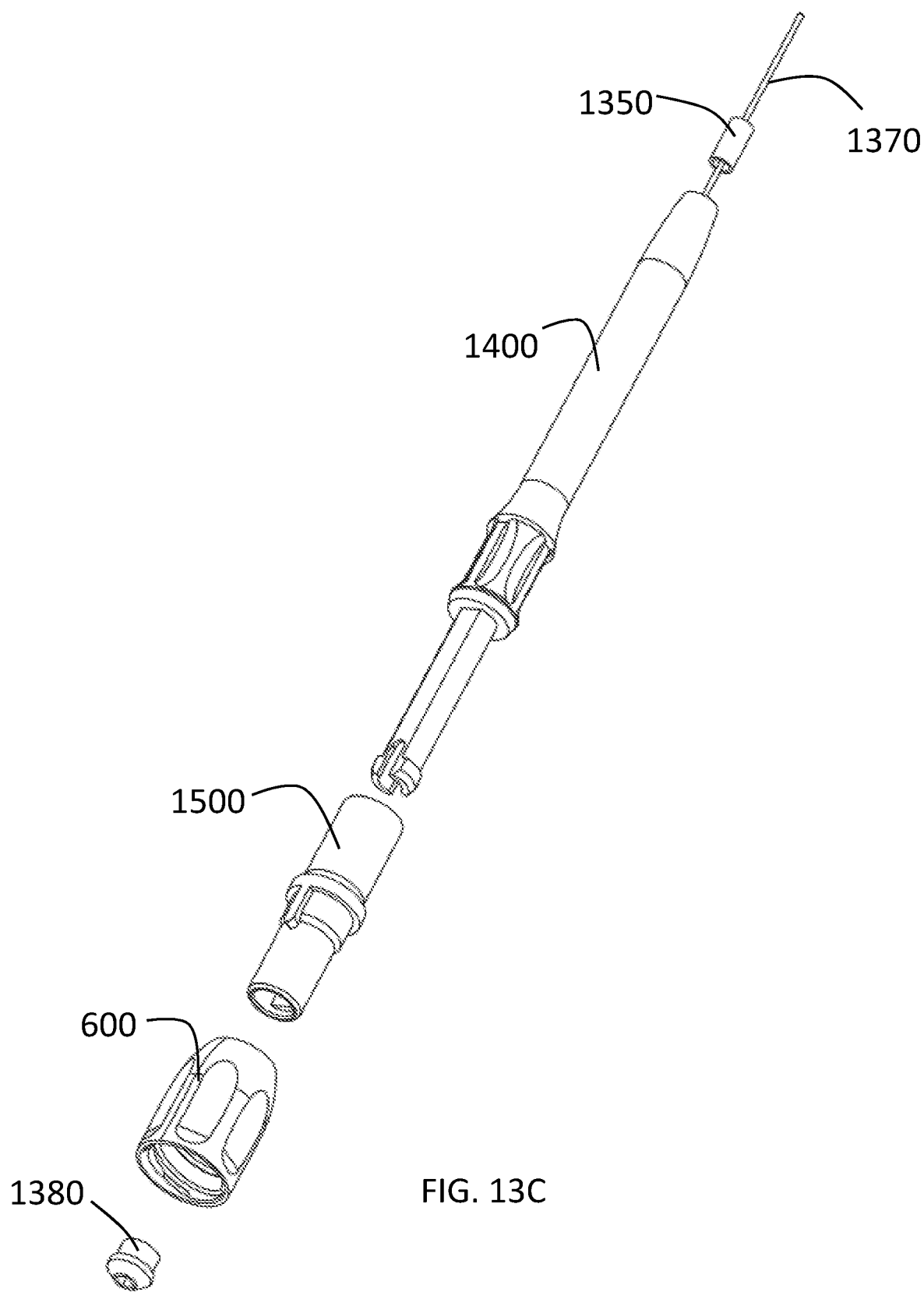
FIG. 13C is a rear perspective view assembly drawing of an extendable probe assembly of a multi-functional electrosurgical plasma accessory in accordance with a second preferred embodiment of the present invention.
Figure 13D:
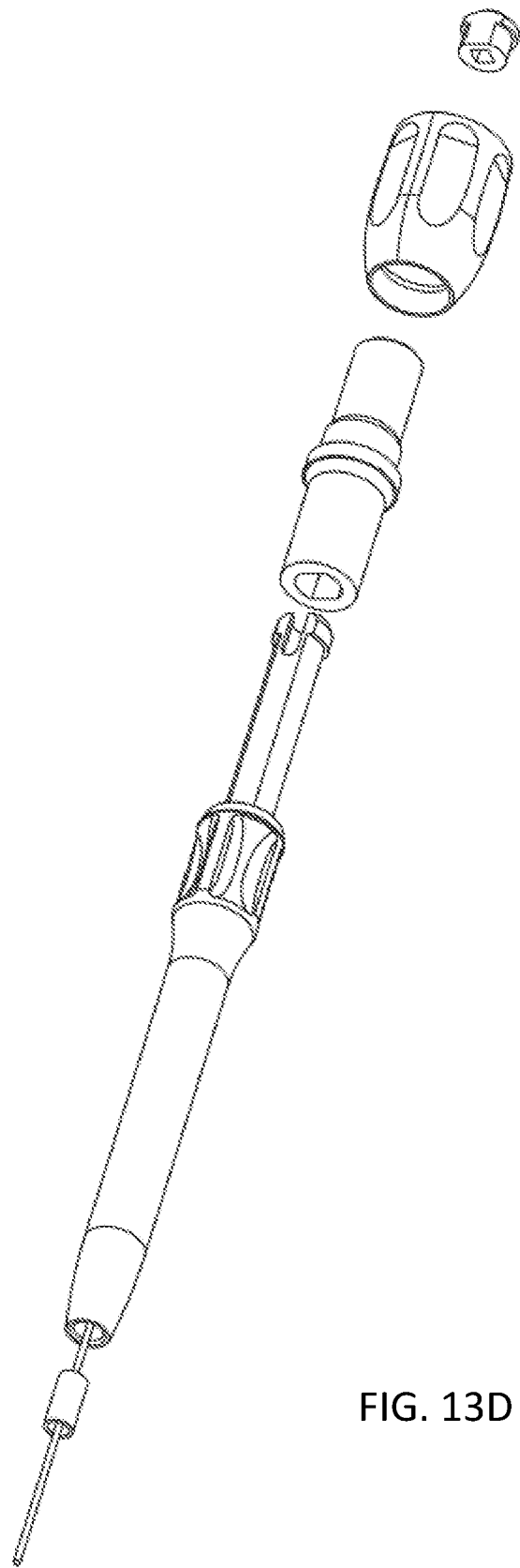
FIG. 13D is a front perspective view assembly drawing of an extendable probe assembly of a multi-functional electrosurgical plasma accessory in accordance with a second preferred embodiment of the present invention.
Figure 14B:
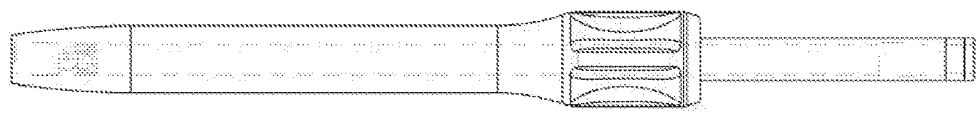
FIG. 14B is a second side view of a shaft of an extendable probe assembly of a multi-functional electrosurgical plasma accessory in accordance with a second preferred embodiment of the present invention.
Figure 14C:
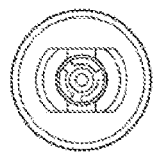
FIG. 14C is an end view of a shaft of an extendable probe assembly of a multi-functional electrosurgical plasma accessory in accordance with a second preferred embodiment of the present invention.
Figure 14A:
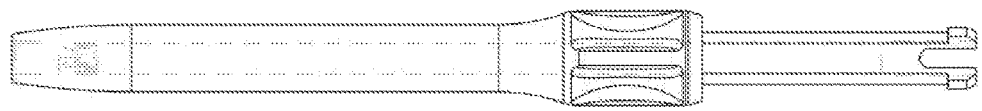
FIG. 14A is a first side view of a shaft of an extendable probe assembly of a multi-functional electrosurgical plasma accessory in accordance with a second preferred embodiment of the present invention.
Figures 14D, 14E:
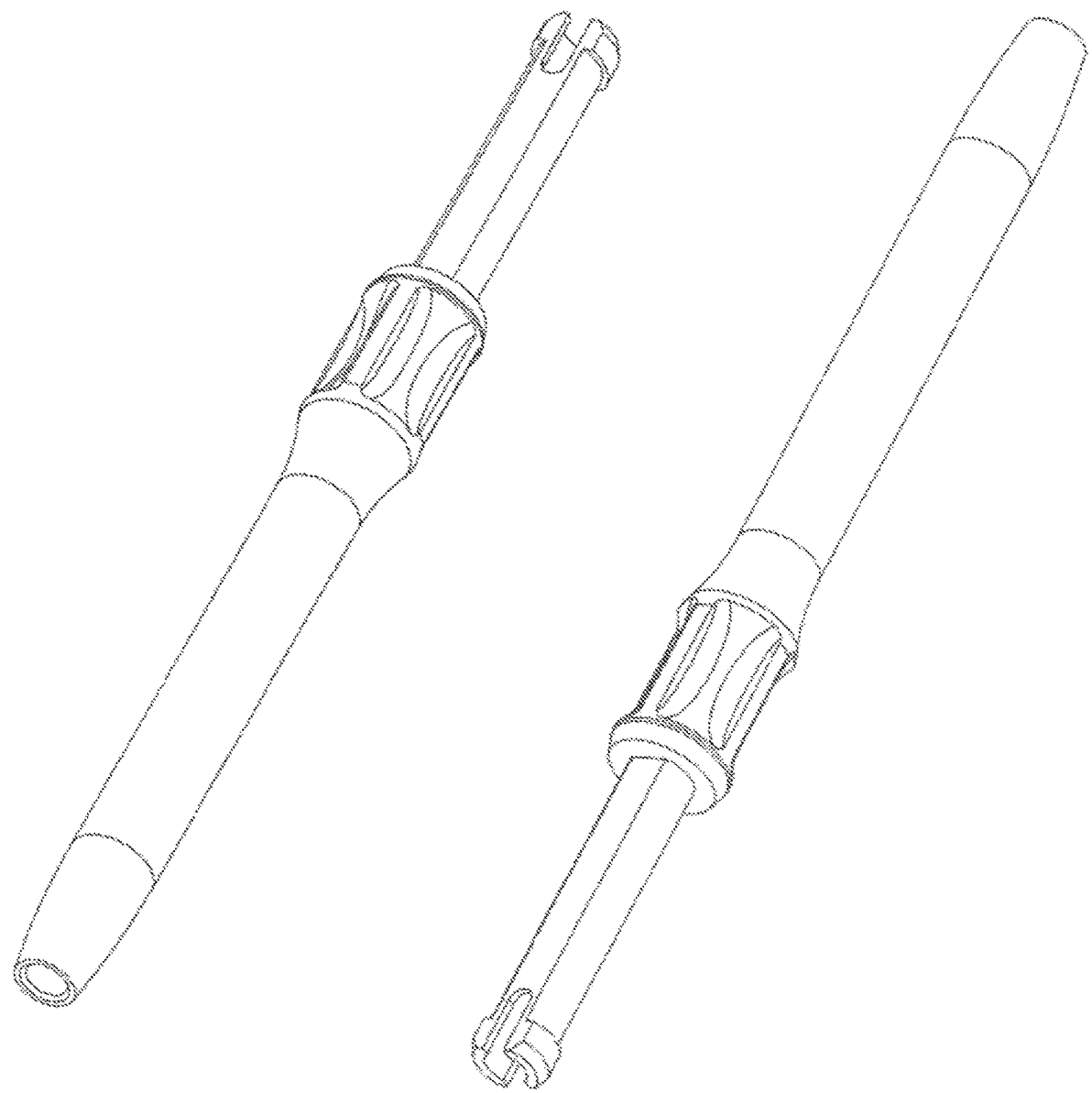
FIG. 14D is a front perspective view of a shaft of an extendable probe assembly of a multi-functional electrosurgical plasma accessory in accordance with a second preferred embodiment of the present invention.
FIG. 14E is a rear perspective view of a shaft of an extendable probe assembly of a multi-functional electrosurgical plasma accessory in accordance with a second preferred embodiment of the present invention.
Figure 14F:
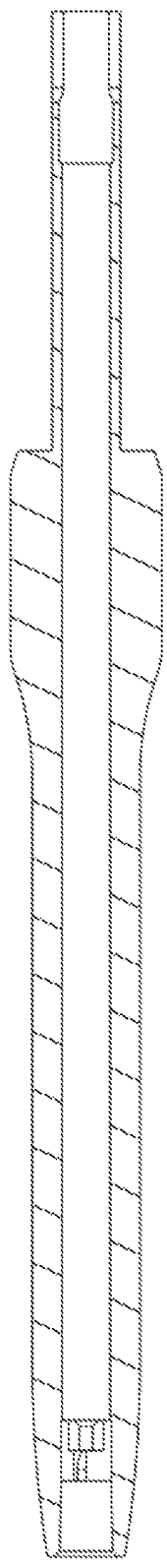
FIG. 14F is a first cross-section view of a shaft of an extendable probe assembly of a multi-functional electrosurgical plasma accessory in accordance with a second preferred embodiment of the present invention.
Figure 14G:
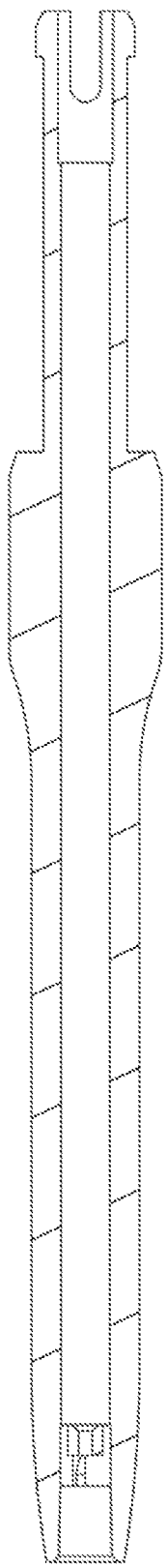
FIG. 14G is a second cross-section view of a shaft of an extendable probe assembly of a multi-functional electrosurgical plasma accessory in accordance with a second preferred embodiment of the present invention.
Figure 15A:
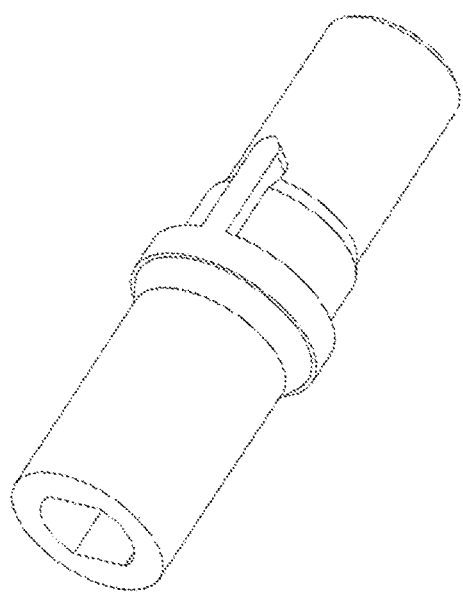
FIG. 15A is a first perspective view of a shaft of a keyed cylinder of an extendable probe assembly of a multi-functional electrosurgical plasma accessory in accordance with a second preferred embodiment of the present invention.
Figure 15B:
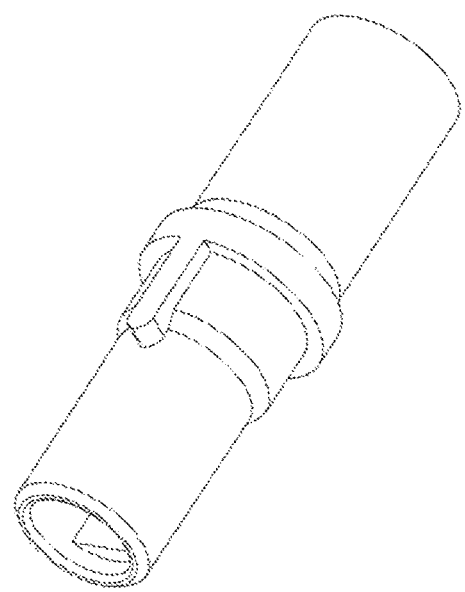
FIG. 15B is a second perspective view of a shaft of a keyed cylinder of an extendable probe assembly of a multi-functional electrosurgical plasma accessory in accordance with a second preferred embodiment of the present invention.
Figure 15C:
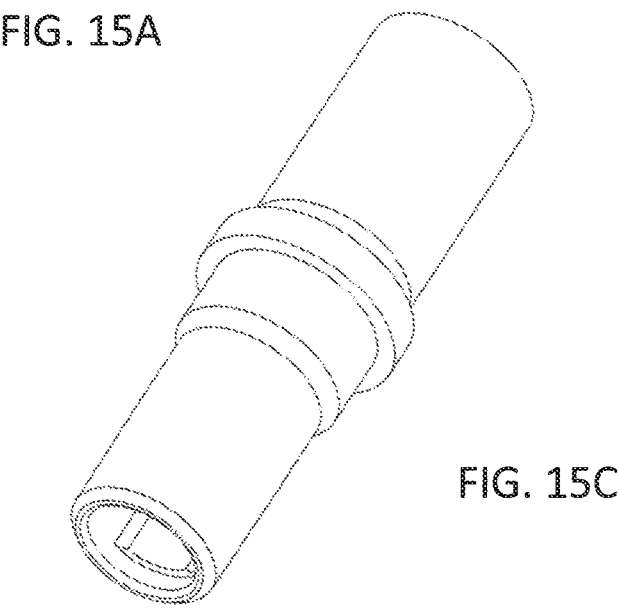
FIG. 15C is a third perspective view of a shaft of a keyed cylinder of an extendable probe assembly of a multi-functional electrosurgical plasma accessory in accordance with a second preferred embodiment of the present invention.
Figure 15F:
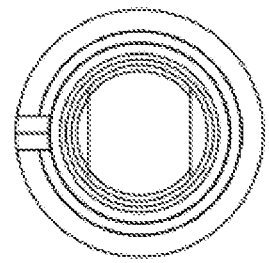
FIG. 15F is a first end view of a shaft of a keyed cylinder of an extendable probe assembly of a multi-functional electrosurgical plasma accessory in accordance with a second preferred embodiment of the present invention.
Figure 15D:
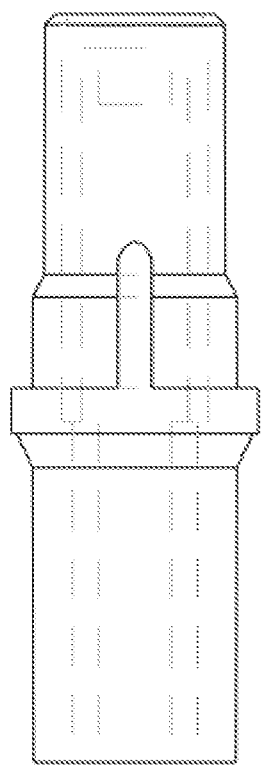
FIG. 15D is a first side view of a shaft of a keyed cylinder of an extendable probe assembly of a multi-functional electrosurgical plasma accessory in accordance with a second preferred embodiment of the present invention.
Figure 15E:
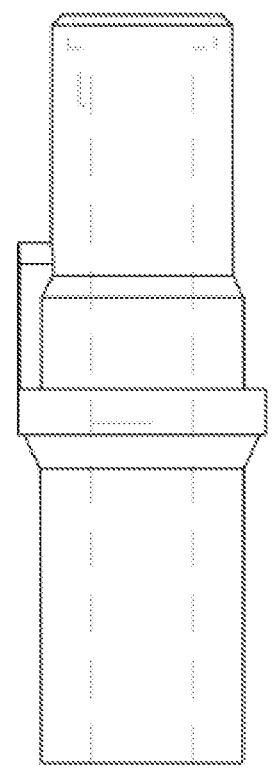
FIG. 15E is a second side view of a shaft of a keyed cylinder of an extendable probe assembly of a multi-functional electrosurgical plasma accessory in accordance with a second preferred embodiment of the present invention.
Figure 15G:
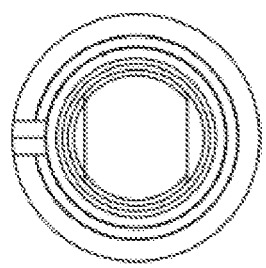
FIG. 15G is a second end view of a shaft of a keyed cylinder of an extendable probe assembly of a multi-functional electrosurgical plasma accessory in accordance with a second preferred embodiment of the present invention.
Figure 15H:
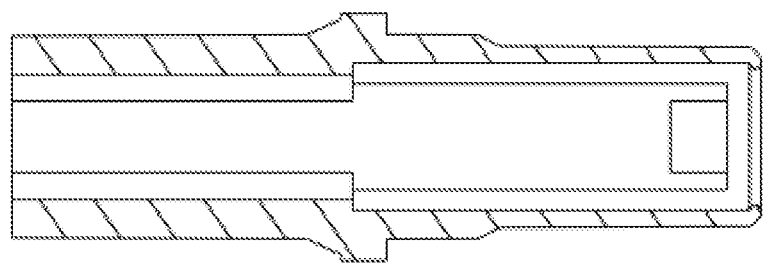
FIG. 15H is a first cross-sectional view of a shaft of a cylinder of an extendable probe assembly of a multi-functional electrosurgical plasma accessory in accordance with a second preferred embodiment of the present invention.
Figure 15I:
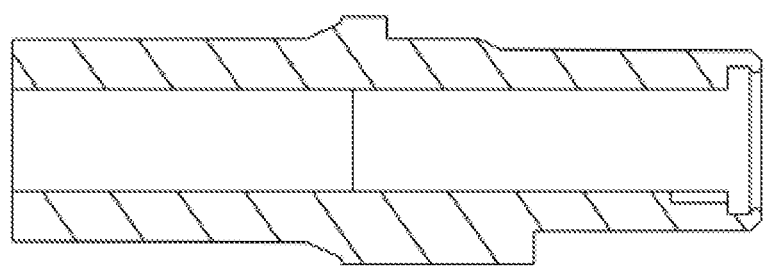
FIG. 15I is a second cross-sectional view of a shaft of a cylinder of an extendable probe assembly of a multi-functional electrosurgical plasma accessory in accordance with a second preferred embodiment of the present invention.
Figure 16A:
FIGS. 16A, 16B and 16C are perspective views of a top portion of a handpiece of an extendable probe assembly of a multi-functional electrosurgical plasma accessory in accordance with a second preferred embodiment of the present invention.
Figure 16B:
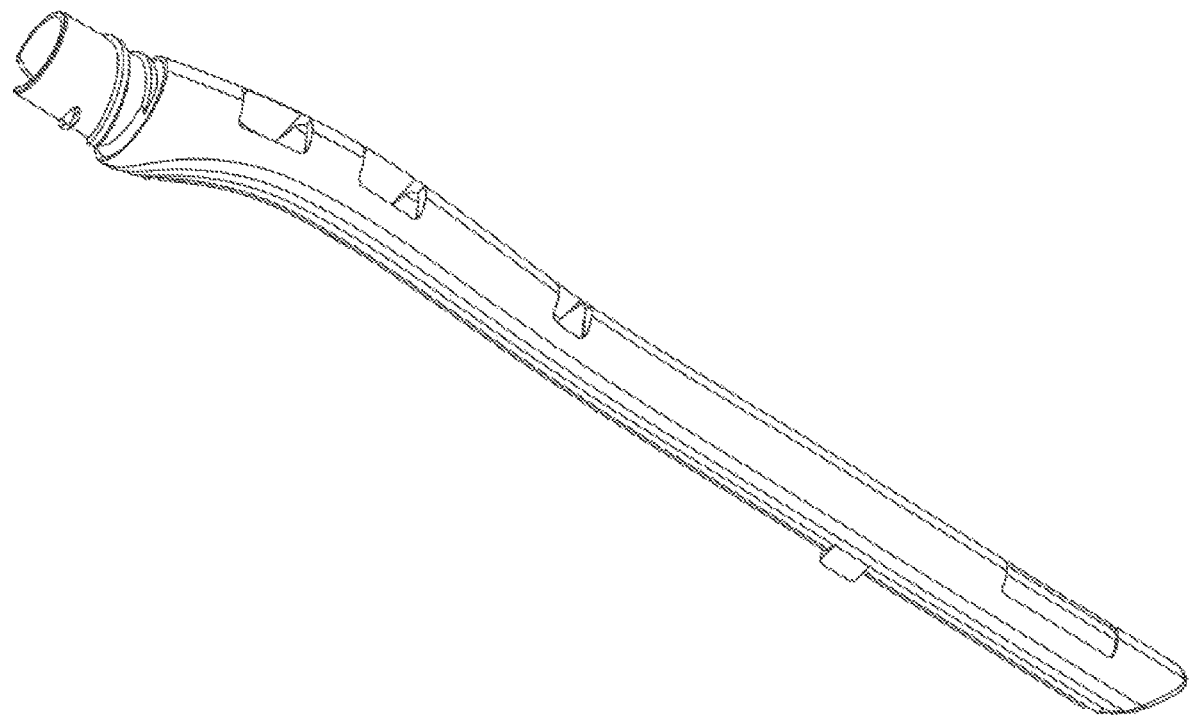
Figure 16C:
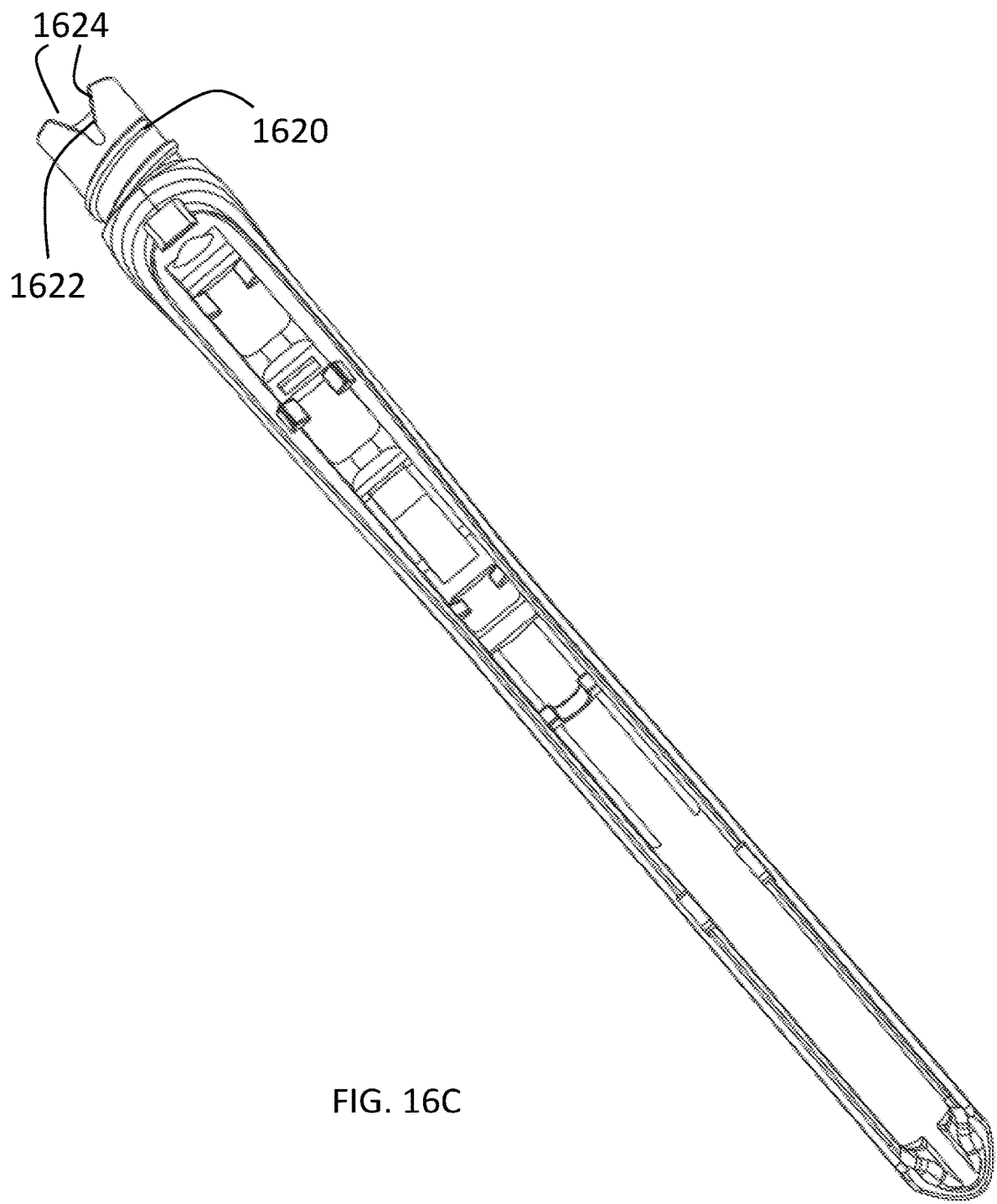
Figure 16D:
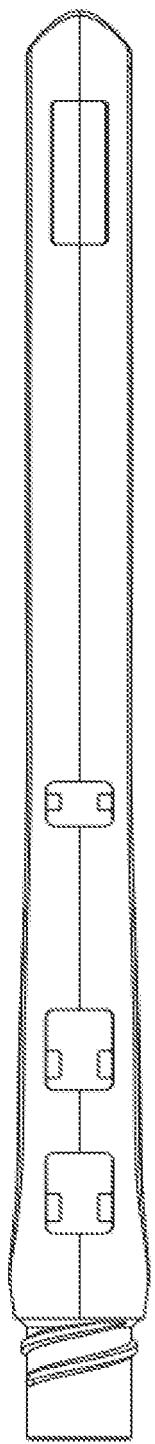
Figure 16E:
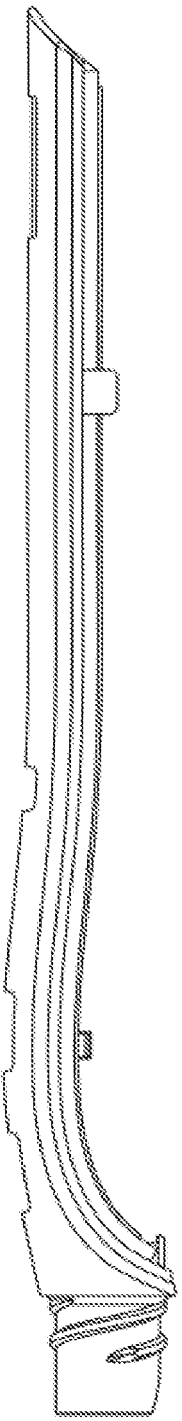
Figure 16F:
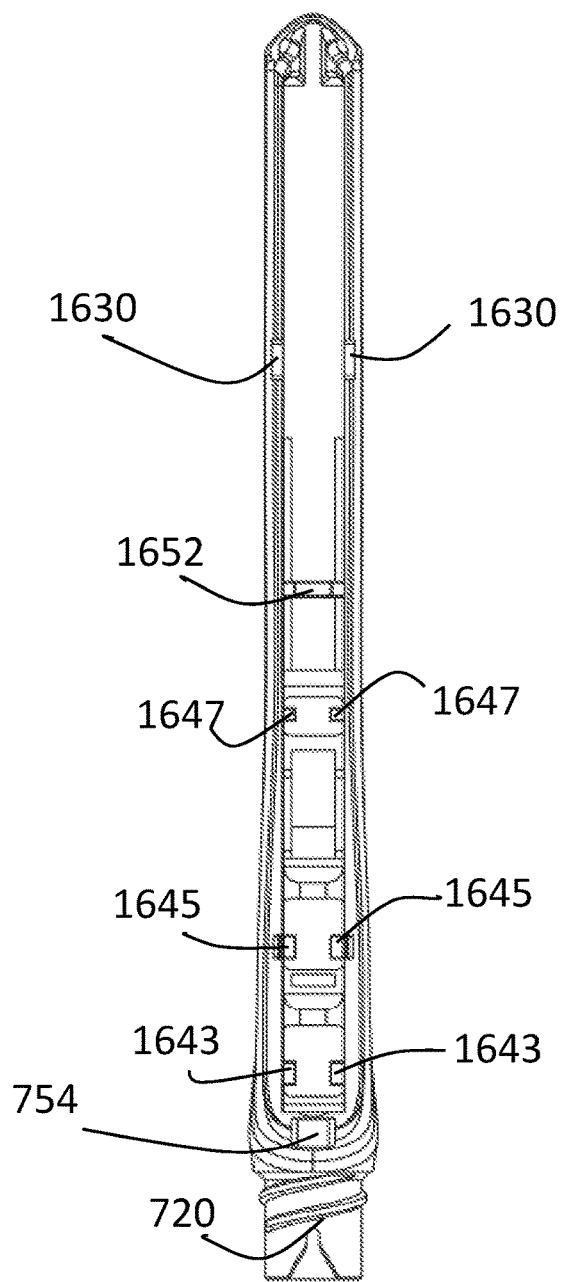
Figure 16G:
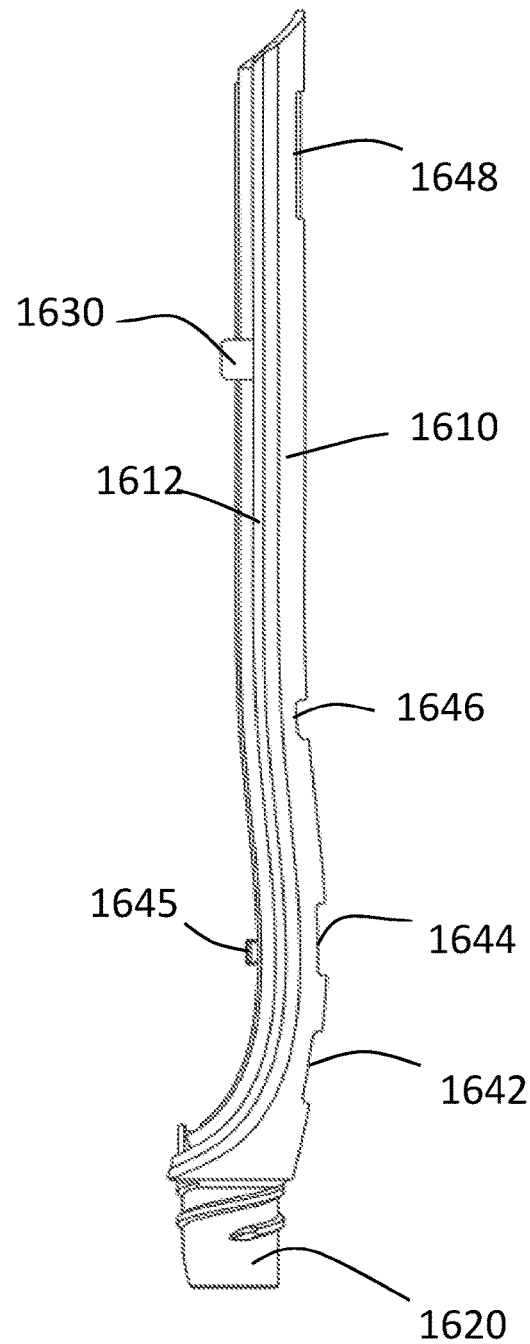
Figure 16H:
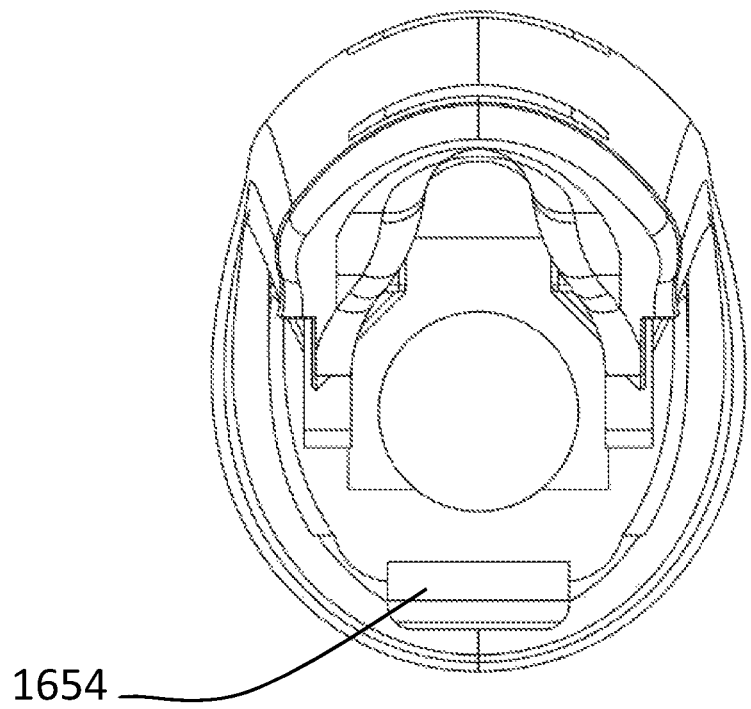
Figure 16I:
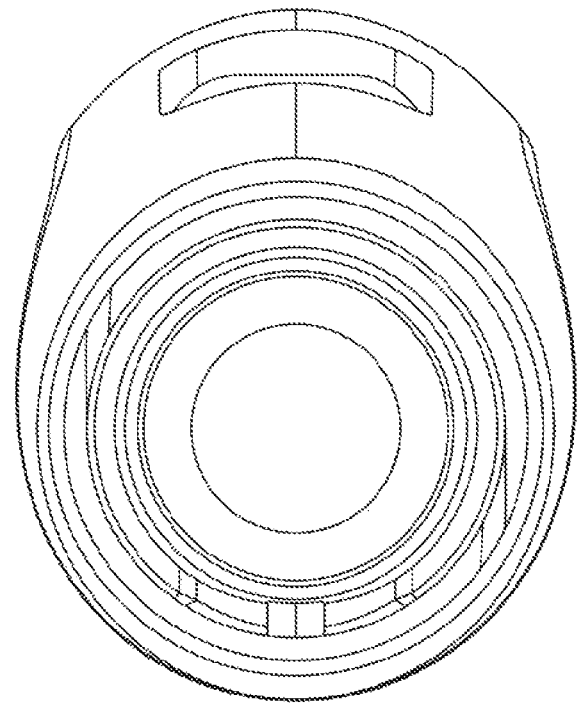
Figure 16J:
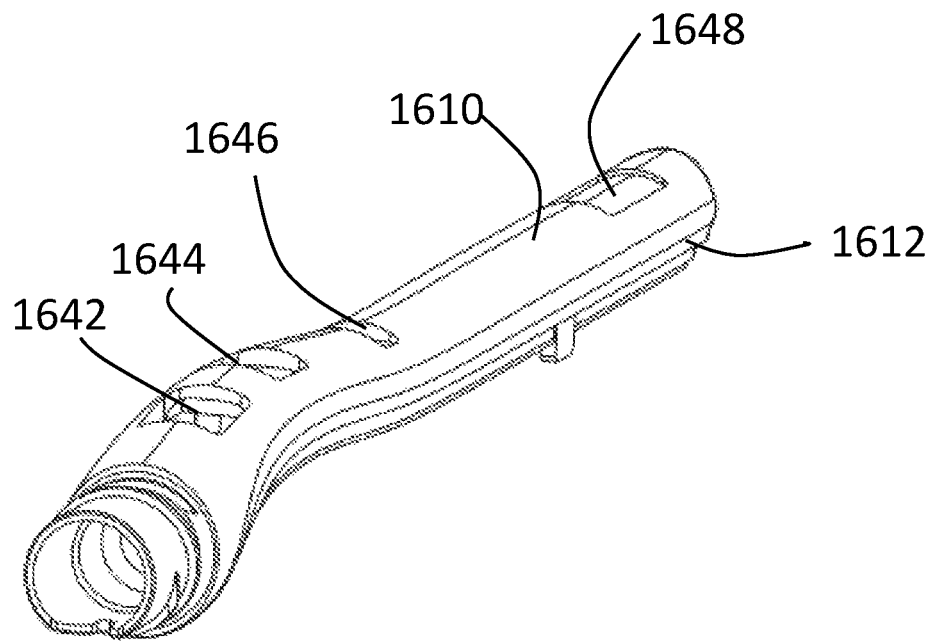
Figure 16K:
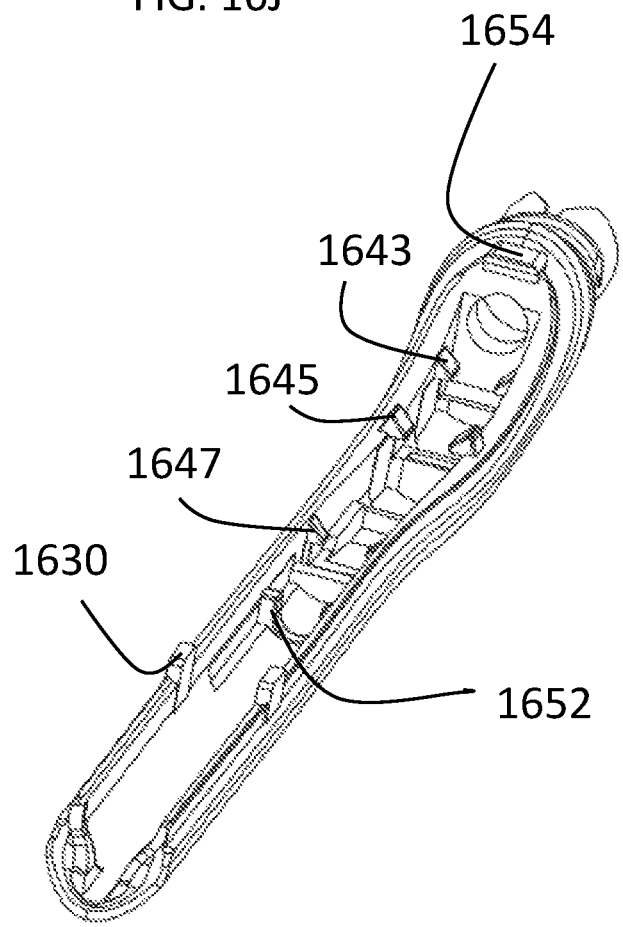
Figure 16L:
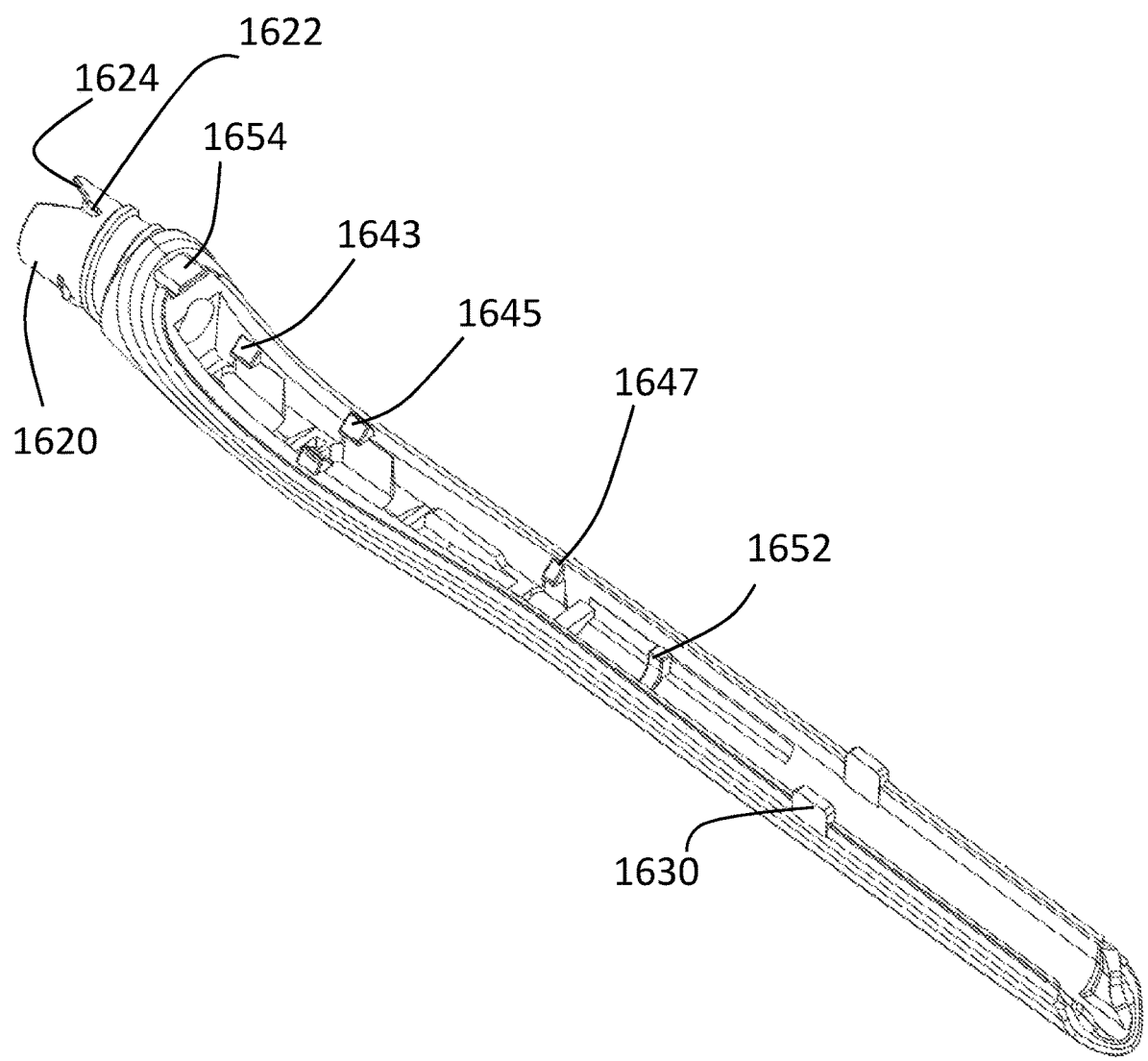

A multi-functional electrosurgical plasma accessory in accordance with a second preferred embodiment of the present invention is described with reference to FIGS. 11A-17D. In FIGS. 11A-11G the electrosurgical attachment 1100 has a handpiece 1700, a gas supply tube 1110 extending from the proximal end of the handpiece 1700, a connector 1120 for connecting the gas supply tube 1110 to a source of gas (not shown), an electrical line 1130 extending from the proximal end of the handpiece 1700, a connector 1140 for connecting the electrical line to an electrosurgical generators and an extendable probe 1300 connected to the distal end of the handpiece 1700.

The probe assembly has a collet 600, a spacer 1500, a shaft member 1400, a heat-resistant tip formed, for example, form ceramic material, an electrode 1370 and a metal contact 1380. The electrode 1390 has a plastic crimp 1390 near its distal end to hold the electrode in the center of the channel in the shaft 1400. The shaft member 1400, shown in FIGS. 14A-14G has a unitary design, for example, made of plastic, having a collar or grip member 1410 with a plurality of depressions or grooves 1412 for gripping the shaft, a neck 1420, and an elongated portion 1430 having a plurality of engagement tines 1432. The elongated portion is predominantly cylindrical but has opposing flat sides 1434 used for alignment with the spacer 1500. The neck 1420 has a channel within it for receiving the electrode 1370.

The second embodiment has an alternative system and method for connecting a probe assembly 1300 to a handpiece 1600 of a multi-functional electrosurgical plasma accessory. The handpiece has an upper portion show in in FIGS. 16A-16L. The lower portion is show in in FIGS. 17A-D. The distal end of the handpiece 1600 has a connector portion 1620 having external threads for mating with a collet 1600 on a probe assembly 1300. The neck of the connector portion of the handpiece has an alignment slot 1622 with side portions 1624 angling in from the open end of the slot 1622. The sides of the slot are substantially straight and parallel to the length of the slot near the closed end of the slot. The angled sides serve to rotationally self-align a guide member on a spacer of the probe assembly to ensure that the probe assembly is properly aligned with the handpiece. The connector in the handpiece has an interior channel with a plurality of beveled shoulders to axially align the spacer 1500 with the handpiece 1600. The spacer 1500 has a first end for inserting into the connector portion of the handpiece. The first end has a beveled portion 1536 to provide initial axial self-alignment. The spacer has a beveled shoulder 1534 partially along its body 1530 to provide further axial self-alignment of the spacer with the connector portion of the handpiece. The spacer further has a stop member 1520, which will be adjacent the distal end of the connector portion of the handpiece when the probe assembly is fully inserted into the handpiece. The spacer still further has a ridge 1522 parallel with its axis for radial alignment of the spacer with the handpiece. The distal end of the ridge 1522 is angled to provide tactile radial self-alignment of the probe assembly with the handpiece.

The bottom or lower portion 1800 of the handpiece 1700 has a body 1860, a butterfly-shaped grip 1862, a groove for engaging with tabs 1730 in the upper portion, and a ridge structure 1864 for engaging with the ridge structure 1712 in the upper portion of the handpiece.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An attachment for an electrosurgical system comprising:
    an extendable probe assembly comprising:
        a shaft member having an interior channel, a distal end and a proximal end, comprising:
            a neck portion at said distal end of said shaft member;
            a grip portion; and
            a keyed elongated portion extending toward said proximal end of said shaft member, wherein said elongated portion has a shaft stop member and a first alignment feature;
        a tube having an interior channel, said tube having a proximal end secured within said interior channel of said shaft and a distal end extending from said distal end of said shaft;
        an electrode within said interior channel of said tube;
        a spacer movably connected to said shaft member, comprising:
            a body having a first portion, second portion, and a spacer stop member, said first portion having a keyed first interior channel for slidably receiving said elongated portion of said shaft member, said keyed first interior channel of said first portion having an interior second alignment feature for rotationally aligning said keyed first interior channel of said first portion with said first alignment feature of said keyed elongated portion of said shaft, said first and second alignment features preventing rotation of said shaft member within said spacer, and said second portion of said body having a second interior channel connected to said first interior channel and an shoulder within said second interior channel; and
            a metal contact in said second interior channel of said spacer, said metal contact being connected to said electrode, wherein said shoulder in said second interior channel of said spacer prevents said metal contact and said electrode from moving longitudinally relative to said spacer; and
        a collet for connecting said probe assembly to an electrosurgical handpiece, said collet having an interior ridge for engaging said spacer stop member and having interior threads for engaging with threads on said electrosurgical handpiece;
    wherein said elongated portion of said shaft is movable within said spacer between a first position in which a portion of a distal end of said electrode extends out of said tube and a second position in which said distal end of said electrode does not extend out of said tube.

2. A attachment for an electrosurgical system according to claim 1, further comprising a heat resistant tube abutting a distal end of said tube.

3. A attachment for an electrosurgical system according to claim 2, further comprising a stiffening member over said abutment between said heat resistant tube and said distal end of said elongated tube.

4. An attachment for an electrosurgical system according to claim 1, wherein said shaft stop member comprises a plurality of tines extending from a proximal end of said elongated portion of said shaft.

5. An attachment for an electrosurgical system according to claim 1, wherein said alignment feature of said shaft comprises a flat surface on said elongated portion of said shaft and said interior alignment feature of said spacer comprised a flat surface on the interior of said spacer.

6. An attachment for an electrosurgical system according to claim 1, wherein said spacer further has an outer alignment feature, wherein said outer alignment feature of said spacer comprises a pair of ridges of different widths spaced on the exterior circumference of said spacer.

7. An attachment for an electrosurgical system according to claim 1, wherein said tube comprises:
    insulating tubing;
    a heat-resistant tip adjacent to a distal end of said insulating tubing;
    a stiffening element over a joint between said insulating tubing and said heat-resistant tip; and shrink wrap over a portion of said insulating tubing, said heat-resistant tip and said stiffening element.

8. An attachment for an electrosurgical system according to claim 1, wherein said grip comprises:
a collar having a plurality of depressions.

9. An attachment for an electrosurgical system according to claim 1, wherein said spacer further has an outer alignment feature, wherein said outer alignment feature of said spacer comprises a pair of ridges of different widths spaced on the exterior circumference of said spacer.

10. An attachment for an electrosurgical system comprising:
an extendable probe assembly comprising:
a shaft member having an interior channel, a distal end and a proximal end, comprising:
a neck portion at said distal end of said shaft member;
a grip portion; and
a keyed elongated portion extending toward said proximal end of said shaft member, wherein said elongated portion has a shaft stop member and a first alignment feature;
a tube having an interior channel, said tube having a proximal end secured within said shaft member and a distal end extending from said distal end of said shaft;
an electrode within said interior channel of said tube;
a spacer movably connected to said shaft member comprising:
a body having a first portion, second portion, and a spacer stop member, said first portion having a keyed first interior channel for slidably receiving said keyed elongated portion of said shaft member, said keyed first interior channel of said first portion having an interior second alignment feature for rotationally aligning said keyed first interior channel of said spacer with said first alignment feature of said keyed elongated portion of said shaft, said first and second alignment features preventing rotation of said shaft member within said spacer, and said second portion of said body having a second interior channel connected to said first interior channel and a shoulder within said second interior channel; and
a metal contact in said second interior channel of said spacer, said metal contact being connected to said electrode, wherein said shoulder in said second interior channel of said spacer prevents said metal contact and said electrode from moving longitudinally relative to said spacer; and
wherein said elongated portion of said shaft is longitudinally movable within said spacer between a first position in which a portion of a distal end of said electrode extends out of said tube and a second portion in which said distal end of said electrode does not extend out of said tube.

11. An attachment for an electrosurgical system according to claim 10, wherein said shaft stop member comprises a plurality of tines extending from a proximal end of said elongated portion of said shaft.

12. An attachment for an electrosurgical system according to claim 10, wherein said first alignment feature of said shaft comprises a flat surface on said elongated portion of said shaft and said interior second alignment feature of said spacer comprised a flat surface on the interior of said spacer.

13. An attachment for an electrosurgical system according to claim 10, wherein said first alignment feature of said shaft comprises opposing flat surfaces on said elongated portion of said shaft and said interior second alignment feature of said spacer comprises opposing flat surfaces on the interior of said spacer.

14. An attachment for an electrosurgical system according to claim 10, wherein said tube comprises:
insulating tubing;
a heat-resistant tip adjacent to a distal end of said insulating tubing;
a stiffening element over a joint between said insulating tubing and said heat-resistant tip; and
shrink wrap over a portion of said insulating tubing, said heat-resistant tip and said stiffening element.

15. An attachment for an electrosurgical system according to claim 10, wherein said grip comprises:
a collar having a plurality of depressions.

* * * * *